US009957125B2

(12) United States Patent
Ray

(10) Patent No.: US 9,957,125 B2
(45) Date of Patent: May 1, 2018

(54) SANITARY AUTOMATIC GLOVE DISPENSING APPARATUS AND METHOD OF USE

(71) Applicant: Ilya Ray, Trevor, WI (US)

(72) Inventor: Ilya Ray, Trevor, WI (US)

(*) Notice: Subject to any disclaimer, the term of this patent is extended or adjusted under 35 U.S.C. 154(b) by 0 days. days.

(21) Appl. No.: 15/015,250

(22) Filed: Feb. 4, 2016

(65) Prior Publication Data
US 2016/0152430 A1 Jun. 2, 2016

(51) Int. Cl.
B65H 7/20 (2006.01)
A41D 19/015 (2006.01)
B65H 3/00 (2006.01)
A61B 42/50 (2016.01)
A61B 50/20 (2016.01)
A61B 42/40 (2016.01)
A61B 90/98 (2016.01)
A41D 19/00 (2006.01)
A61B 17/00 (2006.01)

(52) U.S. Cl.
CPC .......... B65H 7/20 (2013.01); A41D 19/015 (2013.01); A61B 42/40 (2016.02); A61B 42/50 (2016.02); A61B 50/20 (2016.02); A61B 90/98 (2016.02); B65H 3/00 (2013.01); A41D 19/0055 (2013.01); A61B 2017/00398 (2013.01); A61B 2017/00734 (2013.01)

(58) Field of Classification Search
CPC ...... A61B 42/40; A61B 42/50; G08B 21/245; A47K 5/1217; A47F 3/02
See application file for complete search history.

(56) References Cited

U.S. PATENT DOCUMENTS

| 2,264,631 A | 12/1941 | Fetty |
| 3,432,217 A | 3/1969 | Cowan |
| 4,108,513 A | 8/1978 | Lander |
| 4,372,354 A | 2/1983 | Moore |

(Continued)

OTHER PUBLICATIONS

"Norovirus Transmission Between Hands, Gloves, Utensils, and Fresh Produce During Simulated Food Handling," Appl Environ Microbiol., Sep. 2014; 80(17): 5403-5410. doi: 10.1128/AEM. 01162-14, M. Ronnqvist; E. Aho; A. Mikkela; J. Ranta; P. Tuominen; M. Rano and L. Maunula.

(Continued)

Primary Examiner — Timothy Waggoner
(74) Attorney, Agent, or Firm — Jansson Munger McKinley & Kirby Ltd.

(57) ABSTRACT

A sanitary automatic glove dispensing apparatus and method of use. The automatic sanitary glove dispensing apparatus, based on one or more received dispensing events, dispenses pairs of connected protective gloves stored on a roll of protective gloves and overlapped in a pre-determined pattern, by both cuff ends so both finger ends of the protective gloves are not contaminated during dispensing. After a pair of protective gloves are dispensed by both cuff ends, no additional protective gloves are exposed from the apparatus until another protective glove dispensing event is received, thereby protecting remaining protective gloves in the apparatus from contamination by noroviruses and bacteria from a surrounding environment and from other users of the apparatus.

21 Claims, 17 Drawing Sheets

(56) References Cited

U.S. PATENT DOCUMENTS

| | | | |
|---|---|---|---|
| 4,667,697 A * | 5/1987 | Crawford | F16K 15/025 137/315.33 |
| 4,771,966 A | 9/1988 | Anderson | |
| 4,790,490 A | 12/1988 | Chakravorty | |
| 4,796,825 A | 1/1989 | Hawkins | |
| 4,826,262 A | 5/1989 | Hartman et al. | |
| D307,841 S | 5/1990 | Hanifl et al. | |
| 4,942,992 A | 7/1990 | Fischer et al. | |
| 4,960,248 A | 10/1990 | Bauer et al. | |
| 4,979,688 A | 12/1990 | Tinker | |
| 5,088,620 A | 2/1992 | Kelliher et al. | |
| 5,097,950 A | 3/1992 | Weiss et al. | |
| 5,125,623 A | 6/1992 | Kiedinger | |
| 5,199,119 A | 4/1993 | Weber | |
| D335,373 S | 5/1993 | Mosior | |
| 5,329,672 A | 7/1994 | Froehlich et al. | |
| 5,361,812 A | 11/1994 | Arneson et al. | |
| 5,398,931 A | 3/1995 | Tahgoh | |
| 5,409,181 A | 4/1995 | Patrick | |
| 5,417,261 A | 5/1995 | Kanzler et al. | |
| 5,511,763 A | 4/1996 | Green | |
| D375,010 S | 10/1996 | Karnes | |
| 5,625,908 A | 5/1997 | Shaw | |
| D385,626 S | 10/1997 | Mosior et al. | |
| D387,981 S | 12/1997 | Mosior et al. | |
| 5,772,291 A | 6/1998 | Byrd et al. | |
| 5,816,440 A * | 10/1998 | Shields | B65D 83/0805 206/438 |
| 5,860,561 A * | 1/1999 | Saldana | A61F 15/001 221/197 |
| 5,878,909 A | 3/1999 | Rogow | |
| 5,884,784 A | 3/1999 | Betts, Sr. | |
| 5,927,543 A | 7/1999 | Dejardin et al. | |
| 6,021,920 A | 2/2000 | Aldape | |
| 6,082,587 A | 7/2000 | Martindale | |
| 6,098,917 A | 8/2000 | Cruz | |
| 6,189,736 B1 | 2/2001 | Phallen | |
| D460,301 S | 7/2002 | Milliorn | |
| 6,426,701 B1 * | 7/2002 | Levy | G08B 21/24 137/552.7 |
| 6,502,718 B2 * | 1/2003 | Fitzgerald | G07F 5/26 221/131 |
| 6,543,642 B1 | 4/2003 | Milliorn | |
| 6,607,160 B2 | 8/2003 | Lewis et al. | |
| 6,708,841 B2 | 3/2004 | Baughman | |
| 6,749,148 B2 | 6/2004 | Helfer-Grand | |
| 6,820,753 B2 | 11/2004 | Kurtz et al. | |
| 6,894,270 B2 | 5/2005 | Bailey | |
| 6,901,723 B2 | 6/2005 | Jordan et al. | |
| 6,903,654 B2 | 6/2005 | Hansen et al. | |
| 6,953,130 B2 | 10/2005 | Corbett | |
| 6,977,588 B2 | 12/2005 | Schotz | |
| 7,063,233 B2 | 6/2006 | Jordan et al. | |
| D530,224 S | 10/2006 | Mattesky | |
| D540,082 S | 4/2007 | Mandel | |
| 7,296,765 B2 | 11/2007 | Rodrian | |
| 7,588,168 B2 | 9/2009 | Bagwell et al. | |
| 7,635,067 B1 * | 12/2009 | Flynn | A61B 42/50 221/221 |
| 7,774,096 B2 * | 8/2010 | Goerg | A47K 10/3845 221/2 |
| 7,841,556 B2 | 11/2010 | Elliott et al. | |
| 7,963,475 B2 | 6/2011 | Rodrian | |
| 7,987,756 B2 | 8/2011 | Lewis et al. | |
| 8,132,692 B2 | 3/2012 | Jordan | |
| 8,196,775 B1 | 6/2012 | Ballesteros | |
| 8,237,558 B2 | 8/2012 | Seyed Momen et al. | |
| 8,419,024 B1 | 4/2013 | Arroyo-Ferrer | |
| 8,463,765 B2 | 6/2013 | Lesavich | |
| 8,588,701 B2 * | 11/2013 | Wigard | H04W 24/10 370/328 |
| D696,107 S | 12/2013 | Kimple et al. | |
| 8,608,719 B2 | 12/2013 | Ray | |
| 8,617,130 B2 | 12/2013 | Ray | |
| 8,631,968 B2 * | 1/2014 | Taylor | B65D 83/0817 221/36 |
| 8,700,809 B2 | 4/2014 | Ferragut, II | |
| 8,960,493 B1 | 2/2015 | Dennison et al. | |
| 8,960,514 B2 | 2/2015 | Lee | |
| 9,037,564 B2 | 5/2015 | Lesavich et al. | |
| D732,305 S | 6/2015 | Cosentino | |
| 9,078,647 B2 | 7/2015 | Dennison et al. | |
| 9,095,299 B2 | 8/2015 | Ray | |
| 9,137,250 B2 | 9/2015 | Lesavich et al. | |
| 9,237,899 B2 | 1/2016 | Ray | |
| 2002/0040912 A1 | 4/2002 | McHugh | |
| 2002/0113079 A1 | 8/2002 | Corbett | |
| 2003/0057222 A1 | 3/2003 | Million | |
| 2003/0116580 A1 | 6/2003 | Baughman | |
| 2003/0222779 A1 | 12/2003 | Schotz et al. | |
| 2003/0230591 A1 | 12/2003 | Jordan et al. | |
| 2004/0099623 A1 | 5/2004 | Kurtz | |
| 2004/0134924 A1 | 7/2004 | Hansen et al. | |
| 2004/0172918 A1 | 9/2004 | Jordan et al. | |
| 2004/0226962 A1 | 11/2004 | Mazursky | |
| 2006/0144847 A1 | 7/2006 | Jordan et al. | |
| 2006/0175341 A1 | 8/2006 | Rodrian | |
| 2007/0010389 A1 | 1/2007 | Cutrona et al. | |
| 2007/0012714 A1 | 1/2007 | Bagwell et al. | |
| 2007/0158359 A1 | 7/2007 | Rodrian | |
| 2007/0213877 A1 | 9/2007 | Hart et al. | |
| 2007/0215628 A1 | 9/2007 | Tramontina | |
| 2007/0222554 A1 | 9/2007 | Hart | |
| 2008/0116314 A1 | 5/2008 | Elliott | |
| 2009/0108122 A1 | 4/2009 | Sahud | |
| 2009/0140001 A1 | 6/2009 | Lewis | |
| 2010/0102101 A1 | 4/2010 | Keily | |
| 2010/0117836 A1 * | 5/2010 | Seyed Momen | G01S 1/70 340/573.1 |
| 2010/0134296 A1 * | 6/2010 | Hwang | A47K 5/1217 340/573.1 |
| 2011/0062179 A1 | 3/2011 | Stollery et al. | |
| 2011/0108571 A1 | 5/2011 | Hagleitner | |
| 2011/0208710 A1 | 8/2011 | Lesavich | |
| 2011/0283439 A1 * | 11/2011 | Backhaus | A41D 19/0072 2/159 |
| 2012/0199602 A1 | 8/2012 | Jordan et al. | |
| 2012/0278622 A1 | 11/2012 | Lesavich et al. | |
| 2014/0069951 A1 | 3/2014 | Schmidt | |
| 2014/0189792 A1 | 7/2014 | Lesavich et al. | |
| 2015/0053709 A1 | 2/2015 | Dennison et al. | |
| 2015/0053710 A1 | 2/2015 | Dennison et al. | |
| 2015/0230645 A1 | 8/2015 | Dennison et al. | |
| 2015/0374441 A1 * | 12/2015 | Machado | A61B 50/20 221/2 |
| 2015/0379301 A1 | 12/2015 | Lesavich et al. | |

OTHER PUBLICATIONS

"Norovirus on Swabs Taken from Hands Illustrate Route of Transmission: A Case Study," *J Food Prot*. Aug. 2009; 72(8):1753-5, L. Boxman; R. Dijkman; L. Verhoef; A. Maat; G. van Dijk; H. Vennema; M. Koopmans.

"Hand Washing Frequencies and Procedures Used in Retail Food Services," *J Food Prot.*, Aug. 2008, 71(8):1641-50, C. Strohbehn; J. Sneed; P. Paez; J. Meyer.

"Systematic Qualitative Literature Review of Health Care Workers" Compliance with Hand Hygiene Guidelines, Mar. 1, 2015, vol. 43, Issue 3, pp. 269-274, Maura P. Smiddv, MPH; Rhona 0'Connell, PhD; Sile A. Creedon, PhD.

"Vital Signs: Foodborne Norovirus Outbreaks—United States, 2009-2012," Jun. 6, 2014 / 63(22);491-495 Aron J. Hall, DVM; Mary E. Wikswo, MPH; Kimberly Pringle, MD; L. Hannah Gould, PhD; Umesh D. Parashar, MBBS.

"Preliminary Evaluation of the Effect of Glove Use by Food Handlers in Fast Food Restaurants," *Journal of Food Protection*, No. 1, Jan. 2005, pp. 4-207, pp. 187-190(4). Robert A. Lynch; Margaret L. Phillips; Brenda L. Elledge; Sridhar Hanumanthaiah; Daniel T. Boatright.

"Bacterial Contamination of Unused, Disposable Non-Sterile Gloves on a Hospital Orthopedic Ward," *Australas Med J.*, Jun. 30,

(56) References Cited

OTHER PUBLICATIONS

2013;6(6):331-8. doi: 10.4066/AMJ.2013.1675. Print 2013. Hughes KA; Cornwall J; Theis J-C; Brooks HJL.

"Glove Use Information Leaflet," World Health Organization, Aug. 2009, http://www.who.int/gpsc/5may/Glove_Use_Information_Leaflet.pdf.

"Identifying Specific Beliefs to Target to Improve Restaurant Employees' Intentions for Performing Three Important Food Safety Behaviors," *J Am Diet Assoc.*, Jun. 2008;108(6):991-7. doi: 10.1016/j.jada.2008.03.014, Valerie K. Pilling, PhD; Laura A. Brannon, PhD; Carol W. Shanklin, PhD, RD; Amber D. Howells, MS, RD; Kevin R. Roberts, PhD.

"Comprehensive Survey of Hand Hygiene Measurement and Improvement Practices in the Veterans Health Administration," *American Journal of Infection Control*, vol. 41, Issue 11, Nov. 2013, pp. 989-993. Heather Schacht Reisinger, PhD; Jun Yin, MS; Lewis Radonovich, MD; V. Troy Knighton, EdS; Richard A. Martinello, MD; Michael J. Hodgson, MD, MPH; Eli Perencevich, MD, MS.

"Bacterial Contamination of Nonsterile Disposable Gloves Before Use," *American Journal of Infection Control*, vol. 34, Issue 3, Apr. 2006, pp. 128-130, Philippe Berthelot, MD, MPH, PhD; Jonathan Dietemann, Pharm D; Pascal Fascia, MD; Alain Ros, MD; Franck Olivier Mallaval, MD; Frederic Lucht, MD; Bruno Pozzetto, MD, PhD, Florence Grattard, MD, PhD.

Aug. 2009, World Health Organization, Glove Use Information Leaflet, 4 pp.

\* cited by examiner

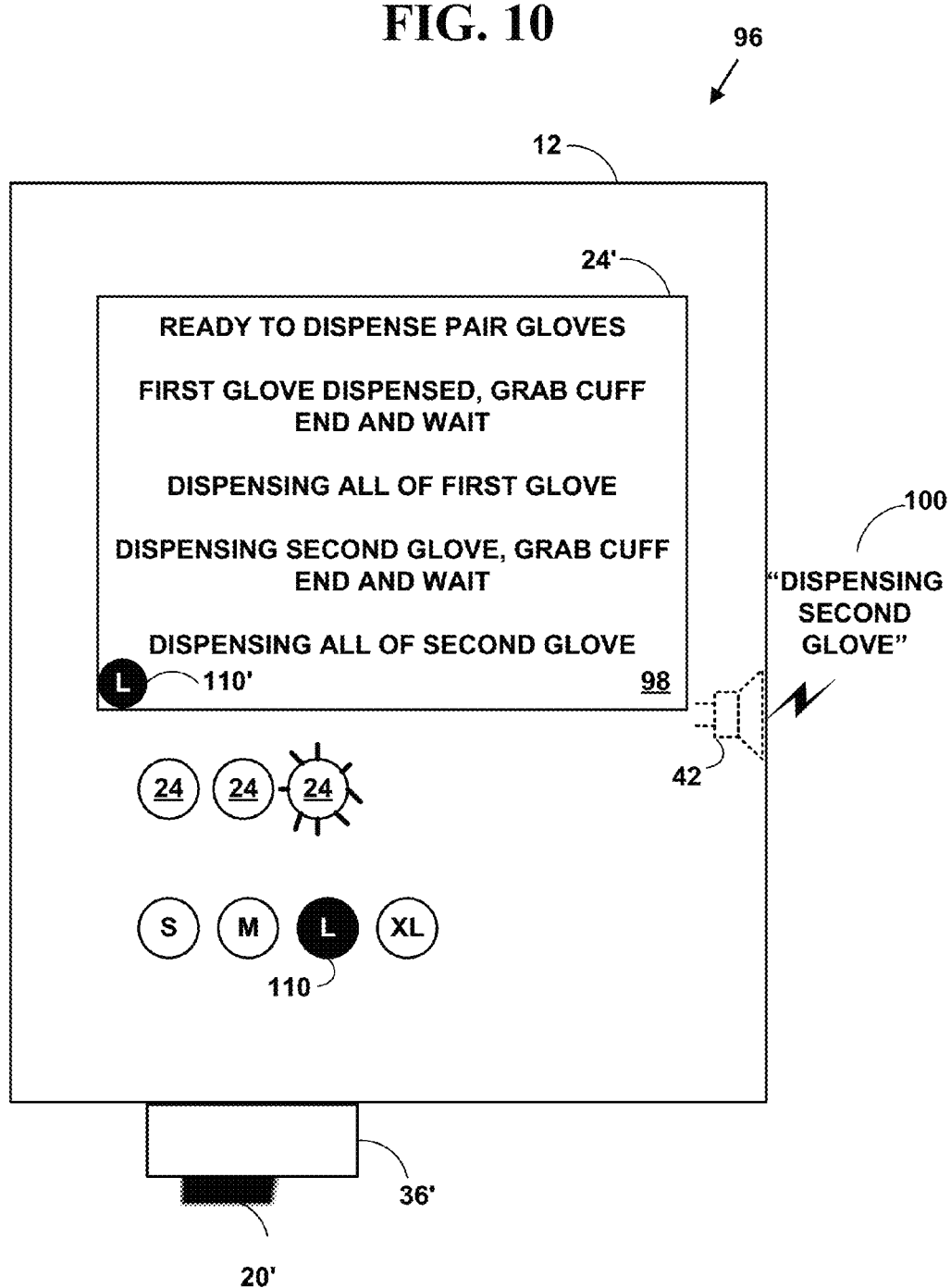

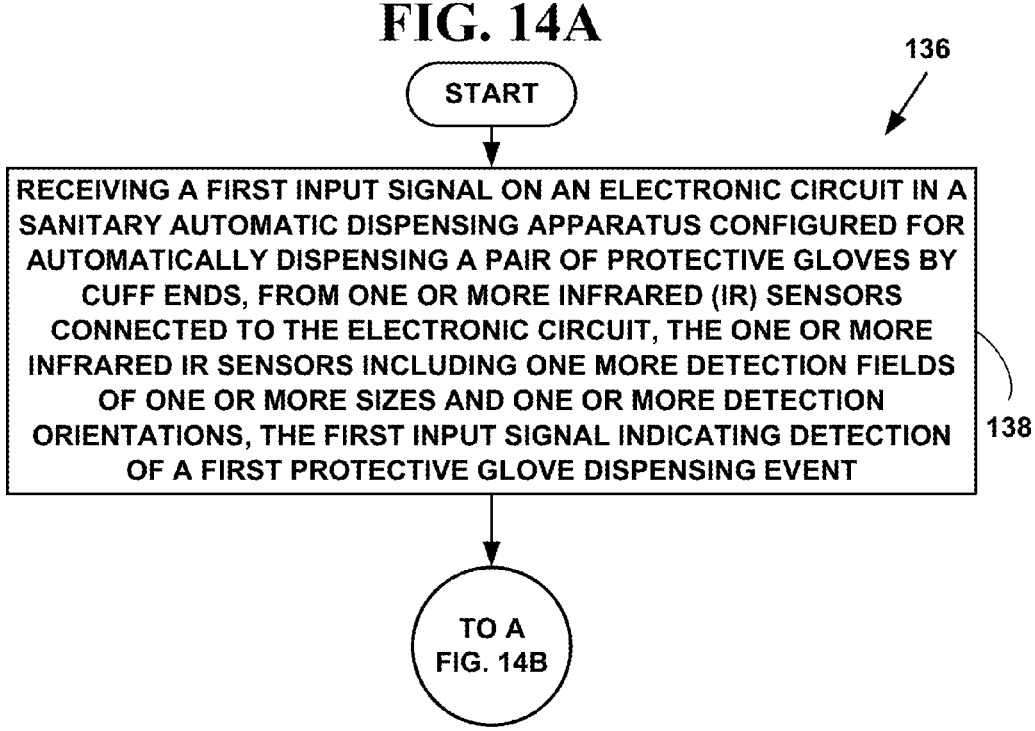

SENDING A PLURALITY OF ELECTRICAL SIGNALS FROM THE ELECTRONIC CIRCUIT TO A RACK CIRCUIT ON A GLOVE ROLL RACK TO MOVE A ROLL OF PROTECTIVE GLOVES IN THE GLOVE ROLL RACK WITH AN ELECTRIC MOTOR A PLURALITY OF TIMES FOR: (1) AUTOMATICALLY ADVANCING THE ROLL OF PROTECTIVE GLOVES A FIRST DISTANCE TO EXPOSE A FIRST PROTECTIVE GLOVE BY A FIRST CUFF END TO A USER; (2) AUTOMATICALLY ADVANCING THE ROLL OF PROTECTIVE GLOVES A SECOND DISTANCE TO FULLY DISPENSE THE FIRST PROTECTIVE GLOVE BY THE FIRST CUFF END TO THE USER; (3) AUTOMATICALLY ADVANCING THE ROLL OF PROTECTIVE GLOVES A THIRD DISTANCE TO EXPOSE A SECOND PROTECTIVE GLOVE BY A SECOND CUFF END TO THE USER; (4) AUTOMATICALLY ADVANCING THE ROLL OF PROTECTIVE GLOVES A FOURTH DISTANCE TO FULLY DISPENSE THE SECOND PROTECTIVE GLOVE BY THE SECOND CUFF END TO THE USER, WHEREIN THE FOURTH DISTANCE FULLY DISPENSES THE SECOND PROTECTIVE GLOVE WITHOUT EXPOSING ANOTHER CUFF END OF ANOTHER PAIR OF PROTECTIVE GLOVES STORED ON THE ROLL OF PROTECTIVE GLOVES OUTSIDE THE APPARATUS THEREBY PROTECTING THE REMAINING PAIRS OF PROTECTIVE GLOVES ON THE ROLL OF PROTECTIVE OF PROTECTIVE GLOVES FROM CONTAMINATION BY A SURROUNDING ENVIRONMENT OR BY OTHER USERS OF THE APPARATUS, WHEREIN THE ROLL OF PROTECTIVE GLOVES INCLUDES A PLURALITY OF INDIVIDUAL PROTECTIVE GLOVES STORED AS PAIRS OF PROTECTIVE GLOVES, WHEREIN EACH OF THE INDIVIDUAL GLOVES IN THE PAIR OF PROTECTIVE GLOVES IS ROLLED ON THE ONE OR MORE ROLLS OF PROTECTIVE GLOVES IN A PRE-DETERMINED OVERLAP PATTERN, WHEREIN A PAIR OF PROTECTIVE GLOVES FROM THE PLURALITY OF PROTECTIVE GLOVES IS DISPENSED FROM THE ONE OR MORE ROLLS OF PROTECTIVE GLOVES BY THE CUFF ENDS AVOIDING CONTAMINATING THE FINGER SURFACES BY THE USER OF THE PROTECTIVE GLOVES DURING DISPENSING
— 140

↓

( END )

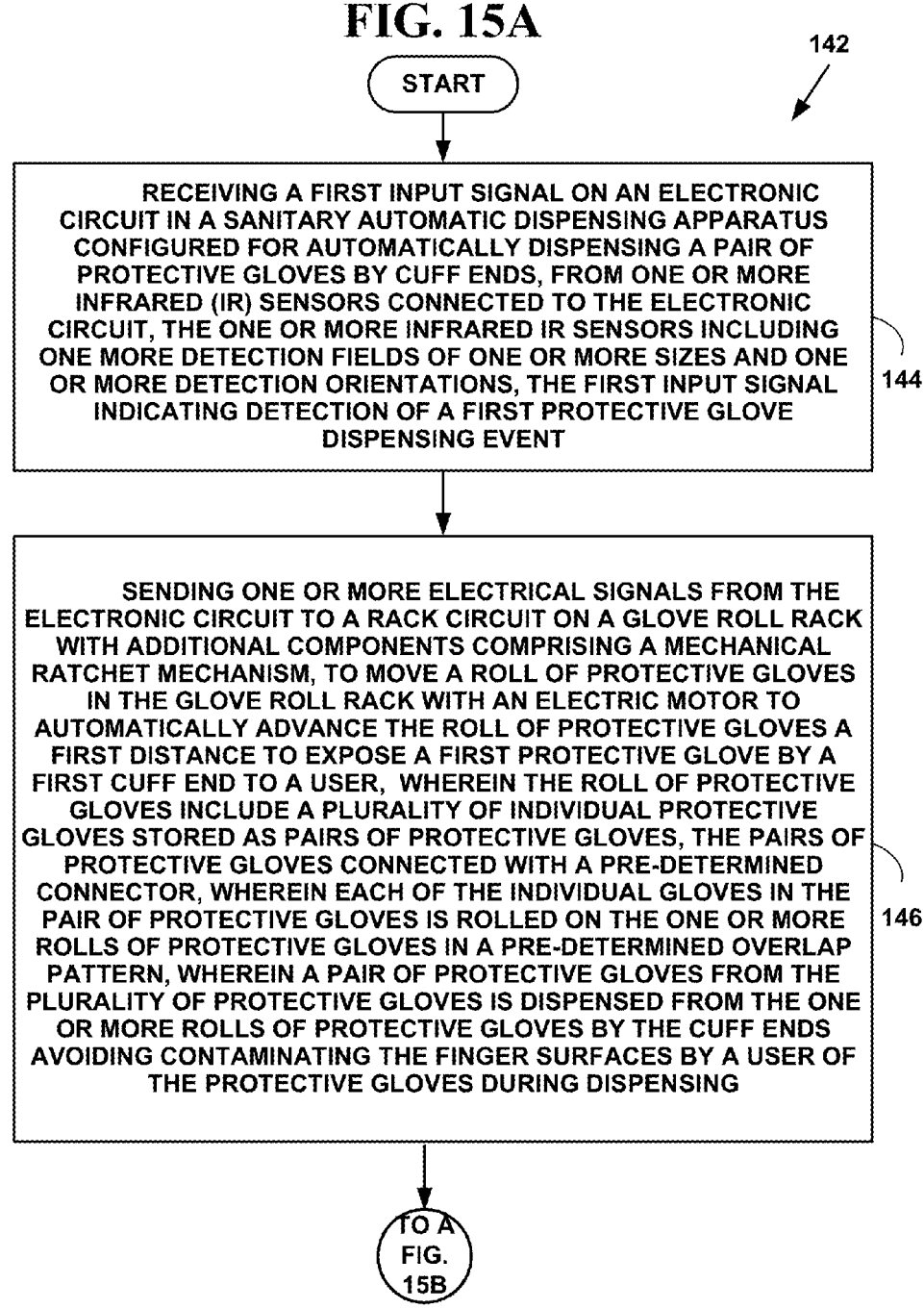

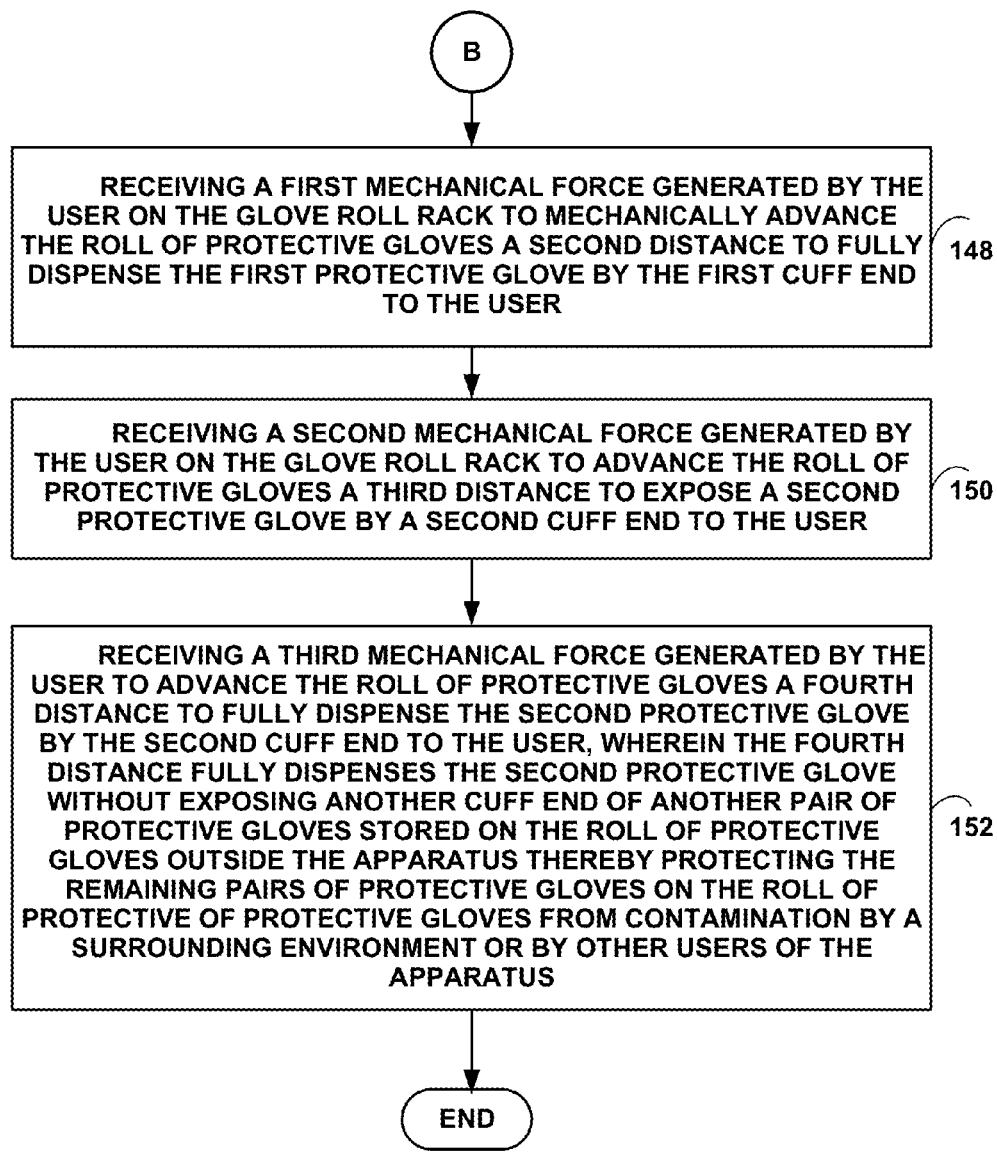

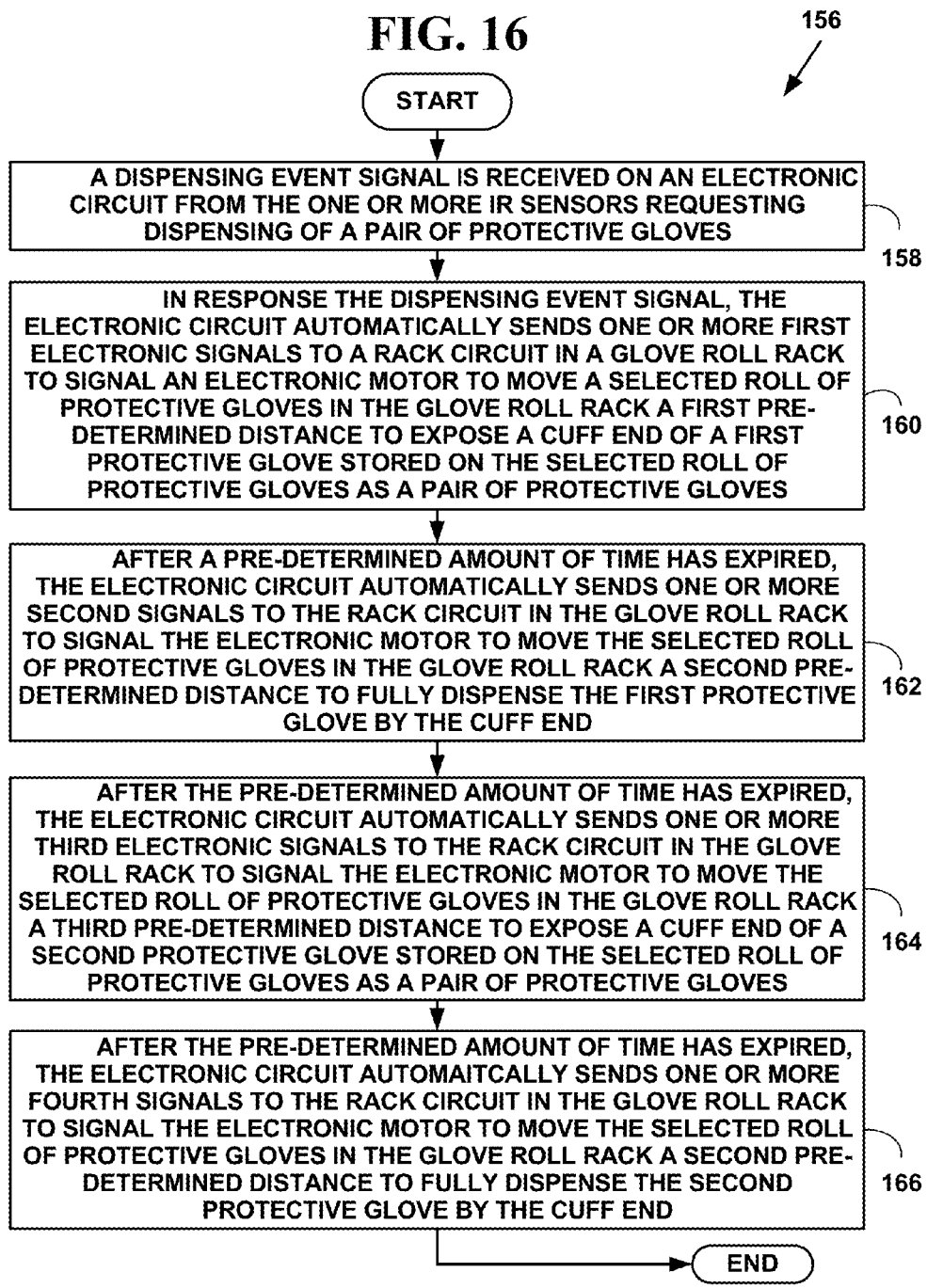

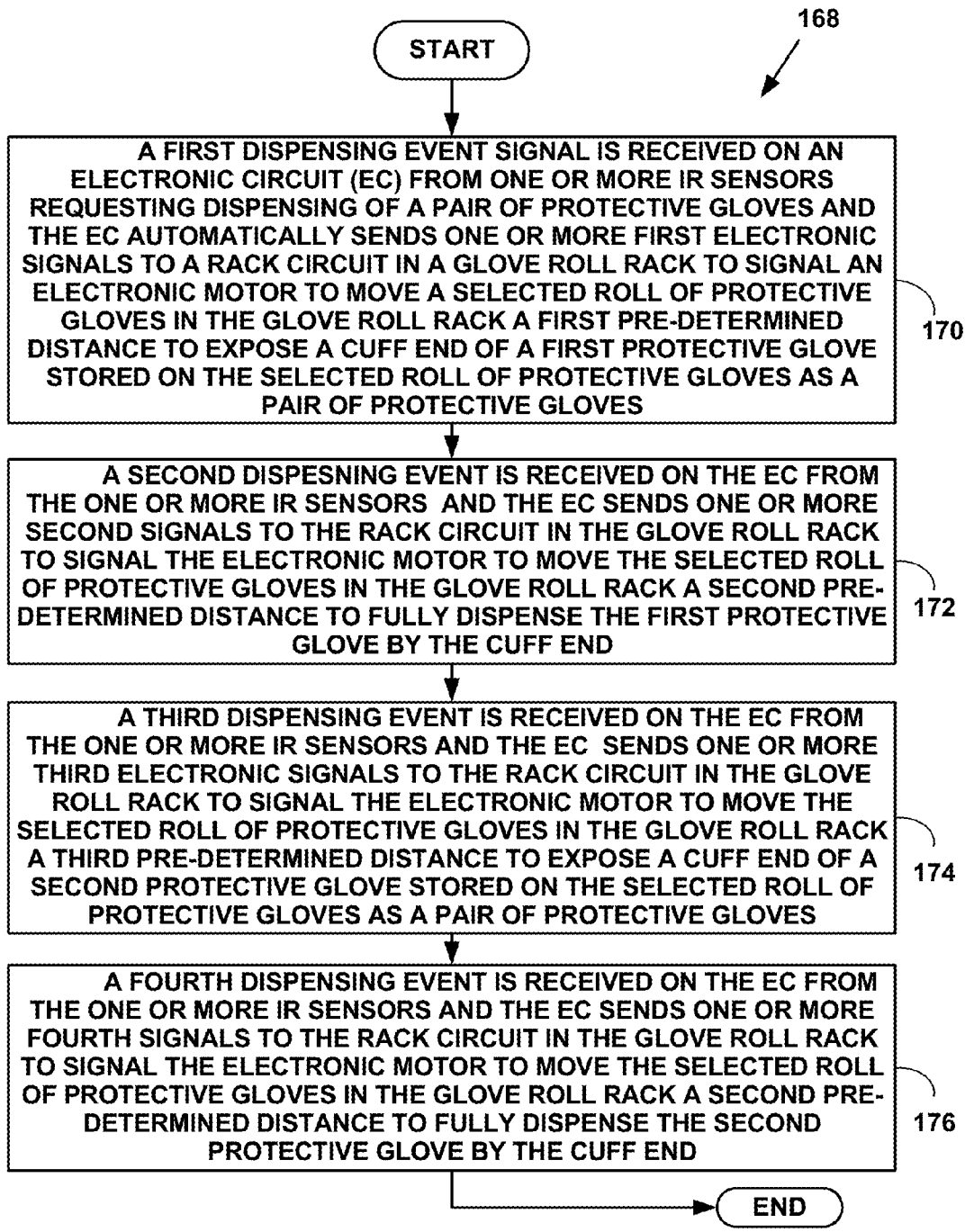

SANITARY AUTOMATIC GLOVE DISPENSING APPARATUS AND METHOD OF USE

FIELD OF INVENTION

This application relates to automatic dispensing of protective gloves. More specifically, it relates to a sanitary automatic glove dispensing apparatus and method of use.

BACKGROUND OF THE INVENTION

Hand to person transfer of pathogenic organisms due to poor hand hygiene is a well-documented in the medical literature and results in thousands of deaths and hundreds of millions of dollars of health care expense each year. There are recognized problems associated with hand hygiene documented in hospitals, nursing homes, day-care facilities, dental offices, the food service industry, etc.

In 2005 the World Health Organization launched its first Global Patient Safety Challenge, focusing on the importance of hand hygiene. Hospital acquired infections occur in an estimated 5 to 10% of hospitalized patients and results in prolonged hospital stays, deaths and hundreds of millions of health care dollars each year. Proper hand hygiene has been recognized as the single most important element to control infection rates in all types of care facilities across all age groups. Multiple studies have shown that consistent hand washing or sanitizing hygiene compliance is low.

An important element of hand hygiene practice is the correct application of single use, non-sterile gloves, which can reduce the spread of pathogenic organisms. Unfortunately studies have demonstrated the presence of bacteria on unused gloves in open boxes, which are commonly used in all settings where non-sterile gloves are worn. Common skin bacteria and pathogenic bacteria were cultured from the glove surfaces, indicating that the non-sterile gloves may be a potential source of bacteria transmission in the health care setting. The method of boxing and retrieving the glove may be responsible for the contamination of the glove surface.

Norovirus is the leading cause of gastroenteritis and foodborne disease in the US, causing an estimated 56,000 to 71,000 hospitalizations and 570-800 deaths annually. Other recognized pathogens on food service personnel include *Staphylococcus aureus, Escherichia coli, Klebsiella* spp. and *coliform* bacteria. Transmission is mainly fecal-oral route. Up to 46% of gloved samples tested in one study in the fast food setting showed bacterial contamination and a separate study showed that norovirus contaminated gloves transmitted virus to food servings more readily than a contaminated cucumber. The observed tendency of food workers to wear gloves for an extended period of time has been felt to be one of the potential failure of gloves to reduce or prevent bacterial contamination.

The Food and Drug Association (FDA) 2001 Food Code, section 3-301.11 states, "Except when washing fruits and vegetables, food employees may not contact exposed ready to eat foods with their bare hands and should use suitable utensils . . . and single use gloves."

Regardless of the setting where non-sterile, one time use gloves are used there is a significant risk of contamination of the glove surface occurring when the glove is removed from a box or other dispenser.

There are a number of problems associated with protective gloves. One serious problem is that protective gloves are sold in paper boxes that are open on the top surface through a central oval shaped opening, the same configuration seen with tissue dispensers. When a glove is taken from the box it is grasped through the opening. Virtually all glove boxes present the glove so it is removed from the box by grasping the glove from the working surface that includes the base of the fingers and the palm. The cuff of the glove is not visible from most all glove boxes. It is common that more than one glove is grasped at a time so the gloves are held by the working surface until they can be put on. Often more than two gloves are grasped and the third or fourth glove removed from the box is pushed back into the box. The remaining gloves are now potentially contaminated by the person currently putting on the gloves and will receive further direct hand contact contamination by the next person removing a pair of gloves. Each pair of gloves removed from the open box, may have received surface contamination from two persons, prior to being used for direct patient care or food preparation.

Another problem is that protective gloves are kept in open boxes on a wall dispenser or on a counter by the wash sink. Further contamination by bacteria and viruses from the surrounding environment is possible by airborne, respiratory borne or splash contamination from the hand washing area which may include blood, tissue and other medical related fluids or food fluids or cleaning fluids, etc.

Another problem is that even for the most diligent and motivated health care workers, it is not possible to easily grasp gloves one at a time from the non-working surface. In the busy flow of a typical patient care unit gloves are grasped as one walks into the room and put on while moving toward the patient with the working surface of the glove coming into contact with bare hands. In those instances where hand hygiene is not performed according to accepted standards, patient to care giver to patient pathogen transmission is possible.

Another problem is that food industry studies have shown that hands or protective gloves contaminated with Norovirus can transmit the virus to the working surface of other protective gloves and then to the food being handled.

Another problem is that different areas of food preparation require frequent glove changes, depending on the specific duty. Many of the individuals involved in the food service industry work part-time and may have limited levels of education. Understanding the importance of hand hygiene and glove wearing procedures are often discounted leading to poor compliance rates and increased risk of transmission of food borne pathogens.

Another problem is that ongoing monitoring and correcting non-compliant behavior requires direct observation and intervention, a process that is not practical on an ongoing basis in all lines of health and food service industries.

There have been attempts to solve some of the problems associated with dispensing gloves and protective gloves.

For example, U.S. Pat. No. 9,186,012, that issued to Rogers, et al. teaches "The glove dispensing device enables the placement of a glove on a glove retainer. The placement of the glove on the glove retainer at least partially seals the glove with the glove retainer. The user activates a vacuum that draws the glove into a housing of the glove dispensing device. The vacuum inverts the glove thus opening the glove to allow placement of the user's hand within the glove. The user may then remove his hand with the glove from the glove retainer. To assist with removing the glove from the glove retainer, the glove dispensing device provides a release toggle stored within the glove retainer. The user adjusts the release toggle to break the seal of the glove with the glove retainer. Breaking the seal overcomes the pressure applied to the glove from the vacuum. Thus, the glove is applied to the user's hand and ready for use."

U.S. Pat. No. 9,078,647, that issued to Dennison, et al., teaches the following: A disposable glove dispensing system may allow for a user to efficiently put on a disposable glove without touching the outside of the glove. In various embodiments, a disposable glove may comprise an opening for hand entry having a first opening edge and a second opening edge, a first interconnection point located near the first opening edge, where the first interconnection point attaches the disposable glove to a first adjacent disposable glove, and a second interconnection point located near the second opening edge. The second interconnection point may attach the disposable glove to a second adjacent disposable glove, wherein the disposable glove is positioned between the first adjacent disposable glove and the second adjacent disposable glove. Furthermore, a disposable glove dispensing system may comprise a pack of interconnected disposable gloves, and a glove dispenser comprising two glove hangers for hanging the pack of disposable gloves hang."

U.S. Pat. No. 9,003,314 that issued to Cohen teaches "A dispenser is disclosed for flat items such as disposable gloves that are contained within a dispensing bag that has an at least partially-open front side. The dispenser includes a base that has a rear wall and a pair of opposing side walls. A non-opaque cover with a dispensing aperture there through is pivotally fixed between each side wall and adapted to swing between an open and a closed position. At least one elastic cord is stretched between each side wall to urge the dispensing bag towards the cover when the cover is in the closed position and the dispensing bag is between the cover and the at least one elastic cord. The front side of the dispensing bag may be non-opaque and open at a dispensing bag aperture there through, a temporary adhesive being fixed proximate a periphery of the dispensing bag aperture."

U.S. Pat. No. 8,684,226, that issued to Lien teaches "A glove dispensing assembly includes a stack of interfolded gloves. In particular, the gloves are folded in an S-like arrangement including a first fold and a second fold. The finger portion of a leading glove is folded in between a cuff portion and an intermediate portion of a subsequent glove. The manner in which the gloves are folded allows for the gloves to be dispensed in a perpendicular direction or a lateral direction."

U.S. Pat. No. 8,132,692, that issued to Jordan teaches "A method of interfolding gloves including superposing finger portion of second glove adjacent finger portion of first glove, with second glove finger portion being disposed parallel and in a direction opposite the first glove finger portion, in a superjacent opposing relationship. First glove hand and cuff are lapped over second glove finger to create lapped, superjacent opposing fold. By repeatedly lapping previous glove hand over subsequent glove fingers, a glove bundle is formed. Folding can be longitudinal before lapped, superjacent opposing folding. Gloves are disposed in portable dispenser with lapped, superjacent folding and dispensing opening cooperating to dispense one glove, cuff first."

U.S. Pat. No. 8,061,558, that issued to Jordan, et al. teaches "gloves and dispensers for gloves are generally discussed herein with particular discussions extended to disposable gloves packaged in a disposable dispenser configured to engage with a carrier. Aspects of the glove assemblies provided herein include a dispenser case having a flange having locking tab for sliding engagement with a channel on the carrier. The dispenser case may be removed from the carrier and a new dispenser case engaged to the carrier."

U.S. Pat. No. 7,874,455, that issued to Jordan, et al. teaches "Gloves and dispensers for gloves are generally discussed herein with particular discussions extended to disposable gloves packaged in a disposable dispenser configured to engage with a carrier. Aspects of the glove assemblies provided herein include a dispenser case having a flange having locking tab for sliding engagement with a channel on the carrier. The dispenser case may be removed from the carrier and a new dispenser case engaged to the carrier."

U.S. Pat. No. 7,731,056, that issued to Tramontina teaches "A dispenser for dispensing gloves is provided which includes a housing having an exit port, the housing also formed to include a compartment which is configured to hold a plurality of gloves therein. The dispenser includes a glove pusher movably coupled to the housing. At least a portion of the glove pusher is configured to move within the compartment of the housing and push at least a portion of a glove disposed in the compartment through the exit port. A cartridge configured to be disposed into a compartment of a dispenser is disclosed. The cartridge is formed to permit a portion of a dispenser to move into the internal compartment of the cartridge to move at least one of the plurality of gloves at least partially through the at least one opening in the cartridge. A dispensing assembly also may include a stack of gloves or a cartridge containing a plurality of gloves. A method of using a glove dispenser is also provided."

U.S. Pat. No. 7,635,067, that issued to Flynn teaches "A glove dispensing system includes glove bearing sheets and a glove opening mechanism. In use, the glove dispensing system opens a cuff end of the gloves carried by the glove bearing sheets and presents the open gloves to a user. As such, the glove dispensing system provides the user with a substantially sterile glove in a manner that allows the user to easily don the gloves while limiting a risk of the user contaminating an exterior surface of the glove by touching with his hands or other body parts. In one arrangement, the gloves are integrally formed as part of the glove bearing sheets, such as by a heat-sealing process. The gloves can include coupling mechanism that secures the gloves to the glove bearing sheets and that allows ease of removal of the gloves from the glove bearing sheets after being donned by the user by a user."

U.S. Pat. No. 7,063,223, that issued to Jordan et al., teaches "A method of interfolding gloves including superposing finger portion of second glove adjacent finger portion of first glove, with second glove finger portion being disposed parallel and in a direction opposite the first glove finger portion, in a superjacent opposing relationship. First glove hand and cuff are lapped over second glove finger, to create lapped, superjacent opposing fold. By repeatedly lapping previous glove hand over subsequent glove fingers, a glove bundle is formed. Folding can be longitudinal before lapped, superjacent opposing folding. Gloves are disposed in portable dispenser with lapped, superjacent folding and dispensing opening cooperating to dispense one glove, cuff first."

U.S. Pat. No. 6,953,130, that issued to Corbett teaches "An Improved Glove Dispenser is disclosed. The disclosed dispenser will automatically open a pair of standard disposable gloves in response to a user request, preferably by voice. The dispenser further includes a shuttle assembly that will retrieve and position a pair of gloves for donning. The preferred dispenser will accept glove cartridges that can be loaded into the dispenser without being touched by the hands of the person installing the cartridges. In other embodiments of the disclosed dispenser, there is the capability to provide two or more different-sized or configured gloves for donning by users. The preferred dispenser further includes an embodiment whereby the gloves are inflated prior to being donned, in order to further assist the user in donning the gloves. The preferred dispenser further includes a glove donning rack assembly that has a unique glove release assembly for releasing gloves onto hands inserted into them when desired."

U.S. Pat. No. 6,820,753, that issued to Kurtz et al., teaches the following: "A disposable glove dispenser bracket includes a back panel with a magnetic pad attached thereto for supporting the dispenser and lateral side panels with flanges to grip and hold a glove dispenser box. A biasing spring maintains the glove dispenser box appropriately positioned within the dispenser bracket."

U.S. Pat. No. 6,708,841, that issued to Baughman teaches "Glove dispenser having a back plate, a cover, a angled rack for securing a pre-packaged box of gloves within the device at an angle with respect to the back plate, and an aperture in the cover through which gloves can be dispensed at an ergonomic angle."

U.S. Pat. No. 6,543,642, that issued to Milliorn teaches "The present invention is directed to a glove dispenser system that includes a reusable container and a disposable pouch containing stacked, partially folded gloves. The container is rigid and generally rectangular and has a lid and a bottom, spaced, parallel front and back walls, two spaced, parallel side walls and an opening in the lid. The pouch is generally rectangular shaped and it has a pair of spaced parallel extending faces yieldably connected to one another. One of the faces has an opening aligned with the opening in the lid of the container. The pouch contains a plurality of gloves in a stacked folded relationship with one another. The folded relationship being formed by a thumb of the glove being folded under a palm area of the glove and fingers of the glove being folded over the thumb and the palm area. The configuration of the pouch opening and the folded relationship of the gloves provides for the removal of one of the plurality of glove at a time during a dispensing procedure."

U.S. Pat. No. 6,375,034, that issued to Corbett teaches "An Improved Glove Dispenser is disclosed. Also disclosed is a device that permits a user to don gloves without first touching their exterior. The disclosed device includes a plurality of gloves attached by their cuffs to a filament, with the filament and cuffs being dispensed from an exchangeable glove cartridge. It is a further feature that the dispenser may be responsive to a user's voice. Furthermore, the invention provides a new method for donning gloves that will prevent user contamination of the gloves by touching the exterior of the gloves during the donning process."

U.S. Pat. No. 6,042,241, that issued to Marley teaches "A glove dispensing device comprising a cabinet which is designed to be permanently affixed to a wall for dispensing gloves from the glove boxes stored within the cabinet. The cabinet of the glove dispensing device includes a housing and a cover swingably mounted to the housing to allow glove boxes to be inserted into the housing. The cover is provided with a sliding window which opens to permit removal of one glove at a time while closing the sliding window protects the remaining gloves from contaminants and pollutants from the surrounding environment."

U.S. Pat. No. 6,053,380, that issued to Sherrod teaches "This invention is an electronically sanitized medical glove dispensing machine. Not only does the machine place the warm gloves on your hands, it also takes them off and disposes of them in a sanitary way, such as a biohazard bag. The apparatus works via a compressor and a circuit board, along with sensors, "gripper clips", small air hoses, latex gloves, and a stainless steel housing. The sanitized glove is inflated so the hand can be placed in the glove before usage. A hook grips the gloves after the medical worker is finished with them, removes them, and sanitizes them."

U.S. Pat. No. 6,021,920 that issued to Aldape teaches "Emergency and other personnel needing gloves can retrieve them easily for donning using a glove and hand protectant dispenser. The dispenser includes a backboard having at least one detachable glove dispenser member disposed proximate a first edge of the backboard; and at least one detachable hand protectant disposer proximate a second edge of the backboard."

U.S. Pat. No. 6,021,919, that issued to Kelly teaches "The present invention relates to an improved dispenser for sanitary gloves. The dispenser comprises a rectangular enclosure having a top, bottom, left and right side walls, front and back, for receiving individually packaged sanitary gloves. The front is permanently joined to the top, bottom, left and back, while the right side wall is pivotally attached to the bottom wall. The front contains an opening near the top for dispensing the sanitary gloves one at a time. A window near the bottom portion of the front is used to visually inspect the quantity of gloves remaining in the dispenser at any given time."

U.S. Pat. No. 5,966,741 that issued to Klecina teaches "The instant invention provides an article of manufacture that includes: a generally flat planar stacked pad of at least two contiguously supertransposed disposable plastic gloves, each having a generally straight perforated weakened tear line above and generally transverse to the wrist portion of each of the gloves; and, a heat fused portion of the pad substantially adjacent to the perforated weakened tear line opposite the gloves sufficient to produce a substantially rigid single layer of plastic. The substantially rigid single layer further includes: an arrangement for mounting the article on a surface selected from the group consisting of a hole formed through the substantially rigid single layer, double sided adhesive pads mounted on the substantially rigid single layer or the combination of a hole and double sided adhesive pads; and, a label including printed indicia affixed to it."

U.S. Pat. No. 5,921,534 that issued to Hollander et al. teaches "A dispenser for a stack of thin, disposable gloves wherein the gloves are placed within a box-like housing. Included within the housing is a biasing means which presses against the stack of gloves directly adjacent the access opening into the gloves. Each uppermost glove in the stack includes a spot of adhesive which is to connect with the directly underneath glove with this spot being located directly adjacent this access opening. Included within the box-like housing is a dispensing opening with the uppermost glove to partially protrude from this dispensing opening. The users hand is to be inserted into the glove with the glove then being extracted with the adhesive functioning to partially dispense the next glove in the stack of gloves and locate that in a position facilitating connection with a human hand."

U.S. Pat. No. 5,878,909, that issued to Rogow, teaches the following: "A glove dispenser including a glove dispensing housing. Further provided is a plurality of rods extending between side faces of the housing. A pair of gloves are releasably coupled adjacent an opening thereof between each rod. Finally, a dispensing mechanism is situated within the housing for allowing the dispensing of the gloves."

U.S. Pat. No. 5,816,440, that issued to Shields, et al. teaches "Containers for sterile gloves having long cuffs folding over the palms, leaving the fingers exposed beyond, are disclosed such that, upon opening, only the crease of each long cuff/palm overfold can be manually grasped. In one preferred embodiment, sterile containers initially covered with removable film are designed with single openings covered by slit film to dispense multiple surgical or examination gloves. Inside the containers, the overfolded cuffs of successive gloves are folded under the flexed fingers of the first and every succeeding glove, such that the user can serially extract externally sterile gloves by grasping the crease of each long cuff/palm overfold. One bare hand grasps the crease to glove the other. Then, the ungloved hand grasps the crease of the next glove, such that the fingers of the gloved hand can be inserted under the cuff/palm overfold to glove the bare hand. As results, the external surfaces of each extracted glove are never touched by a bare finger or any other contaminated object before use on a patient. Such containers can dispense specified numbers of examination or surgical gloves. In another embodiment, multiple pairs of surgical or examination gloves, each pair with thumbs apposed toward the palms, can be dispensed with the palms touching in separate sterile envelopes, each of which unseals to expose only the creases of the cuff overfolds. Such sterile envelopes can be boxed separately or in rolls from which each package is easily separated."

U.S. Pat. No. 5,028,620, that issued to Kelliher, et al. teaches "A dispenser for gloves comprising a tubular body having a first end and a second end and having a spring disposed therein. The spring is secured to a moveable disc shaped member. A flexible mammillated shaped element having a first end and a second end is secured to the disc shaped member at the first end and secures a plurality of gloves therein. The second end of the mammillated member is secured to the second end of said tubular body. A top element which slideably fits over the second end of the tubular body has an opening therein and a diaphragm element having an aperture therein is secured over said opening. The spring urges the disc shaped member against the flexible mammillated shaped member containing the gloves allowing removal of one glove at a time from the aperture in the diaphragm element."

U.S. Pat. No. 4,992,942 that issued to Fischer, et al. teaches "A glove dispenser comprising a case and a clip fastened to the case. The case has an open position and a closed position. A belt loop is formed on the back surface of the case so as to allow the case to be attached to a belt. The clip is fastened to the case so as to receive the cuff of a glove. The case comprises a back panel, and a connector on the back panel for releasably affixing the front panel in close proximity to the back panel. The clip is interposed between the back panel and the front panel. The clip is a member having a first portion affixed to the case and a second portion in torsional abutment with the first portion. The front panel includes a pocket formed therein for the receipt of additional disposable gloves."

U.S. Pat. No. 4,844,293 that issued to McLaughlin teaches "A dispensing apparatus for disposable, thin plastic gloves is disclosed wherein said gloves may be retrieved by the user one at a time in a relatively simple manner. The apparatus comprises a box-like, generally rectangular enclosure for housing a removably mounted packet containing a plurality of the disposable gloves arranged in the packet in closely spaced, planar unfolded condition. The enclosure is provided with a front window or opening and a removable top cover or cap. The packet of gloves is loaded into the enclosure through a top opening and are disposed so that they may be removed, one at a time, through the front opening of the enclosure. The packet comprises a pair of faces yieldably connected to one another which have a configuration generally conforming to the shape of the gloves in an open palm and finger planar condition. The enclosure includes means to support the packet carrying the gloves in a parallel relationship with the gloves being biasly urged toward the front window to conveniently present the outermost glove to the user."

U.S. Published Patent Application No. 20150374441, that was published by Machado et al., discloses the following: "A glove dispenser has a housing having first and second opposed walls. A glove roll is disposed within the housing for carrying a roll of removable gloves. An electro-mechanical feed mechanism rotates the roll. One or more proximity sensors are positioned within the housing to detect a user's hand and activate rotation of the glove roll. Activators are located on the housing first and second wall which activate the roll to rotate to dispense a glove from the roll. A take-up roll can be provided for receiving roll material after the gloves are dispensed."

U.S. Published Patent Application Nos. 20150230645, 20150053710 and 20150053709 that were published by Dennison, et al. discloses "A disposable glove dispensing system may allow for a user to efficiently put on a disposable glove without touching the outside of the glove. In various embodiments, a disposable glove may comprise an opening for hand entry having a first opening edge and a second opening edge, a first interconnection point located near the first opening edge, where the first interconnection point attaches the disposable glove to a first adjacent disposable glove, and a second interconnection point located near the second opening edge. The second interconnection point may attach the disposable glove to a second adjacent disposable glove, wherein the disposable glove is positioned between the first adjacent disposable glove and the second adjacent disposable glove. Furthermore, a disposable glove dispensing system may comprise a pack of interconnected disposable gloves, and a glove dispenser comprising two glove hangers for hanging the pack of disposable gloves hang."

U.S Published Patent Application No. 20120199602 that was published by Jordan discloses "Gloves and dispensers for gloves are generally discussed herein with particular discussions extended to disposable gloves packaged in a disposable dispenser configured to engage with a holder. Aspects of the glove assemblies provided herein include a tray responsive to the number of gloves in the dispenser, movable in a vertical direction within the disposable dispenser towards the dispenser opening with its movement facilitated by a telescoping piston or other biasing members, such as a conical spring. The dispenser may be removed from the holder and a new dispenser engaged to the holder. Aspects of the present disclosure also include a disposable dispenser having a biasing member urging a tray in a vertical direction in response to the number of gloves in the dispenser."

U.S. Published Patent Application No. 20110062179 that was published by Stollery discloses "The present invention relates to the dispensing of gloves from a dispenser. The dispenser (1) comprises a container (2) and a plurality of disposable gloves (22). The container (2) has a plurality of faces (3, 4, 5), and each glove (22) has a cuff portion (36) and a finger portion (34), the cuff portion having a cuff (40) and the gloves being stacked one on another with the cuffs of the gloves being aligned on one side (42) of the stack (20) of gloves held within the container (2). The container (2) has in use a dispensing aperture (24) in at least one face (3, 5) of the container through which gloves (22) can be dispensed. The gloves (22) are oriented in the container (2) so that the gloves are positioned for dispensing cuff-first through the aperture (24), and the finger portion (34) of each glove (22) is folded back against the cuff portion (36) of the same glove to protect the finger portion from user contact and contamination during dispensing of the glove. The cuff portion has a cuff opening for receiving a user's hand, the cuff opening facing outwards with respect to the dispensing aperture."

However, these solutions still do not solve all of the problems associated with a safe method for dispensing protective gloves without contaminating the protective gloves. Thus, it is desirable to solve some of the problems associated with protective glove dispensers.

SUMMARY OF THE INVENTION

In accordance with preferred embodiments of the present invention, some of the problems associated with dispensing protective gloves are overcome. A sanitary automatic glove dispensing apparatus and method of use is presented.

The automatic sanitary glove dispensing apparatus, based on one or more received dispensing events, dispenses pairs of connected protective gloves stored on a roll of protective gloves as a pair of protective gloves and overlapped in a pre-determined pattern, by cuff ends so finger ends of the protective gloves are not contaminated during dispensing. After a pair of protective gloves are dispensed by both cuff ends, no additional protective gloves are exposed from the apparatus until another protective glove dispensing event is received, thereby protecting remaining protective gloves in the apparatus from contamination by noroviruses and bacteria from a surrounding external environment and from other users of the apparatus.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 10 is a block diagram illustrating the sanitary automatic glove dispensing apparatus of FIG. 1 with an LCD display screen and an audio speaker;

FIGS. 14A and 14B are a flow diagram illustrating a method for automatically dispensing a pair of protective gloves by cuff ends with the sanitary automatic glove dispensing apparatus of FIG. 1;

FIGS. 15A and 15B are a flow diagram illustrating a method for automatically dispensing a pair of protective gloves with the sanitary automatic glove dispensing apparatus of FIG. 1;

FIG. 16 is a flow diagram illustrating a method for automatically dispensing a pair of protective gloves with the sanitary automatic glove dispensing apparatus of FIG. 1;

FIG. 17 is a flow diagram illustrating a method for automatically dispensing a pair of protective gloves with the sanitary automatic glove dispensing apparatus of FIG. 1;

DETAILED DESCRIPTION OF PREFERRED EMBODIMENTS

An important element of hand hygiene practice is the correct application of single use, non-sterile, or sterile protective gloves. The correct application can reduce the spread of pathogenic organisms. Unfortunately many studies have demonstrated the presence of bacteria and viruses on unused gloves in open boxes, non-automated and automated glove dispensers which are commonly used in all settings where non-sterile and sterile protective gloves are worn. The methods of boxing, dispensing and retrieving the protective gloves are responsible for the contamination of the glove surfaces including the finger ends and other surfaces of the gloves and lead to disease and infection outbreaks.

The World Health Organization (WHO) guidelines reflect current best practices for donning non-sterile gloves. The "*Glove Use Information Leaflet*," World Health Organization, August 2009, is incorporated herein by reference. For example, here is the WHO procedure for donning non-sterile examination gloves from a box of gloves: "(1) take a first single glove of out a box touching only a restricted surface of the first glove including a top edge of a top edge of a first cuff of the glove; (2) don the first glove pulling the glove on the hand via the top edge of the cuff with the other hand; (3) take a second single glove by a top edge of a second cuff with the ungloved hand; (4) to avoid touching skin of hand or forearm of the ungloved hand, turn the external surface of the second glove to be donned on folded fingers of the gloved hand, thus permitting the second hand to be gloved;

and (6) once gloved, the finger ends of the gloved hands should not touch any surface or thing not defined for use of the protective gloves."

Thus, it is desirable to provide a method and apparatus to dispense protective gloves by cuff ends without contaminating surfaces of the protective gloves and without contaminating any other remaining gloves and/or without exposing any remaining protective gloves to a surrounding environment.

Exemplary Sanitary Automatic Protective Glove Dispensing Apparatus

Figure 1:
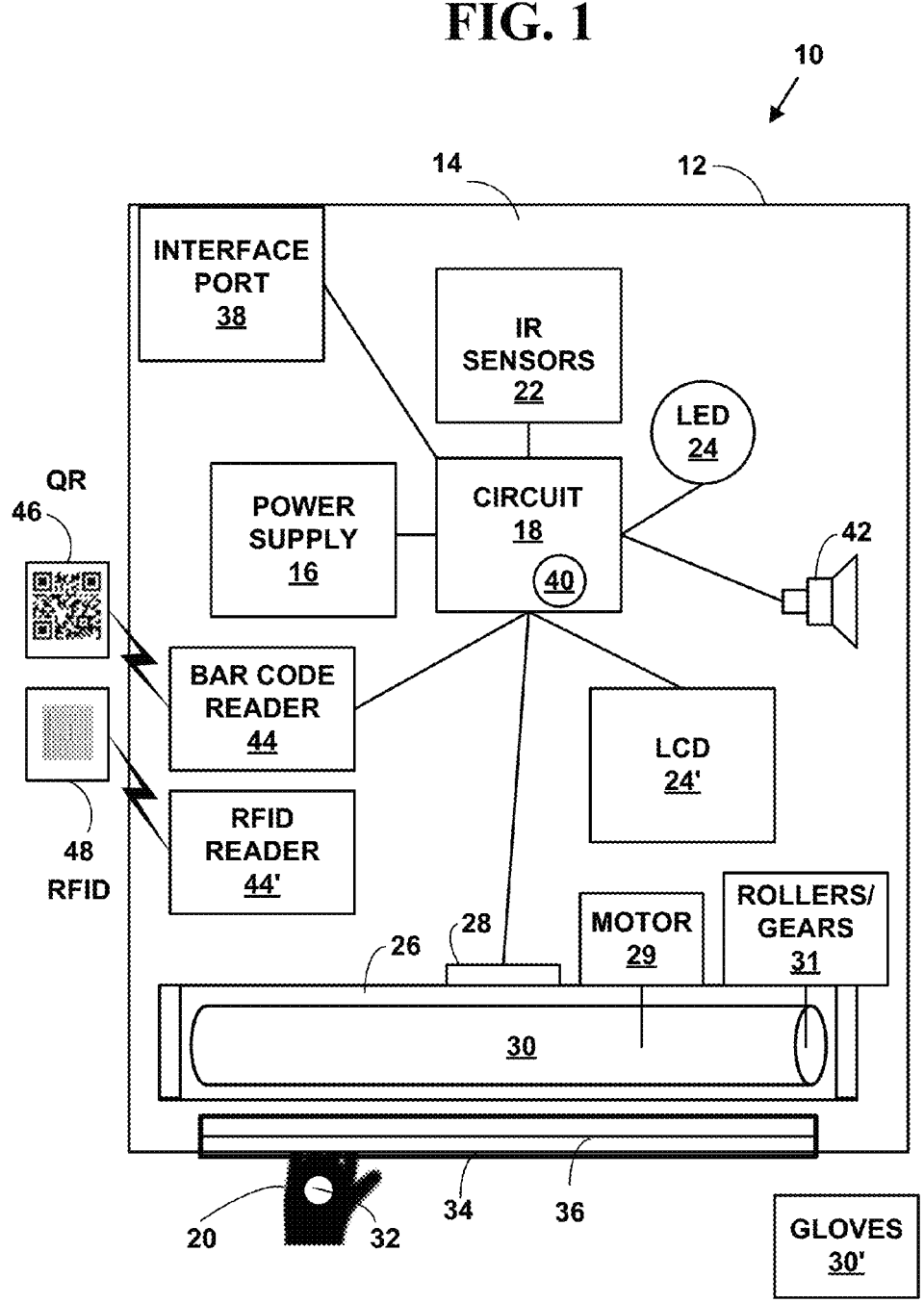
FIG. 1 is a block diagram illustrating a sanitary automatic glove dispensing apparatus.

FIG. 1 is a block diagram 10 illustrating a sanitary, automatic protective glove dispensing apparatus 12 (components not drawn to scale). The apparatus 12 includes a protective case 14 including: one or more power supplies 16; an electronic circuit 18 including one or more processors connected to the one or more power supplies 16 configured for automatically dispensing a plural pairs of protective gloves 20, 20' by cuff ends 88 (FIG. 7); one or more infrared (IR) sensors 22 connected to the electronic circuit 18 for detecting with a detection field of a pre-determined detection size and a pre-determined detection orientation (FIG. 3), one or more glove dispensing events to dispense a pair of protective gloves 20, 20' by the cuff ends 88 from the plural pairs of protective gloves and for activating one or more light emitting diodes (LEDs) 24; the one or more LEDs 24 connected to an electronic circuit for visually indicating one or more operational states of the apparatus 12; a glove roll rack 26 for engaging and dis-engaging one or more rolls of protective gloves 30 and including a rack circuit 28 connected to the electronic circuit 18 for moving the roll of protective gloves 30 a pre-determined distance with an electronic motor 29 to dispense the plural pairs of protective gloves 20, 20' by the cuff ends 88 in response to one or more electrical signals from the electronic circuit 18 and for dispensing a pair of protective gloves 20, 20' completely by the cuff ends 88 without exposing another pair of protective gloves 20, 20' until additional one or more electrical signals are received from the electronic circuit 18 in response to another dispensing event detected by the one or more IR sensors 22, thereby protecting the remaining pairs of protective gloves 20, 20' on the one or more rolls of protective gloves 30 from contamination from an external environment; the electronic motor 29 connected to one or more power supplies 16 and the rack circuit 28 for moving the one or more rolls of protective gloves 30 the pre-determined distance; the one or more rolls of protective gloves 30 including plural individual protective gloves stored as pairs of protective gloves 20, 20', the pairs of protective gloves 20, 20' connected with a pre-determined connector 32, wherein each of the individual gloves 20, 20' in the pair of protective gloves 20, 20' is rolled on the one or more rolls of protective gloves 30 in a pre-determined overlap pattern 92 a pre-determined space 97 apart, wherein a pair of protective gloves 20, 20' from the plural protective gloves 20, 20' is dispensed from the one or more rolls of protective gloves 30 by the cuff ends 88 avoiding contaminating the finger surfaces 86 by a user 74 of the protective gloves 20, 20' during dispensing; a dispensing slot 34 in a surface of the protective case 14 for dispensing the pair of protective gloves 20, 20' by the cuff ends 88 of the individual protective gloves 20, 20' in the pair of protective gloves 20, 20'; and a dispensing membrane 36 integral to the dispensing slot 34 for protecting the pair of gloves 20, 20' during dispensing and for protecting the plural protective gloves 20, 20' remaining on the one or more rolls of protective gloves 30 from contamination from an external environment.

However, the present invention is not limited to the components described and more, fewer or other components can be used to practice the invention.

Figure 2:
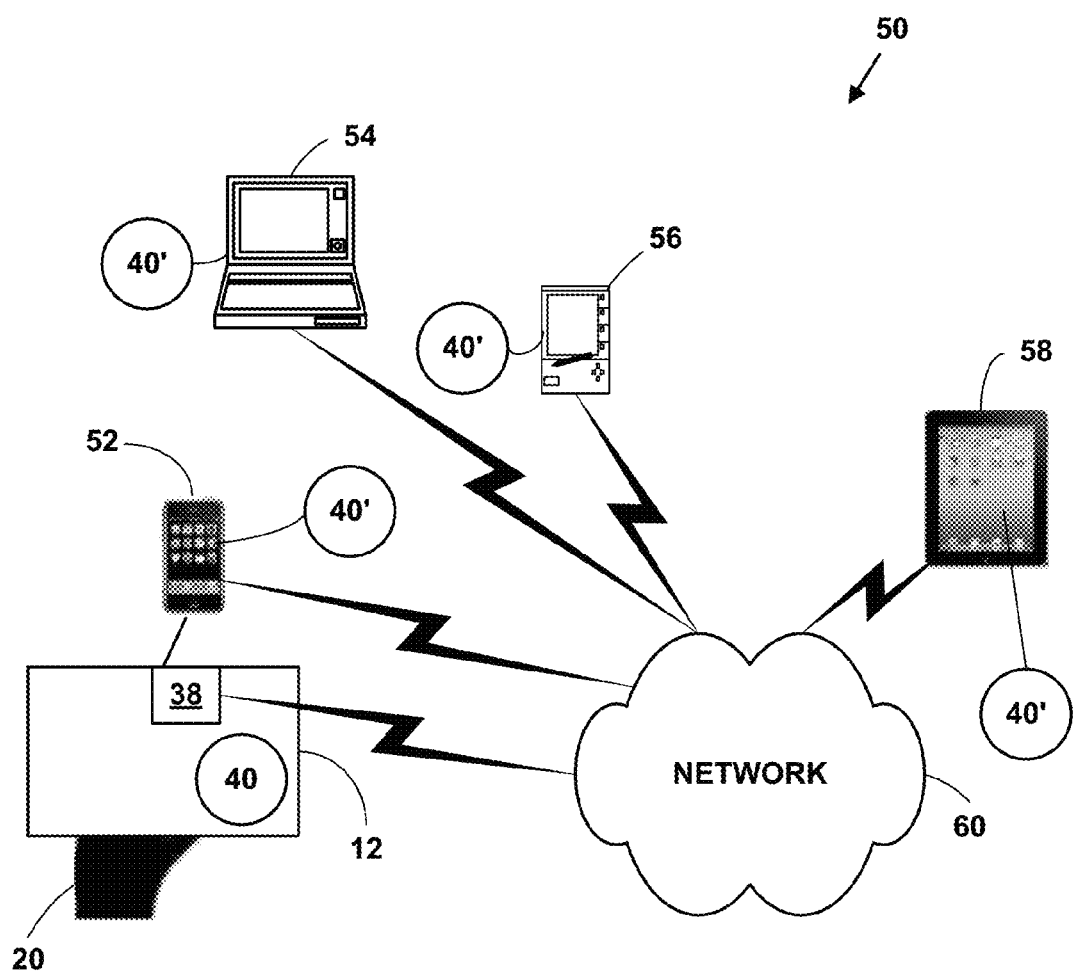
FIG. 2 is a block diagram illustrating an exemplary network sanitary automatic glove dispensing system.

FIG. 2 is a block diagram 50 illustrating an exemplary network sanitary automatic glove dispensing system.

Apparatus 12 communicates via interface port 38 with network devices 52, 54, 56, 58 via communications network 60.

The automatic glove dispensing apparatus 12 is described with an exemplary embodiment. However, the present invention is not limited to this exemplary embodiment and other embodiments can be used to practice the invention.

In such an exemplary embodiment, the protective case 14 includes, metal, plastic, rubber and/or composite materials. However, the present invention is not limited to this exemplary embodiment and other embodiments can be used to practice the invention.

In one embodiment, the protective case 14, if used in a medical, dental, veterinarian and/or facility, etc., includes one or more antimicrobial surfaces. In one embodiment, the one or more surfaces of the protective case 14 are made of an antimicrobial plastic. Antimicrobial plastics were invented in about 2008. There are several companies that have antimicrobial plastic products out on the market such as MICROBAN. However, the present invention is not limited to this exemplary embodiment and other embodiments can be used to practice the invention.

The one or more power supplies 16 include a Direct Current (DC) and/or an Alternating Current (AC) power supply 16 and/or a combination thereof.

The one or more power supplies 16 include an electronic device that supplies electric power to an electrical load. The primary function of a power supply is to convert one form of electrical energy to another and, as a result, power supplies are sometimes referred to as electric power converters. Some power supplies are discrete, stand-alone devices, whereas others are built into larger devices along with their loads. Every power supply must obtain the energy it supplies to its load, as well as any energy it consumes while performing that task, from an energy source. All power supplies have a power input, which connects to the energy source, and a power output that connects to the load. In many power supplies the power input and output consist of electrical connectors.

In one embodiment, the one or more power supplies 16 include a DC power supply. A DC power supply 16 is one that supplies a voltage of fixed polarity (either positive or negative) to its load. Depending on its design, a DC power supply may be powered from a DC source or from an AC source. DC power supplies, include, but are not limited to, batteries, thermocouples, solar cells, capacitors, etc.

A "battery" is a device consisting of one or more electrochemical cells that convert stored chemical energy into electrical energy.

A "thermocouple" is a temperature-measuring device consisting of two dissimilar conductors that contact each other at one or more spots. It produces a voltage when the temperature of one of the spots differs from the reference temperature at other parts of the circuit.

A "solar cell" (also called a photovoltaic cell) is an electrical device that converts the energy of light directly into electricity by the photovoltaic effect.

A "capacitor" (originally known as a condenser) is a passive two-terminal electrical component used to store energy electrostatically in an electric field. For example, the mechanical motion that is used to dispense the pair of protective gloves 20, 20' can be used to re-charge the capacitor as a power supply 16.

In another embodiment, the one or more power supplies 16 include an AC power supply.

An AC power supply 16 typically takes the voltage from a main power source, (e.g., 110 volt wall socket, etc.) and lowers it to a desired voltage.

In another embodiment, the one or more power supplies include both a DC and an AC power supply.

In another embodiment, the one or more power supplies 16 include a switched-mode power supply (SMPS). In an SMPS, the AC mains input is directly rectified and then filtered to obtain a desired DC voltage. The resulting DC voltage is then switched on and off at a high frequency by electronic switching circuitry, thus producing an AC current that will pass through a high-frequency transformer or inductor. Switching occurs at a very high frequency (e.g., typically 10 kHz to 1 MHz), thereby enabling the use of transformers and filter capacitors that are much smaller, lighter, and less expensive than those found in linear power supplies operating at mains frequency. After the inductor or transformer secondary, the high frequency AC is rectified and filtered to produce the desired DC output voltage.

However, the present invention is not limited to the power supplies 16 discussed and other types of power supplies and/or other combinations of AC and DC power can be used to practice the invention.

The electronic circuit 18 is connected to the one or more power supplies 16, the circuit 18 being configured for automatically completely dispensing a pair of protective gloves 20, 20' by cuff ends 88, 88' without exposing additional pairs of protective gloves 20, 20' until additional glove dispensing events are detected by controlling the other components of the apparatus 12.

In one embodiment, the electronic circuit 18 includes an integrated circuit (IC) or monolithic integrated circuit (also referred to as an IC, a chip, or a microchip). An integrated circuit is a set of electronic circuits on one small plate ("chip") of semiconductor material, normally silicon. However, the present invention is not limited to such an embodiment and other types of circuits can be used to practice the invention.

The electronic circuit 18 includes an operating environment for the present invention comprising a processing system with one or more high speed Central Processing Unit(s) ("CPU") or other types of processors, a non-transitory memory and an interface port 38, including but not limited to a Universal Serial Bus (USB) interface port, wireless network interface port, wired network interface port, and/or other types of interface ports. However, the present invention is not limited to this embodiment and can be practiced with and/or without an interface port 38.

Wireless Interfaces

In one embodiment of the present invention, the wireless interface port 38 on the apparatus 12 and wireless interfaces on network devices 52-58 with one or more processors (FIG. 2) include but are not limited to, 3G and/or 4G, IEEE 802.11a, 802.11b, 802.11g, 802.11n, 802.15.4 (ZigBee), "Wireless Fidelity" (Wi-Fi), "Worldwide Interoperability for Microwave Access" (WiMAX), ETSI High Performance Radio Metropolitan Area Network (HIPERMAN) or "RF Home" wireless interfaces. In another embodiment of the present invention, the wireless sensor device may include an integral or separate Bluetooth and/or infra data association (IrDA) module for wireless Bluetooth or wireless infrared communications. However, the present invention is not limited to such an embodiment and other 802.11xx and other types of wireless interfaces can also be used.

802.11b is a short-range wireless network standard. The IEEE 802.11b standard defines wireless interfaces that provide up to 11 Mbps wireless data transmission to and from wireless devices over short ranges. 802.11a is an extension of the 802.11b and can deliver speeds up to 54 M bps. 802.11g deliver speeds on par with 802.11a. However, other 802.11XX interfaces can also be used and the present invention is not limited to the 802.11 protocols defined. The IEEE 802.11a, 802.11b and 802.11g standards are incorporated herein by reference.

Wi-Fi is a type of 802.11xx interface, whether 802.11b, 802.11a, dual-band, etc. Wi-Fi devices include RF interfaces such as 2.4 GHz for 802.11b or 802.11g and 5 GHz for 802.11a.

802.15.4 (Zigbee) is low data rate network standard used for mesh network and non-mesh network devices such as sensors, interactive toys, smart badges, remote controls, and home automation. The 802.15.4 standard provides data rates of 250 kbps, 40 kbps, and 20 kbps., two addressing modes; 16-bit short and 64-bit IEEE addressing, support for critical latency devices, such as joysticks, Carrier Sense Multiple Access/Collision Avoidance, (CSMA-CA) channel access, automatic network establishment by a coordinator, fully handshaked protocol for transfer reliability, power management to ensure low power consumption for multi-month to multi-year battery usage and up to 16 channels in the 2.4 GHz Industrial, Scientific and Medical (ISM) band (Worldwide), 10 channels in the 915 MHz (US) and one channel in the 868 MHz band (Europe). The IEEE 802.15.4-2003 standard is incorporated herein by reference.

WiMAX is an industry trade organization formed by leading communications component and equipment companies to promote and certify compatibility and interoperability of broadband wireless access equipment that conforms to the IEEE 802.16XX and ETSI HIPERMAN. HIPERMAN is the European standard for metropolitan area networks (MAN).

The IEEE 802.16a and 802.16g standards are wireless MAN technology standards that provide a wireless alternative to cable, DSL and T1/E1 for last mile broadband access. It is also used as complimentary technology to connect IEEE 802.11XX hot spots to the Internet.

The IEEE 802.16a standard for 2-11 GHz is a wireless MAN technology that provides broadband wireless connectivity to fixed, portable and nomadic devices. It provides up to 50-kilometers of service area range, allows users to get broadband connectivity without needing direct line of sight with the base station, and provides total data rates of up to 280 Mbps per base station, which is enough bandwidth to simultaneously support hundreds of businesses with T1/E1-type connectivity and thousands of homes with DSL-type connectivity with a single base station. The IEEE 802.16g provides up to 100 Mbps.

The IEEE 802.16e standard is an extension to the approved IEEE 802.16/16a/16g standard. The purpose of 802.16e is to add limited mobility to the current standard which is designed for fixed operation.

The ESTI HIPERMAN standard is an interoperable broadband fixed wireless access standard for systems operating at radio frequencies between 2 GHz and 11 GHz.

The IEEE 802.16a, 802.16e and 802.16g standards are incorporated herein by reference. WiMAX can be used to provide a WLP.

The ETSI HIPERMAN standards TR 101 031, TR 101 475, TR 101 493-1 through TR 101 493-3, TR 101 761-1 through TR 101 761-4, TR 101 762, TR 101 763-1 through TR 101 763-3 and TR 101 957 are incorporated herein by reference. ETSI HIPERMAN can be used to provide a WLP.

In one embodiment, the apparatus 12 and network devices 52-58 include wired and wireless interfaces comprising Network Interface Cards (NIC)s with "4G" components. "4G" refers to the fourth generation of wireless communications standards and speeds of 100 megabits/second to gigabits/second or more. 4G includes peak speed requirements for 4G service at least 100 Mbit/s for high mobility communication (e.g., trains, vehicles, etc.) and 1 Gbit/s for low mobility communication (e.g., pedestrians and stationary users, etc.).

The 4G and 5G technologies are a successor to 3G and 2G standards. The nomenclature of the generations generally refers to a change in the fundamental nature of the service. The first was the move from analogue (1G) to digital (2G) transmission. This was followed by multi-media support, spread spectrum transmission and at least 200 kbits/second (3G). The 4G NICs include IP packet-switched NICs, wired and wireless ultra-broadband (i.e., gigabit speed) access NICs, Worldwide Interoperability for Microwave Access (WiMAX) NICs WiMAX Long Term Evolution (LTE) and/ or multi-carrier transmission NICs. However, the present invention is not limited to this embodiment and 1G, 2G and 3G and/or any combination thereof, with or with 4G and/or 5G NICs can be used to practice the invention.

In one embodiment of the invention, the WiMAX interfaces includes WiMAX 4G or 5G Long Term Evolution (LTE) interfaces. The ITU announced in December 2010 that WiMAX and LTE are 4G technologies. One of the benefits of 4G LTE is the ability to take advantage of advanced topology networks including those on communications networks 60 such as optimized heterogeneous networks with a mix of macrocells with low power nodes such as picocells, femtocells and new relay nodes. LTE further improves the capacity and coverage, and helps ensure user fairness. 4G LTE also introduces multicarrier technologies for ultra-wide bandwidth use, up to 100 MHz of spectrum supporting very high data rates.

In one embodiment, of the invention, the wireless interfaces also include wireless personal area network (WPAN) interfaces. As is known in the art, a WPAN is a personal area network for interconnecting devices centered around an individual person's devices in which the connections are wireless. A WPAN interconnects all the ordinary computing and communicating devices that a person has on their desk (e.g. computer, etc.) or carries with them (e.g., PDA, mobile phone, smart phone, table computer two-way pager, etc.)

A key concept in WPAN technology is known as "plugging in." In the ideal scenario, when any two WPAN-equipped devices come into close proximity (within several meters and/or feet of each other) or within a few miles and/or kilometers of a central server (not illustrated), they can communicate via wireless communications as if connected by a cable. WPAN devices can also lock out other devices selectively, preventing needless interference or unauthorized access to secure information. Zigbee is one wireless protocol used on WPAN networks such as communications network 60.

In one embodiment, the apparatus 12 accepts Radio Frequency Identification/Identifier (RFID) signals on an RFID reader 44'.

"Radio Frequency Identification/Identifier (RFID)" is used with apparatus 12 to detect and record which user 74 requests dispensing of a pair of protective gloves 20, 20' and other information such a glove size, employee name, employee identifier, etc.

RFID is the wireless use of electromagnetic fields to transfer data, for the purposes of automatically identifying and tracking tags attached to objects such as identification badge/card or other card 84.

An "RFID tag" 48 is an object that can be applied to or incorporated into a product used by a user 74 (FIG. 4) for the purpose of identification and/or tracking using RF signals.

An "RFID sensor" 48' is a device that measures a physical quantity and converts it into an RF signal which can be read by an observer or by an instrument.

The RFID tags 48 include unique electronically stored information. Some tags 48 are powered by electromagnetic induction from magnetic fields produced near an RFID reader 44'. Some other types of RFID tags 48 collect energy from the interrogating radio waves and act as a passive transponder. Other types of RFID tags 48 have a local power source such as a battery and may operate at hundreds of meters from the RFID reader 44'. Unlike a barcode 46, the RFID tag 48 does not necessarily need to be within line of sight of the RFID reader 44' and may be embedded in the tracked object (e.g., identification card 84 (FIG. 6), etc.). RFID is one method for Automatic Identification and Data Capture (AIDC).

In one embodiment, the apparatus 12 and network devices 52-58 communicate with each other and other network devices near field communications (NFC) and/or machine-to-machine (M2M) communications.

"Near field communication (NFC)" is a set of standards for smartphones and similar network devices to establish radio communication with each other by touching them together or bringing them into close proximity, usually no more than a few centimeters. Present applications include contactless transactions, data exchange, and simplified setup of more complex communications such as Wi-Fi. Communication is also possible between an NFC device and an unpowered NFC chip, called a "tag" including radio frequency identifier (RFID) tags and/or sensor.

NFC standards cover communications protocols and data exchange formats, and are based on existing radio-frequency identification (RFID) standards including ISO/IEC 14443 and FeliCa. These standards include ISO/IEC 1809 and those defined by the NFC Forum, all of which are incorporated by reference.

"Machine to machine (M2M)" refers to technologies that allow both wireless and wired systems to communicate with other devices of the same ability. M2M uses a device to capture an event (such as option purchase, etc.), which is relayed through a network (wireless, wired cloud, etc.) to an application (software program), that translates the captured event into meaningful information. Such communication was originally accomplished by having a remote network of machines relay information back to a central hub for analysis, which would then be rerouted into a system like a personal computer.

However, modern M2M communication has expanded beyond a one-to-one connection and changed into a system of networks that transmits data many-to-one and many-to-many to plural different types of devices and appliances. The expansion of IP networks across the world has made it far easier for M2M communication to take place and has lessened the amount of power and time necessary for information to be communicated between machines.

However, the present invention is not limited to such wireless interfaces and wireless networks and more, fewer and/or other wireless interfaces can be used to practice the invention.

Wired Interfaces

In one embodiment of the present invention, the interface port 38 of the apparatus 12 and wired interfaces of the network devices 52-58 includes wired interfaces and corresponding networking protocols for wired connections to the Public Switched Telephone Network (PSTN) and/or a cable television network (CATV) and/or satellite television networks (SATV) and/or three-dimensional television (3DTV), including HDTV that connect the apparatus 12 and network devices 52-58 via one or more twisted pairs of copper wires, digital subscriber lines (e.g. DSL, ADSL, VDSL, etc.) coaxial cable, fiber optic cable, other connection media or other connection interfaces. The PSTN is any public switched telephone network provided by AT&T, GTE, Sprint, MCI, SBC, Verizon and others. The CATV is any cable television network provided by Comcast, Time Warner, etc. However, the present invention is not limited to such wired interfaces and more, fewer and/or other wired interfaces can be used to practice the invention.

Processors

In accordance with the practices of persons skilled in the art of computer programming, the apparatus 12 of present invention is described below with reference to acts and symbolic representations of operations or instructions that are performed by the processing system, unless indicated otherwise. Such acts and operations or instructions are referred to as being "computer-executed," "CPU executed" or "processor executed."

It will be appreciated that acts and symbolically represented operations or instructions include the manipulation of electrical signals by the CPU. An electrical system represents data bits which cause a resulting transformation or reduction of the electrical signals, and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to the data bits.

The data bits may also be maintained on a non-transitory computer readable medium including magnetic disks, optical disks, organic memory, and any other volatile (e.g., Random Access Memory ("RAM")) or non-volatile (e.g., Read-Only Memory ("ROM")) mass storage system readable by the CPU.

Returning to FIG. 1, the one or more infrared (IR) sensors 22 are connected to the electronic circuit 18 for detecting plural glove dispensing events.

"Infrared (IR)" is electromagnetic radiation with longer wavelengths than those of visible light, extending from the nominal red edge of the visible spectrum at 700 nanometers (nm) to 1 mm. This range of wavelengths corresponds to a frequency range of approximately 430 THz down to 300 GHz. Most of the thermal radiation emitted by objects, including humans, near room temperature is infrared.

Figure 3:
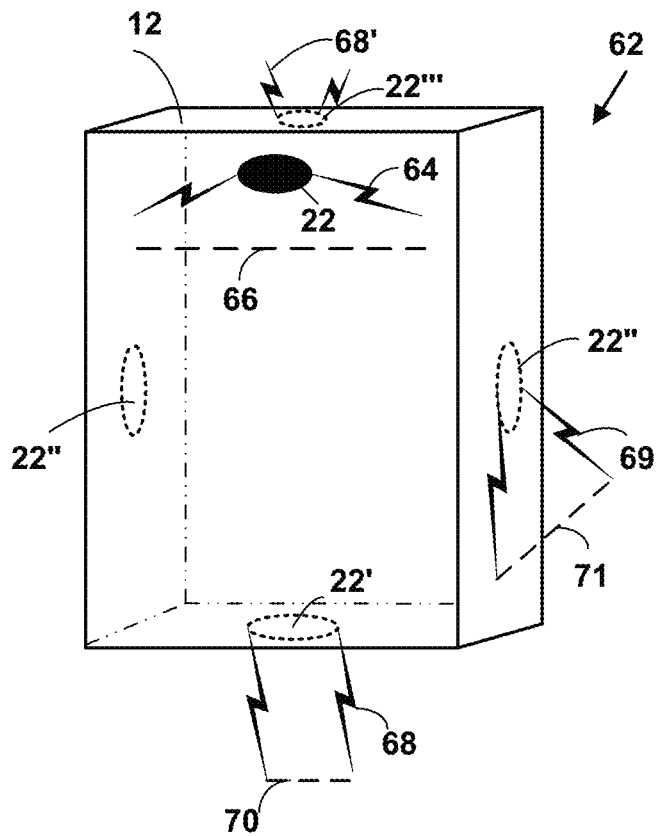
FIG. 3 is a block diagram illustrating the sanitary automatic glove dispensing apparatus of FIG. 1 with a first, second and third IR detection field.

FIG. 3 is a block diagram 62 illustrating the sanitary automatic glove dispensing apparatus of FIG. 1 with a first, second and third IR detection field.

Figure 4:
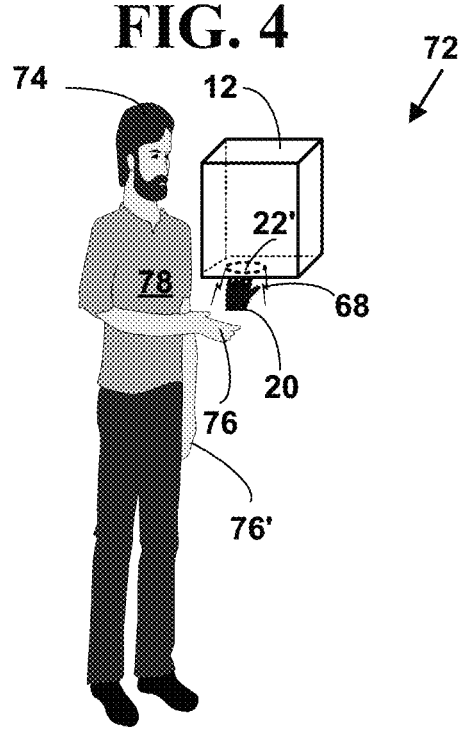
FIG. 4 is a block diagram illustrating a dispensing event generated by a hand of a user with the sanitary automatic glove dispensing apparatus of FIG. 1.

FIG. 4 is a block diagram 72 illustrating a dispensing event generated by a hand of a user with the sanitary automatic glove dispensing apparatus of FIG. 1.

Figure 5:
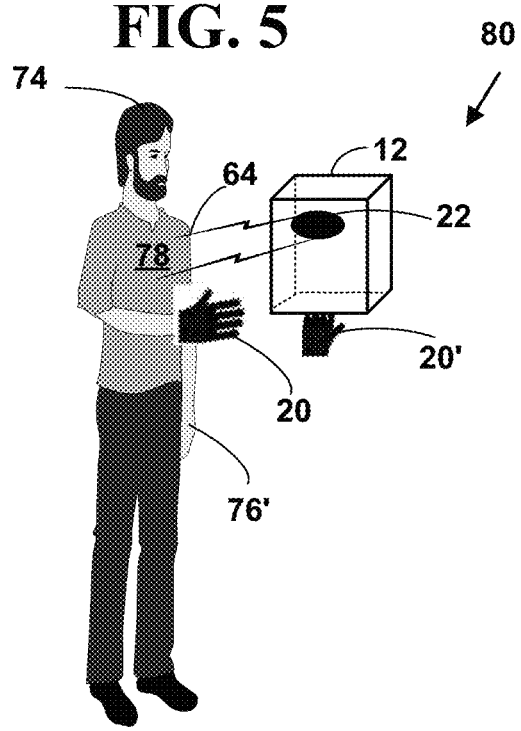
FIG. 5 is a block diagram illustrating a dispensing event generated by a torso of a user with the sanitary automatic glove dispensing apparatus of FIG. 1.

FIG. 5 is a block diagram 80 illustrating a dispensing event generated by a torso of a user with the sanitary automatic glove dispensing apparatus of FIG. 1.

Figure 6:
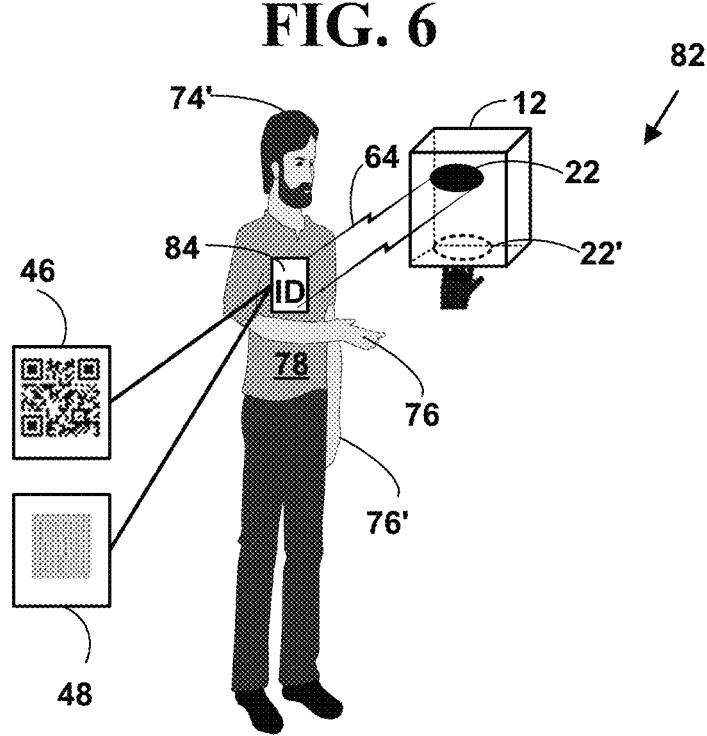
FIG. 6 is a block diagram illustrating a dispensing event generated by a bar code and/or RFID signal for the sanitary automatic glove dispensing apparatus of FIG. 1.

FIG. 6 is a block diagram 82 illustrating a dispensing event generated by a bar code 46 and/or RFID signal 48 for the sanitary automatic glove dispensing apparatus of FIG. 1.

The human figures 74 in FIGS. 5 and 6 are not rotated to a correct orientation which should be immediately in front of the apparatus 12. The human figures 74 were placed in this orientation for simplicity to more clearly illustrate the details of the invention with the drawings.

In one embodiment, the glove dispensing event includes detecting a portion of a user 74 including a hand 76 of the user 74 (FIG. 4). In such an embodiment, the glove detecting event includes the hand 76 of the user activating the one or more IR sensors 22 with a first hand, standing in front of the apparatus 12 by placing the first hand underneath the apparatus 12. In such an embodiment, the one or more IR sensors 22 are configured with a detection field with a downward facing orientation 68 and specifically sized and shaped 70 to detect an average sized human hand 76. However, the present invention is not limited to such embodiments and other first dispensing events can be used to practice the invention.

In another embodiment, the glove dispensing event includes the portion of the user using their body torso 78 by standing in front of the apparatus 12 to trigger the one or IR sensors 22' into the glove dispensing event (FIG. 5). In such an embodiment, the one or more IR sensors 22 are configured with a detection field with a forward facing orientation 64 and specifically sized and shaped 66 to detect a human torso 78. However, the present invention is not limited to such embodiments and other first dispensing events can be used to practice the invention.

In another embodiment, the glove dispensing event includes detecting a bar code 46 and/or and RFID signal 48 from an identification card 82 and/or other card 82 on the bar code 44 and or RFID reader 44', from a bar code 46 or RFID tag 48 supplied by the user. In such an embodiment, the bar code/RFID signals 46, 48 sent to the electronic circuit 18 creates the glove dispensing event.

For example, in FIG. 1, an actual QR bar code 46 when decoded includes the text "Ilya Ray, size medium" for dispensing a pair of protective gloves 20, 20' of size medium. However, the present invention is not limited to such embodiments and/or types of bar codes and other 2D and/or 3D bar codes can be used to practice the invention.

A "barcode" 46 is an optical machine-readable representation of data, which shows data about the object to which it attaches. Originally, barcodes represented data by varying the widths and spacing of parallel lines, and may be referred to as linear or 1 dimensional (1D). Later they evolved into rectangles, dots, hexagons and other geometric patterns in 2 dimensions (2D). Although 2D systems use a variety of symbols, they are generally referred to as barcodes as well. Barcodes originally were scanned by special-optical scanners called barcode readers, scanners and interpretive software.

Table 1 illustrates exemplary linear barcodes, the standards of all of which are incorporated by reference. However, the present invention is not limited to the exemplary linear barcodes listed in Table 1, and more, fewer and other linear barcodes can also be used to practice the invention.

TABLE 1

Linear Bar Codes
U.P.C.
Codabar

TABLE 1-continued

Code 25 - Non-interleaved 2 of 5
Code 25 - Interleaved 2 of 5
Code 39
Code 93
Code 128
Code 128A
Code 128B
Code 128C
Code 11
CPC Binary
DUN 14
EAN 2
EAN 5
EAN 8, EAN 13
Facing Identification Mark
GS1-128 (formerly known as UCC/EAN-128), incorrectly referenced as EAN 128 and UCC 128
GS1 DataBar, formerly Reduced Space Symbology (RSS)
HIBC (HIBCC Health Industry Bar Code)
ITF-14
Latent image barcode
Pharmacode
Plessey
PLANET
POSTNET
Intelligent Mail barcode
MSI
PostBar
RM4SCC/KIX
JAN
Telepen Table 2 illustrates exemplary matrix (2D) barcodes, the standards of all of which are incorporated by reference. However, the present invention is not limited to the exemplary matrix barcodes listed in Table 2, and more, fewer and other matrix barcodes can also be used to practice the invention.

TABLE 2

Matrix Bar Codes
3-DI
ArrayTag
Aztec Code
Small Aztec Code
Chromatic Alphabet
Codablock
Code 1
Code 16K
Code 49
ColorCode
Compact Matrix Code
CP Code
CyberCode
d-touch
DataGlyphs
Datamatrix
Datastrip Code
Dot Code A
EZcode
Grid Matrix Code
High Capacity Color Barcode
HueCode
INTACTA.CODE
InterCode
JAGTAG
Lorem ipsum
MaxiCode
mCode
MiniCode
MicroPDF417
MMCC
Nintendo e-Reader#Dot code
Optar
PaperDisk
PDF417

TABLE 2-continued

PDMark
QR Code
QuickMark Code
SmartCode
Snowflake Code
ShotCode
SPARQCode
SuperCod
Trillcode
UltraCode
UnisCode
VeriCode, VSCode
WaterCode In one specific embodiment, the application 40 interacts with a bar code reader 44 application. However, the present invention is not limited to a bar code reader application and other applications can also be used to practice the invention.

In one specific exemplary embodiment, a QR bar code 46 (FIGS. 1 and 6) is used. However, the present invention is not limited to QR codes and other types of bar codes can also be used to practice the invention.

In one specific exemplary embodiment, the bar code 46 and/or RFID signal 48 includes encoded instructions as to which size and/or type of protective gloves to dispense. For example, a first bar code for a surgeon includes a first bar code 46 and/or RFID signal 48 to dispense a pair of size large surgical gloves which are sterile and a second bar code includes a second bar code to dispense a pair of size large exam gloves which are not sterile. However, the present invention is not limited to such embodiment and other embodiments can be used to practice the invention.

In one specific embodiment, the bar code 46 is included on an identification badge/card 84 and/or other type of card 84. (FIG. 6). However, the present invention is not limited to such embodiment and other embodiments can be used to practice the invention.

In one exemplary embodiment, the one or more IR sensors 22 include, but are not limited to, an NFT-7345 infrared charged couple device (CCD) scanner or similar IR sensor 22, sold by OPTICON, Inc. and other companies. This IR sensor is a fixed-position scanner using infrared light to scan barcodes 46 at scan rates of 200 scans per second. The one or more IR sensors 22 described are exemplary only and the present invention is not limited to the IR sensor mentioned and other IR sensors, sold by other companies can be used to practice the invention.

In one embodiment, the one or more IR sensors 22 include a passive infrared sensor (PIR sensor). A PIR sensor is an electronic sensor that measures infrared (IR) light radiating from objects in its field of view. All objects with a temperature above absolute zero emit heat energy in the form of radiation. Usually this radiation is invisible to the human eye because it radiates at infrared wavelengths, but it can be detected by electronic devices designed for such a purpose. However, the present invention is not limited to passive IR sensors and other types of IR sensors and other types of sensors can be used to practice the invention.

The term "passive" in this instance refers to the fact that PIR devices do not generate or radiate any energy for detection purposes. They work entirely by detecting the energy given off by other objects. It is important to note that PIR sensors don't detect or measure "heat" per se; instead they detect the Infrared radiation emitted from an object which is different from but often associated/correlated with the object's temperature.

In one embodiment, the IR sensor 22 includes a solid state sensor or set of sensors, made from pyroelectric materials—materials which generate energy when exposed to heat. Typically, the sensors are approximately ¼ inch square (40 mm$^2$) and take the form of a thin film. Materials commonly used in PIR sensors include gallium nitride (GaN), caesium nitrate (CsNO$_3$), polyvinyl fluorides, derivatives of phenylpyridine, and cobalt phthalocyanine. The sensor is often manufactured as part of an integrated circuit.

In one embodiment, the one or more IR sensors 22 (FIG. 3) include a first detection field 64 of a first size 66 of a first "forward" facing orientation on the apparatus 12 to detect a user 74 standing in front of apparatus 12 (FIG. 5) desiring to dispense the protective gloves 20. In such an embodiment, the first detection field 64 is of size 66 of about four to six inches (about ten to fifteen centimeters) and includes the first detection field 64 that has been determined experimentally to optimally detect a user 74 standing directly in front of the apparatus 12. Detection fields of other sizes (i.e., are too big, etc.) and other orientations may falsely detect a user 74 walking by the apparatus or may not detect a user 74 at all (i.e., are too small, short, etc.). However, the present invention is not limited to such an embodiment, and other detection field sizes, and other detection orientations can be used to practice the invention.

In one embodiment, the one or more IR sensors 22' (FIG. 3) include a second detection field 68 of a second size 70 of a second "downward" facing orientation on the apparatus 12 to detect the hand 76 of the user 74 (FIG. 4) desiring to dispense the protective gloves 20. In such an embodiment, the second detection field 68 is of size 70 of about two to four inches (about four to ten centimeters) and includes the second detection field 68 that has been determined experimentally to optimally detect a hand 76 of the user 74 placing it directly under the one or more IR sensors 22' of the apparatus 12. Detection fields of other sizes (i.e., are too small, etc.) and other orientations may falsely detect another portion of the user 74 walking by the apparatus or may not detect the portion of the user 74 at all (i.e., hands too small, etc.). In another embodiment, the IR sensor 22' with a downward detection field can be placed on a top surface as IR sensor 22''' of apparatus 12 switching the downward detection field 68 into an upward facing detection field 68' detect a hand 76, 76' of a user. However, the present invention is not limited to such an embodiment, and other detection field sizes, and other detection orientations can be used to practice the invention.

In one embodiment, the one or more IR sensors 22" (FIG. 3) include a third detection field 69 of a third size 71 of a third "sideward" facing orientation on the apparatus 12 to detect the hand 76, 76' and/or torso 78 of the user 74 (FIG. 4) desiring to dispense the protective gloves 20. FIG. 3 illustrates only one sideward facing IR sensor 22". However, the present invention is not limited to one sideward facing IR sensor 22" and such IR sensors can be place on both left and right sides of the apparatus 12. In such an embodiment, the second detection field 69 is also of size 71 of about two to four inches (about four to ten centimeters) and includes the third detection field 69 that has been determined experimentally to optimally detect a hand 76, 76' of the user 74 placing it directly next to the one or more IR sensors 22" of the apparatus 12. Detection fields of other sizes (i.e., are too small, etc.) and other orientations may falsely detect another portion of the user 74 walking by the apparatus or may not detect the portion of the user 74 at all (i.e., hands too small, etc.). However, the present invention is not limited to such an embodiment, and other detection field sizes, and other detection orientations can be used to practice the invention.

In one embodiment, the apparatus 12 includes only IR sensor 22, only IR sensor 22' or only IR sensor 22". In another embodiment, the apparatus 12 includes various combinations of two or more of the IR sensors 22, 22', 22". In another embodiment, the apparatus 12 includes all three IR sensors 22, 22', 22". In another embodiment, the apparatus 12 includes various combinations of IR sensors 22, 22', 22" in combination with bar code reader 44 and/or RFID reader 44'. None of the examples illustrated herein limits the claimed invention in any way.

In another embodiment, the one or more IR sensors 22 include an active sensor. However, the present invention is not limited to such an embodiment, and other types of IR sensors and/or other types of sensors can be used to practice the invention Active IR sensors 22 rely on transmissions and feedback to detect changes in the area of coverage. By sending out a constant stream of stimuli, these sensors then measure and compare changes from prior readings. Because of this perpetual back and forth activity, active sensors consume a significantly larger amount of energy compared to passive alternatives. The three most common formats in the active sensor designation include microwave, ultrasonic, and tomographic. However, the present invention is not limited to such embodiments and other types of active IR sensors can be used to practice the invention.

With a "microwave" based active IR sensor, microwave pulses are sent out. From here, reflections that bounce off moving objects are noted and compared to previous entries that the sensor has observed. That works much the same way as a police radar gun and can be effective at tracking and exposing outdoor movement.

"Ultrasonic" active IR sensors focus on sending out high frequency sound waves that are inaudible to the human ear. When the sound waves make contact with people, animals, or other objects that move, a reading is created. Much like a microwave sensor, these return signals are monitored and stored for a later comparison. Outside noise may set off a false alarm if it falls into a frequency or range that is close to the original emission.

"Tomographic" IR sensors monitor radio waves through mesh networks, which gives this option a high accuracy rating. From multiple locations, radio waves are emitted and bounced back to any sensors in range. Considering the ability to confirm the location of a moving object from several points, this option helps eliminate the hassle of false positives and unsubstantiated readings.

In one specific exemplary embodiment, the one or more IR sensors 22 detects an identification card/badge or other card 84, that is white and/or another designated color, and rectangular in shape. However, the present invention is not limited to such an embodiment, and other embodiments can be used to practice the invention.

In such an exemplary embodiment, for example, one or more IR sensor 22 includes, but is not limited to, a specific IR sensor number TCS34725 sold by ADAFRUIT, or other similar IR sensors or companies, which has Red-Green-Blue (RGB) and Clear light sensing elements. This sensor includes an IR blocking filter integrated on-chip localized to the color sensing photodiodes that minimizes the IR spectral component of incoming light and allows different color measurements (e.g., for white, other color id badges/cards or other cards, etc.) to be made accurately. This color based IR sensor 22 described is exemplary only and the present invention is not limited to the IR sensor mentioned and other IR sensors can be used to practice the invention.

In another embodiment, for example, the one or more IR sensor 22 includes, but is not limited to, a specific IR sensor number GP2D15 and/or GP2D120 sold by ACRANAME or other similar IR sensors or companies to detect an identifier badge/card or other card 84 of a specific, size and/or shape (e.g., two inch by four inch rectangle, etc.) These IR sensors use triangulation and a small linear charged couple device (CCD) array to compute a distance and/or presence of objects in a field of view. In order to triangulate, a pulse of IR light is emitted by an emitter. The light travels out into the field of view and either hits an object or just keeps on going. In the case of no object, the light is never reflected, and the reading shows no object. If the light reflects off an object, it returns to the detector and creates a triangle between the point of reflection, the emitter and the detector. The incident angle of the reflected light varies based on the distance to the object. The receiver portion of the IR rangers is a precision lens that transmits reflected light onto various portions of the enclosed linear CCD array based on the incident angle of the reflected light. The CCD array can then determine the incident angle, and thus calculate the distance to the object. This method of ranging is very immune to interference from ambient light and offers indifference to the color of the object being detected. This IR sensor 22 described is exemplary only and the present invention is not limited to the IR sensor mentioned and other IR sensors can be used to practice the invention.

In one embodiment, the one or more light emitting diodes (LED) 24 are also used to indicate the apparatus 12 is in an operational state ready to dispense pairs of protective gloves 20, 20'.

In one embodiment, the one or more light emitting diodes (LED) 24 are connected to the one or more IR sensors 22 to provide a visual indicator that the one or more IR sensors 22 have detected the dispensing event desiring to dispense the pair of protective gloves 20, 20'.

A light-emitting diode (LED) 24 is a two-lead semiconductor light source. It resembles a basic pn-junction diode, which emits light when activated. LEDs are used as indicator lamps for electronic devices, replacing small incandescent bulbs. LEDs have many advantages over incandescent light sources including lower energy consumption, longer lifetime, improved physical robustness, smaller size, and faster switching. The one or more LEDs 24 includes various colors including, but not limited to red, green, blue, yellow, etc.

However, the present invention is not limited to LEDs 24 and other types of bulbs and/or visual and/or sound indicators can be used to practice the invention.

In another embodiment, the LEDs 24 are replaced with and/or used in association with a Liquid Crystal Display (LCD) screen 24' and/or other type of display screens. In such an embodiment, the LCD display screen 24' instructs the user 74 through the dispensing process and provides dispensing instruction and/or other dispensing information. The LCD screen 24' is also used to display status and error messages such as "out-of-order," "please refill," etc. However, the present invention is not limited to such an embodiment and the present invention can be practiced with or without and LCD display screen 24'.

In one embodiment, the one or more LEDs 24 include a dual color LED and/or includes plural LEDs with different colors, that displays a first color, (e.g., red, etc.), when the apparatus 12 is not activated for dispensing but in an operation state, a second color (e.g., green, blue, etc.) when the apparatus 12 has been activated by the one or more IR sensors 22, a third color (e.g., yellow, orange, etc.) when an amount of protective gloves is low, etc. However, the present invention is not limited to such an embodiment and more, fewer and/or other types of LEDs 24 can be used to practice the invention.

In one embodiment, the one or more LEDs 24 are replaced and/or the apparatus 12 further includes a speaker 42 connected to the electrical circuit 18. The speaker 42 is used as an audio indicator such as a pre-determined tone (e.g., two beeps, etc.) or a pre-recorded audio message (e.g., dispensing size large gloves, etc.) that the one or more IR sensors 22 have detected the user 74 desiring to dispense the pair of protective gloves 20, 20'. Such an embodiment can also be used to allow the apparatus 12 to be used by visually impaired people.

In an exemplary embodiment, the protective gloves 20 include medical gloves, food service gloves and/or other types of protective gloves. The protective gloves described are used in many different industries for many different applications. For example, medical gloves may be used by dentists, veterinarians, etc. The food services gloves may be used by mechanics to avoid contact with grease, oil, etc., by painters to avoid contact with paint, paint removers, etc., by craft enthusiasts, by janitorial workers, and for others for tasks at home and in the work place. The protective gloves described herein are not limited to any specific purpose or to any particular industry or environment.

Protective Gloves

"Medical gloves" are disposable gloves used during medical examinations and procedures that help prevent contamination between caregivers and patients. Medical gloves are made of different polymers including latex, nitrile rubber, vinyl, neoprene and/or other materials. Medical gloves are typically 5-10 mils in thickness. A mil is a unit of length equal to one thousandth ($10^{-1}$) of an inch (0.0254 millimeters), used, for example, to specify the thickness of materials.

Medical gloves come unpowdered, or powdered with cornstarch or other powders to lubricate the gloves, making them easier to put on the hands. Unpowdered gloves are being used more often during surgery and other sensitive procedures. Special manufacturing processes are used to compensate for the lack of powder.

There are two main types of gloves: "exam" and "surgical." Surgical gloves have more precise sizing with a better precision and sensitivity and are made to a higher standard. Exam gloves are available as either sterile or non-sterile, while surgical gloves are generally sterile. Sterile gloves are free from bacteria or other living microorganisms.

Food service protective gloves and/or other types of protective gloves provide a cost-effective solution in general food service applications to ensure food safety protection.

"Latex" is a stable dispersion emulsion of polymer microparticles in an aqueous medium. Latex itself is natural, but synthetic latexes have been made. Synthetic latexes can be made by polymerizing a monomer such as styrene that has been emulsified with surfactants. Many people are allergic to latex and latex gloves cannot be used in such circumstances.

"Nitrile rubber," also known as Buna-N. Perbunan, acrylonitrile butadiene rubber, and NBR, is a synthetic rubber copolymer of acrylonitrile (ACN) and butadiene. Trade names include Nipol, Krynac and Europrene. Nitrile butadiene rubber (NBR) is a family of unsaturated copolymers of 2-propenenitrile and various butadiene monomers (1,2-butadiene and 1,3-butadiene). Although its physical and chemical properties vary depending on the polymer's composition of nitrile, this form of synthetic rubber is unusual in being generally resistant to oil, fuel, and other chemicals (the more nitrile within the polymer, the higher the resistance to oils but the lower the flexibility of the material).

"Neoprene" or polychloroprene is a family of synthetic rubbers that are produced by polymerization of chloroprene. Neoprene exhibits good chemical stability and maintains flexibility over a wide temperature range. Neoprene is sold either as solid rubber or in latex form.

"Vinyl" or ethenyl is the ethylene molecule minus one hydrogen atom. When used as medical gloves, due to vinyl gloves having less flexibility and elasticity, several guidelines recommend either latex or nitrile gloves for clinical care and procedures that require manual dexterity and/or that involve patient contact for more than a brief period.

"Polyethylene" (abbreviated PE) or polyethene is a common plastic. Food handler gloves made typically from PE are non-sterile and about one to five mils thickness.

However, the present invention is not limited to the specific types of protective gloves 20, 20' described and more, fewer and other types of protective gloves made from other types of materials can be used to practice the invention.

Figure 7:
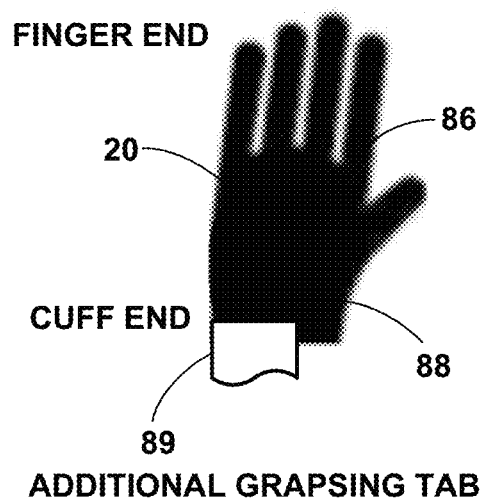
FIG. 7 is a block diagram illustrating an exemplary protective glove.

FIG. 7 is a block diagram 84 illustrating an exemplary protective glove. The protective glove 20 includes a finger end 86 and a cuff end 88.

Figure 8:
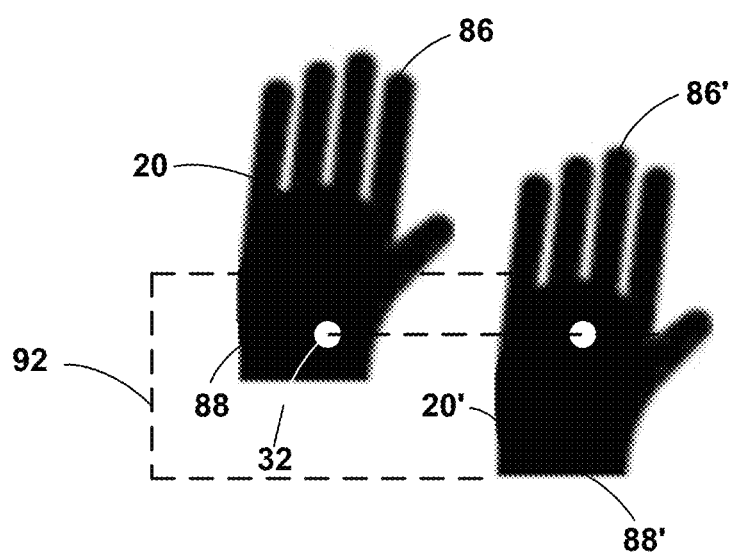
FIG. 8 is a block diagram illustrating an exploded view of an exemplary dispensing overlap for a pair of protective gloves.

FIG. 8 is a block diagram 90 illustrating an exploded view of an exemplary pre-determined dispensing overlap distance 92 for a pair of protective gloves 20, 20' that are stored on the one or more rolls of gloves 30.

The pre-determined over dispensing overlap 92 includes overlapping a finger end 86' of a second glove 20' a pre-determined distance over a palm, finger 86 and cuff end 88 of a first glove 20 in each pair of protective gloves 20, 20'. It has been determined experimentally that the optimal pre-determined overlap distance is about four inches (about ten centimeters).

In one embodiment of the invention, each protective glove 20 further includes an additional grasping tab 89 (FIG. 7) on the cuff end 88, 88' of each pair protective gloves 20, 20'. Only one grasping tab 89 is illustrated on one protective glove 20 for simplicity. In one embodiment, the grasping tab 89 is added to a protective glove 20, 20' during a manufacturing process and is an integral part of the gloves 20, 20'. In such an embodiment, the grasping tabs 89 are used to grasp the pair of protective gloves 20, 20' so not even the cuff ends 88, 88' of the protective gloves 20, 20' are touched by the user 74 when the gloves are dispensed from the apparatus 12.

In another embodiment, the grasping tab 89 is an additional type of mechanical connector 32 that is added after the gloves 20, 20' are manufactured. In another embodiment, the grasping tab 89 includes an antimicrobial compound. However, the present invention is not limited to these embodiments and the invention can be practiced without using the additional grasping tab 89 on the protective gloves 20, 20'.

Figure 9A:
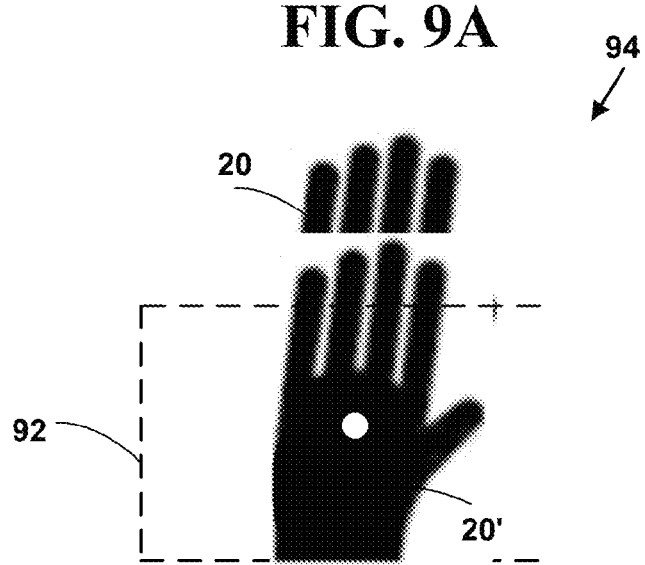
FIG. 9A is a block diagram illustrating an exemplary dispensing overlap for a pair of protective gloves.
Figure 9B:
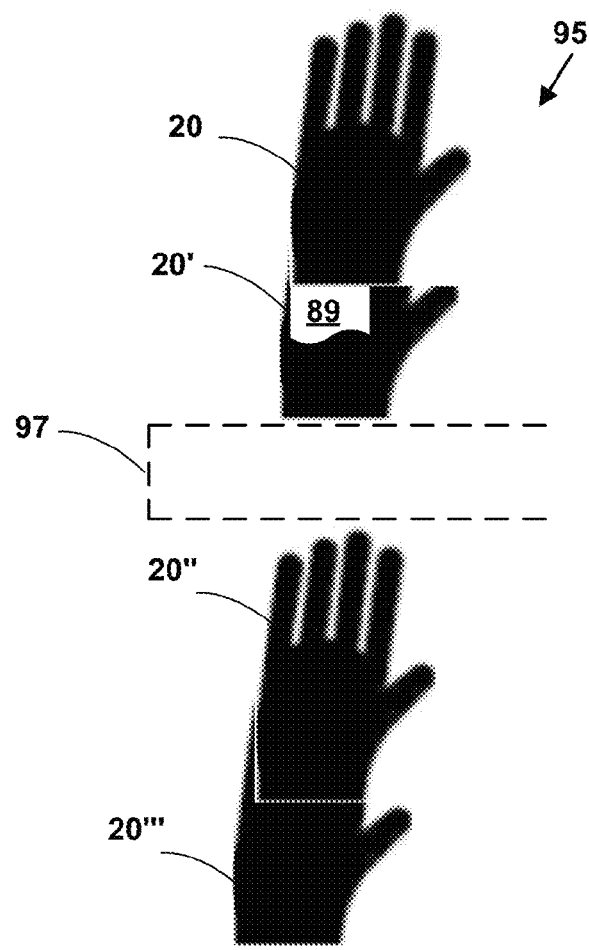
FIG. 9B is a block diagram illustrating an exemplary dispensing space between two pairs of protective gloves.

FIG. 9B is a block diagram 95 illustrating an exemplary dispensing space, a pre-determined space 97 between two pairs of protective gloves 20, 20'. The first pair of protective gloves 20, 20' is illustrated as being connected with additional grasping tab 89 and the second pair of protective gloves 20", 20'" is illustrated in the overlapped configuration 92 without any connector 32 or tab 89. Various combinations of pairs of protective gloves 20, 20' can be used to practice the invention and pairs of gloves 20, 20' with and/or without connector 32 and/or with and without additional grasping tab 89 can be mixed on a single roll 30 of protective gloves.

In one embodiment, the two protective gloves 20, 20' are connected with the pre-determined connector 32 as is illustrated on both gloves 20, 20'. The pairs of protective gloves 20, 20' are stored on the one or more rolls of gloves 30 in this manner so they are physically connected and always dispensed cuff end 88, 88' first for both gloves 20, 20'. A pair of connected protective gloves 20, 20' with connector 32 is rolled on a roll of gloves 30 in the overlapped configuration 94 with a pre-determined space 97 (FIG. 9B) on the roll 30 between each pair of protective gloves 20, 20'.

In this embodiment, the pair of protective gloves 20, 20' connected with the connector 32 are properly dispensed by the cuff ends 88, 88' by advancing individual gloves in the pair of protective gloves 20, 20'. The advancement motion by the electric motor 29 is enough of a mechanical force to break the connection 32 between the two protective gloves 20, 20'. The rack circuit 28 and electric motor 29 move the one or more rolls of protective gloves 30 past the pre-determined space 97 after a pair of protected gloves 20, 20' is dispensed, the apparatus 12 dispenses the next pair of protective gloves 20, 20' on the roll 30 when the one or more IR sensors 22 receive the next glove dispensing event.

In another embodiment, connector 32 is not used. Instead the additional grasping tab 89 (FIG. 7) on the cuff end 88, 88' of each pair of protective gloves 20, 20' is used to connect a pair of protective gloves 20, 20'. The additional grasping tab 89 may also include a chemical (e.g., PSA, etc.) or mechanical bond to keep a pair of protect gloves 20, 20' protected.

In another embodiment, the pre-determined connector 32 is not used to physically connect the pair of protective gloves 20, 20'. In such an embodiment, plural pairs of protective gloves 20, 20' are rolled in the overlapped configuration 94 with a pre-determined space 97 (FIG. 9B) between each pair of protective gloves 20, 20 on a roll of protective gloves 30. Friction between the overlapped surfaces of the protective gloves 20, 20' and the roll 30 keeps the pair of protected gloves 20, 20' on the roll of protective gloves 30' easily connected in pairs without using any connectors 32.

A friction force is a force exerted by a surface when an object moves across it (e.g., kinetic friction) or makes an effort to move across it (e.g., static friction). A "coefficient of friction" is a ratio between a force necessary to move one surface horizontally over another and the pressure between the two surfaces.

Protective gloves made of the various materials described herein have a coefficient of friction large enough to prevent a pair of protection gloves 20, 20' from becoming separated when rolled on the one or more rolls of protective gloves 30. The static coefficient of friction for surfaces of latex gloves known in the art range from about 0.38 for the donning surface (e.g., cuff end 88, 88') to about 1.17 for the gripping surfaces (i.e., fingers 86, 86', palm, etc.). In comparison, the coefficient of static friction for sandpaper on cardboard is about 0.81.

In this embodiment without connector 32, the pair of protective gloves 20, 20' are properly dispensed by the cuff ends 88, 88' by advancing via the rack circuit 28 and electric motor 29 the one or more rolls of protective gloves 30 past the pre-determined space 97 after a pair of protected gloves 20, 20' is dispensed and in response to a next protective glove dispensing event received at the one or more IR sensors 22.

Pairs of protective gloves 20, 20' with or without the connector 32 and the pre-determined overlap 92 are rolled onto the one or more rolls of protective gloves 30. Each pair of protective gloves 20, 20' is dispensed cuff end 88 first to help ensure the finger ends 86 of each pair of gloves are not contaminated by the user 74 who is putting on the protective gloves 20, 20'. The user 74 also has no access to the other pairs of protective gloves 20, 20' on the glove rolls 30, so none of those gloves can be contaminated by the user 74 or by the surrounding environment.

In one embodiment, the one or more rolls of protective gloves 30 include plural pairs of protective gloves 20, 20' (e.g., 100 pairs, etc.) that are rolled directly onto a paper and/or cardboard and/or plastic and/or other material tube which is discarded when all pairs of protective gloves 20, 20' are dispensed.

In another embodiment, the one or more rolls of protective gloves 30 are attached to a paper and/or plastic and/or other material before they are rolled onto tubes. However, this embodiment is less preferred because the paper, etc. material generates significant amounts of additional waste that must be discarded and also adds additional cost to each roll of protective gloves 30.

The apparatus 12 dispenses protective gloves 20, 20' with a method that is in stark contrast to boxes of protective gloves or other mechanical glove dispensers known in the prior art. Protective gloves in such boxes are stored in clumps of gloves in random orientations in which the protective gloves 20, 20' can be extracted from the glove box by the finger ends 86 instead of the cuff 88 and in which multiple gloves can and are removed from the box, touched and contaminated by one or more users and even put back into the box after being contaminated to further contaminate the remaining gloves in the glove box. In the glove dispensers known in the art, once a first protective glove is dispensed, a portion of other protective gloves in the box is exposed to the environment allowing that protective glove or gloves to be contaminated by the external environment the protective gloves are exposed to.

FIG. 9A is a block diagram 94 illustrating the pre-determined dispensing overlap 92 for a pair of protective gloves 20, 20' in a contracted or non-exploded view illustrating the overlap of the two gloves 20, 20' connected with the pre-determined connector 32.

FIG. 9B is a block diagram 95 illustrating an exemplary dispensing pre-determined space 97 between two pairs 20, 20' and 20", 20''' of protective gloves.

Such pairs of protective gloves 20, 20' are rolled onto the glove rolls 30. The pre-determined connector 32 is used to connect each pair of protective gloves 20, 20' with the pre-determined overlap.

In another embodiment, the one or more rolls of protective gloves 30 are replaced with one or more boxes 109 (FIG. 11) of protective gloves 30' including pairs of protective gloves 20, 20' with the pre-determined overlap 92 and/or with and/or without the pre-determined connector 32. In such an embodiment, the one or more boxes 109 includes pairs of protective gloves 20, 20' in a chain format, stacked format, and/or roll format to dispense connected pairs of protective gloves 20, 20' by the cuff ends 88, 88' In such embodiment, the gloves are dispensed through the dispensing slot 34 with the electric motor 29 and/or rollers and gears 31.

Figure 12:
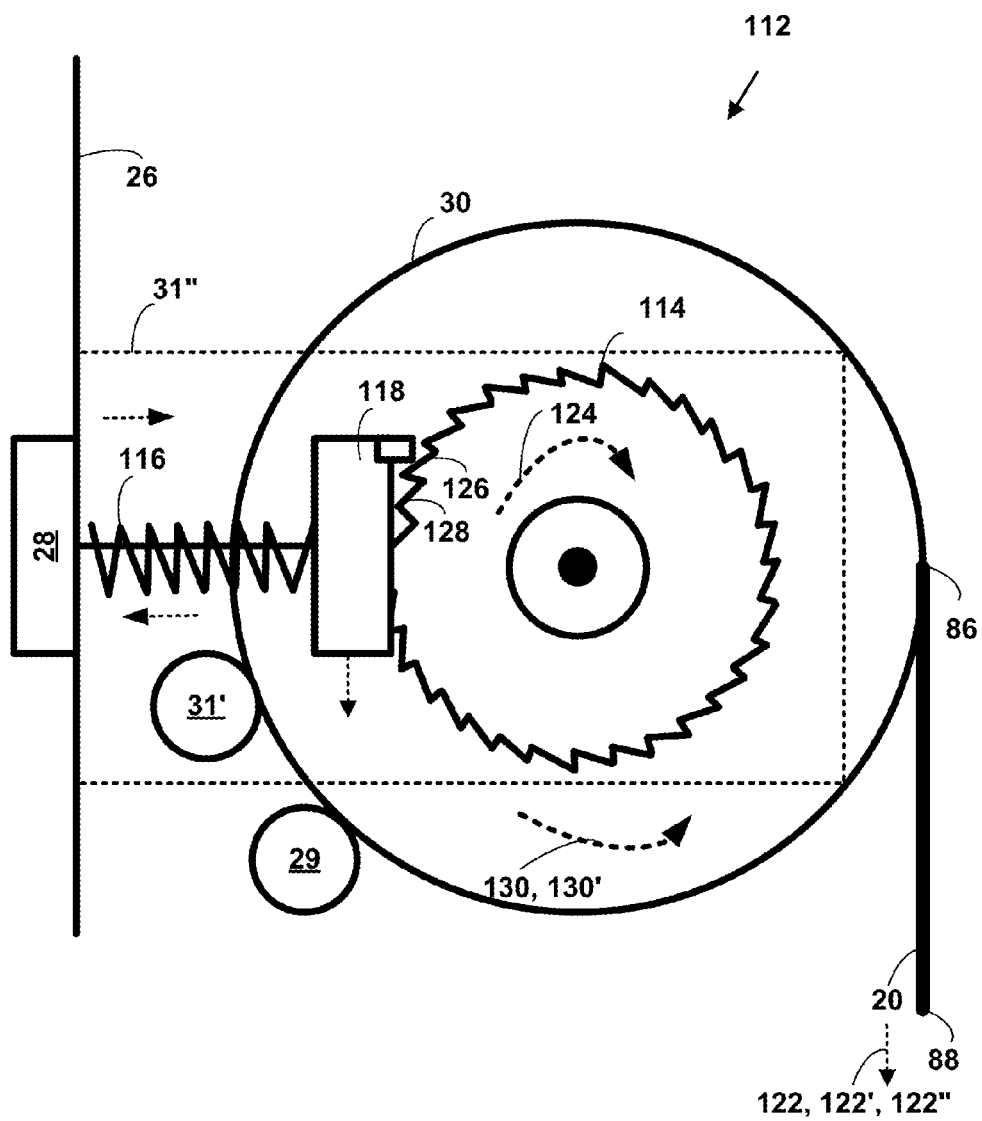
FIG. 12 is a block diagram illustrating additional details of the gears and rollers of the sanitary automatic glove dispensing apparatus of FIG. 1.

FIG. 12 is a block diagram 112 illustrating additional details of the gears and rollers 31 of the sanitary automatic glove dispensing apparatus 12 of FIG. 1. In one embodiment, the additional gears and rollers are connected to the rack circuit 28 and generate one or more electrical signals based on mechanical movements that occur with the one or more rolls of protective gloves 30 and/or the gears and rollers 31.

In one embodiment, the pre-determined connector 32 is used to physically connect the pair of protective gloves 20, 20' for electrical and/or mechanical dispensing. The pair of protective gloves 20, 20' are properly dispensed by the cuff ends 88, 88' in such an embodiment using one or more electrical signals generated by the electronic circuit 18 after detecting a glove detecting event and plural small downward mechanical forces 122, 122' generated by the user 74.

In such an embodiment the apparatus 12 further includes gears and rollers 31, for example, comprising a mechanical ratchet mechanism 31" (FIG. 12). The plural small downward mechanical forces 122, 122', 122" generated by the user 74 are used to both break the pre-determined connector 32 between the pair of protective gloves 20, 20' and to manually dispense both of the protective gloves 20, 20' by the cuff ends 88, 88' (See FIG. 12 and related text). In one embodiment, the ratchet mechanism is locked until a first dispensing event is detected by the one or more IR sensors 22, 22'. In one embodiment, the ratchet mechanism 31" is locked and unlocked by one or more electronic signals sent from the electronic circuit 18 to the rack circuit 28.

In an exemplary embodiment, where the pre-determined connector 32 is used, the pre-determined connector 32 includes a connection created by a mechanical connector, by a chemical bond, a heat bond and/or a mechanical compression bond. However, the present invention is not limited to these connectors 32 and more, fewer or other connectors can also be used to practice the invention.

The mechanical connector 32 includes a small piece of tape or paper, plastic or other material and/or grasping tab 89 with an applied pressure sensitive adhesive (PSA) as described herein. The tape includes medical tape, painters tape, cellophane tape or other type of tape depending on the type of protective gloves being used.

When a pair of protective gloves 20, 20' are dispensed, the tape can be used as a manual method to track how many pairs of gloves are dispensed by users 74. For example, each time a pair of protective gloves 20, 20' are dispensed by user 74, he can place the piece of tape on a wall chart under his name next to a timeline indicating a time when the gloves where changed.

However, the tape connector 32 is not as desirable in a food service environment where care must be taken so the tape connector 32 does not end up in any food being served. It is also not as desirable in some medical environments such as surgical environments where care must be taken so the tape does not end up in any patients being operated on, etc.

The chemical connector 32 includes plural types of adhesives, rubber cement and/or other type of glues and/or adhesives that create a temporary chemical bond but does not accept use of the protective gloves 20, 20' in any environment that the protective gloves 20, 20' are used in. In one embodiment, the chemical connector 32 includes a pressure sensitive adhesive (PSA).

In one exemplary embodiment, the chemical connector 32 includes a "pressure-sensitive adhesive" (also called a self-adhesive, self-stick adhesive). A PSA is an adhesive which forms a bond when pressure is applied to marry an adhesive with an adhered surface. No solvent, water, or heat is needed to activate the adhesive. PSAs are used in pressure-sensitive tapes, labels, note pads, and a wide variety of other products. A common example of a PSA is that used on the sticky-notes such as POST-IT notes.

PSAs are commonly used on medical applications such as contact wound care dressings, EKG electrode pads, medical tapes, analgesic and transdermal drug patches, and other medical applications.

Pressure-sensitive adhesives are designed with a balance between flow and resistance to flow. The bond forms because the adhesive is soft enough to flow, or wet, the "adherend." The bond has strength because the adhesive is hard enough to resist flow when stress is applied to the bond. Once the adhesive and the adherend are in proximity, there are also molecular interactions such as van der Waals forces involved in the bond, which contribute significantly to the ultimate bond strength. PSAs exhibit viscoelastic (viscous and elastic) properties, both of which are used for proper bonding.

Pressure-sensitive adhesives are characterized by their shear and peel resistance as well as their initial tack. These properties are dependent, among other things, on the formulation, coating thickness and temperature.

PSAs are usually based on an elastomer compounded with a suitable tackifier such as a rosin ester. An "elastomer" is a polymer with viscoelasticity (having both viscosity and elasticity) and very weak inter-molecular forces, generally having low Young's modulus and high failure strain compared with other materials. "Esters" are derived from an acid (e.g., Carbolic acid, etc.) and an alcohol. The elastomers include, but are not limited to, Butyl rubber Ethylene-vinyl acetate (EVA), Natural rubber, nitriles, Silicone rubbers, Styrene block copolymers (SBC) and/or Vinyl ethers. However, the present invention is not limited to these elastomers and other compounds for PSAs can be used to practice the invention.

None of the PSA's or other adhesives and/or glues used with the invention are harmful or detrimental to the user 74 of the protective gloves 20, 20' or anything the user 74 is using the gloves 20, 20' on or for (e.g., surgical patient, etc.).

All of the bonds produced by the various types of PSA based bonding for the chemical connectors 32 are easily broken by a small mechanical force 122 applied to the pair of gloves 20, 20', such as downward force 122 by pulling the cuff end 88 of the first protective glove 20 in a downward motion and detaching it from the second protective glove 20' in the pair of bonded protective gloves as well as moving the first protective glove 20 down far enough for dispensing as well.

In one exemplary embodiment, a heat connector 32 includes heat bonding of the pair of protective gloves 20, 20'. The heat bonding includes, but is not limited to such methods as radiant heat bonding, point-bonding, ultrasonic boning, and/or other heat-based bonding techniques.

"Radiant heat bonding" takes place by exposing the protective gloves to a source of radiant energy in the infrared range. The electromagnetic energy radiated from the source is absorbed by the protective gloves 20, 20', increasing their temperature. The application of radiant heat is controlled so that it melts a small portion of the protective gloves 20, 20' material without affecting the rest of the glove surface. Bonding occurs when the glove material re-solidifies upon removal of the source of radiant heat.

"Point-bonding" is a method for thermally bonding in disposables as diaper, sanitary products, and medical products. This method involves the use of a two-roll nip consisting of a heated male patterned metal roll and a smooth or patterned metal roll. This second roll may or may not be heated, depending on the application. In a typical production line, the pair of gloves is fed by an apron leading to a calender nip and the glove material temperature is raised to the point at which tackiness and melting cause glove material segments caught between the tips of engraved points and the smooth roll to adhere together. A "calender" is a series of hard pressure rollers used to form or smooth a sheet of material such as paper or plastic film or protective gloves 20. The heating time is typically of the order of milliseconds. The bond breaking strength is dependent on the process temperature and pressure and other parameters like the contact time, quench rate and calender pattern.

"Ultrasonic bonding" is a process that involves the application of rapidly alternating compressive forces of ultrasonic vibrations to localized areas of the protective glove materials. The stress created by these compressive forces is converted to thermal energy, which softens the protective glove materials as they are pressed against each other. Upon removal from the source of ultrasonic vibration, the softened glove materials cool, solidifying the bond points. This method is frequently used for spot or patterned bonding of mechanically bonded materials. No binder is necessary when synthetic materials are used since these materials are self-bonding.

All of the bonds produced by the various types of heat based bonding are easily broken by a small mechanical force 122 applied to the pair of gloves, such as downward force by pulling the cuff end 88 of the first protective glove 20 in a downward motion and detaching it from the second protective glove 20' in the pair of bonded protective gloves.

In one exemplary embodiment, the mechanical connector 32 includes mechanical compression bonds created by running each pair of protective gloves through a die that presses or rolls a small portion of the pair of protective gloves 20, 20' together under high pressure.

All of the bonds produced by the various types of mechanical based bonding are easily broken by a small mechanical force applied to the pair of gloves, such as downward force by pulling the cuff end 88 of the first protective glove 20 in a downward motion and detaching it from the second protective glove 20' in the pair or bonded protective gloves.

The electro-mechanical glove roll rack 26 that engages and disengages one or more rolls of protective gloves 30 includes the rack circuit 28 and the electronic motor 29 connected to the electronic circuit 18 for moving the roll of protective gloves 30 a first and a second pre-determined distance to dispense the pair of protective gloves 20, 20' by cuff ends 88, 88' in response to one or more electrical signals from the electronic circuit 18.

The electronic motor 29 includes a motor powered by AC and/or DC power supplies 16. The electro-mechanical glove roll rack 26 further includes one or more additional rollers and/or gears 31', 31" (e.g., FIG. 12) connected to the electronic motor 29 to dispense a pair of protective gloves 20, 20' from the one or more rolls of gloves 30.

In one embodiment, the electronic motor 29 is in direct contact with the one or more rolls of protective gloves 30 (FIGS. 1 and 12). In another embodiment, the electronic motor 29 is in contact with the one or more additional rollers or gears 31. However, the present invention is not limited to such embodiments and other embodiments may be used to practice the invention.

In one embodiment, for example, the electronic motor 29 includes a 6-volt DC, low RPM, high-torque, permanent magnet multi-gear motor such as those sold by the KINMORE Motor company (e.g., part no. KM-37B555-50-16150, etc.) and other companies. However, the present invention is not limited to such an exemplary embodiment and other types of electronic motors from other companies can also be used to practice the invention.

In one embodiment, the one or more rolls of protective gloves roll 30 includes a protective cover (e.g., cellophane, vinyl, PVC, etc.) that protects the gloves 20 and is removed before installing into apparatus 12. The glove rolls 30 also include a paper leader and/or plastic leader and/or leader made of another materials that is fed through the dispensing slot 34 for dispensing the pairs of protective gloves 20, 20' by cuff ends 88, 88' on the rolls 30. The paper leader is discarded after it is fed through dispensing slot leaving the pairs of protective gloves 20, 20' connected together on the roll for dispensing from the apparatus 12.

In one embodiment, the dispensing membrane 36 integral to the dispensing slot 34 for protecting the pair of protective gloves 20, 20' during dispensing and for protecting the plural protective gloves 20 on the one or more rolls of protective gloves 30 from contamination includes an antimicrobial surface with an antimicrobial agent that inhibits or reduces the ability of microorganisms to grow on the surface of the dispensing membrane 36. The antimicrobial agents, include, but are not limited to, antibacterial, antifungal, antiviral and/or other antimicrobial agents.

In another embodiment, the dispensing membrane 36 coats each pair of protective gloves 20, 20' as they are dispensed from the apparatus 12 with an antimicrobial agent. In such an embodiment, the dispensing membrane 36 includes an antimicrobial gel and/or other antimicrobial coating that is transferred from the dispensing membrane 36 onto each pair of protective gloves 20, 20' as they are dispensed for additional anti-contamination protection. However, the present invention is not limited to these embodiments and the invention can be practiced with and/or without any antimicrobial surfaces.

In one embodiment, the apparatus 12 further includes a dispensing membrane 36 that is replaceable, selectively removable and attachable and is replaced every time a new roll of gloves 30 is added to apparatus 12 to ensure the protective gloves 20 are not contaminated by an environment and/or user 74 when the apparatus 12 is being operated as the pairs of protective gloves 20, 20' are dispensed.

In one embodiment, the apparatus 12 further includes a dispensing membrane 36 that is replaceable, selectively removable and attachable and is replaced every time a new roll of gloves 30 is added to apparatus 12, that extends below the apparatus 12 to protect a majority of the cuff ends 88, 88' of the pair of protective gloves 20, 20' as they are dispensed.

However, the present invention is not limited to these embodiments and other embodiments can be used to practice the invention.

Dispensing a Pair of Protective Gloves

EXAMPLE-1

To dispense a pair of protective gloves 20, 20', in one exemplary embodiment, the one or more IR sensors 22' are configured with a downward facing detection field 68 (e.g., FIG. 4). The user 74 generates a first dispensing event with a first hand 76. The electronic circuit 18 receives one or more electrical signals from the one or more IR sensors 22' and sends the rack circuit 28 a first electronic signal to advance the roll of protective gloves 30 in the glove roll rack 26 a first pre-determined distance to expose a first cuff end 88 of a first glove 20 in a first pair of protective gloves 20, 20' from the dispensing slot 34 in the apparatus 12. The cuff 88 of the first glove 20 passes through the dispensing membrane 36.

The user 74 desiring the protective gloves 20, 20', grabs the first cuff end 88 of the first glove 20 with the first hand 76 and/or second hand 76' and generates a second dispensing event at the one or more IR sensors 22' with the first hand 76 (or second hand 76'). The electronic circuit 18 sends a second electronic signal to the rack circuit 28 to advance the glove roll 30 a second pre-determined distance to completely dispense the first protective glove 20 from the apparatus 12 and to expose a second cuff end 88' of the second protective glove 20' in the first pair of protective gloves 20, 20'.

The user 74 grabs the first protective glove 20 by the cuff end 88 (or by additional grasping tab 89) without touching or contaminating the finger end 86 with the second hand 76' and places the first hand 76 into the first protective glove 20 via the cuff end 88, thereby having the first hand 76 covered by the first protective glove 20.

The user 74 grabs the cuff end 88' (or by additional grasping tab 89) of the second protective glove 20' with the second gloved hand 76' and generates a third dispensing event at the one or more IR sensors 22' with the first hand 76 and/or the second hand 76'. The electronic circuit 18 sends a third electronic signal to the rack circuit 28 to advance the glove roll 30 a second pre-determined distance to advance the roll of gloves 30 to completely dispense the second protective glove 20'.

After dispensing the second protective glove 20' completely, no additional protective gloves 20, 20' are exposed from the apparatus 12 as there is a pre-determined space 97 (FIG. 9B) between each pair of protective gloves 20, 20' on the roll 30. Not exposing any additional pairs of protective gloves 20, 20' thereby prevents contamination of any additional pairs of protective gloves 20, 20' by a surrounding environment or by another user 74. Another cuff end 88 of a first glove 20 from another pair of protective gloves 20, 20' is not dispensed until another dispensing event is received by the one or more IR sensors 22.

The user 74 grabs the second protective glove 20' with the first gloved hand 76 by the cuff end 88' (or by additional grasping tab 89) and places the second hand 76' into the second protective glove 20' via the cuff end 88', thereby having the second hand 76' covered by the second protective glove 20' and creating a pair of hands 76, 76' covered with protective gloves 20, 20'.

No other portions of any of the protective gloves 20, 20' on the glove roll 30 are exposed to the environment outside of the apparatus 12 after the second protective glove 20' is fully dispensed. This prevents all other pairs of protective gloves 20, 20' on the roll of gloves 30 from being contaminated by an environment and other user 74' before their use is required by a user 74.

In this example, the user 74 generates four dispensing events that are captured by the one or more IR sensors 22.

FIG. 10 is a block diagram 96 illustrating the sanitary automatic glove dispensing apparatus of FIG. 1 with an LCD display screen 24' and audio speaker 42.

EXAMPLE-2

In such an embodiment wherein the pairs of protective gloves 20, 20' are automatically dispensed based on one or more pre-determined timings, the user 74 may be provided with electronic instructions 98 via the LCD display 44' and/or with audio instructions 100 via the speaker 42. For example, the apparatus 12 may display stored electronic messages on the LCD display 44' and/or pre-recorded audio instructions vis the speaker 42 such as: "(1) ready to dispense a pair of gloves; (2) first glove dispensed, grab the cuff end and wait; (3) dispensing all of first glove; (4); dispensing second glove; (5) grab the cuff end of the second glove and wait; (6) dispensing all of second glove, etc." However, the invention is not limited to such exemplary electronic text and/or audio messages and other messages can be used to practice the invention.

In this embodiment, the user 74 generates one dispensing event that is picked up by the one or more IR sensors 22 and the apparatus 12 automatically dispenses a pair of protective gloves 20, 20' thereafter without further input from the user.

In another embodiment, the first IR sensor 22' with the downward facing detection field 68 is replaced with an IR sensor 22 with a forward facing detection field 64 in the apparatus 12 (e.g., FIGS. 5 and 6). The user 74 waves the first and/or second hand 76, 76' and/or places torso 78 in front of the IR sensor 22, one or more times as was described above to dispense a pair of protective gloves, 20, 20'.

In another embodiment, the electronic circuit 18 is configured for using pre-determined timings after a first dispensing event is received. For example, upon the one or more IR sensors 22, 22' (FIG. 4, FIG. 5) and/or bar code reader 44 and/or RFID reader 44' detecting a first dispensing event the electronic circuit 18 will cause the cuff end 88 of the first protective glove 20 to be automatically dispensed. In this embodiment, the user 74 does not have to generate any additional dispensing event with a hand 76, 76' and/or torso 78 and/or bar code 46 and/or RFID tag 48.

Instead, the remaining dispensing events are generated automatically by the electronic circuit 18 based on one or more pre-determined timings. For example, the whole first protective glove 20 is dispensed five to ten seconds after the first detected dispensing event that exposes the cuff end 88. The user 74 is able to grab the cuff end 88 of the first protective glove 20 and wait for the whole glove 20 to be automatically dispensed. Then, after another pre-determined amount of time, (e.g., another five to ten seconds, etc.) the whole first protective glove 20 is automatically dispensed. The user 74 is given enough time (e.g., another five to ten seconds, etc.) to grab by the cuff end 88 and apply the first glove 20 to the first hand 76 thereby creating a first gloved hand 76.

Then, after another pre-determined time period, another five to ten seconds, the cuff 88' of the second protective glove 20' is automatically dispensed. The user 74 is able to grab the cuff end 88' of the second protective glove 20' with the gloved hand 76 and wait for the whole second glove 20' to automatically be dispensed after another five to ten seconds. The user 74 grabs the second protective 20' by the cuff end 88' and applies it to the second hand 76'. At this point both hands 76, 76' have a pair of protective gloves 20, 20' applied to the hands 76, 76' over the user.

In such an embodiment, the pre-determined timing can be adjusted through the interface port 38. In such an embodiment, if the user 74 does not grasp the cuff 88 of the first glove 20 when instructed to do so, the first glove 20 will still be automatically dispensed from the apparatus 12 and may fall out of the apparatus 12 to a floor, counter or other unsanitary surface.

EXAMPLE-3

In another embodiment, the first IR sensor 22' with the downward facing detection field 68 used with pre-determined timing is replaced with an IR sensor 22 with a forward facing detection field 64 in the apparatus 12 (e.g., FIGS. 5 and 6) that is used with the pre-determined timing.

The user 74 waves the first and second hands 76, 76' and/or places a torso 78 in front of the IR sensor 22, one time as was described above to automatically dispense a pair of protective gloves, 20, 20' based on the pre-determined timings.

To prevent pairs of protective gloves 20, 20' from being accidentally dispensed after a first dispensing event is detected by the one or more IR sensors 22, the apparatus 12 can be configured with a first IR sensor 22 with a forward facing detection field 64 and with a second IR sensor 22' with a downward facing detection field 68. After the first dispensing event is detected by the second IR sensor 22', the user 74 must stand in front of the apparatus 12 and the first IR sensor 22 must detect the user's torso 78 and/or hands 76, 76' and send one or more signals to the electronic circuit 18 before the pair of protective gloves 20, 20' are automatically dispensed from the apparatus 12.

EXAMPLE-4

In another embodiment, to prevent pairs of protective gloves 20, 20' from being accidentally dispensed after a first dispensing event is detected by the one or more IR sensors 22, the apparatus 12 can be configured with an IR sensor 22' with a downward facing detection field 68 and/or a bar code reader 44 and/or RFID reader 44' (FIG. 6). After the first dispensing event is detected by the first IR sensor 22', the user 74 must stand in front of the apparatus 12 with their identification badge/card 84 visible on the user torso 78 and send a signal to a bar code reader 44 and/or RFID reader 44' and the electronic circuit 18 before the pair of protective gloves 20, 20' are automatically dispensed from the apparatus 12.

Figure 11:
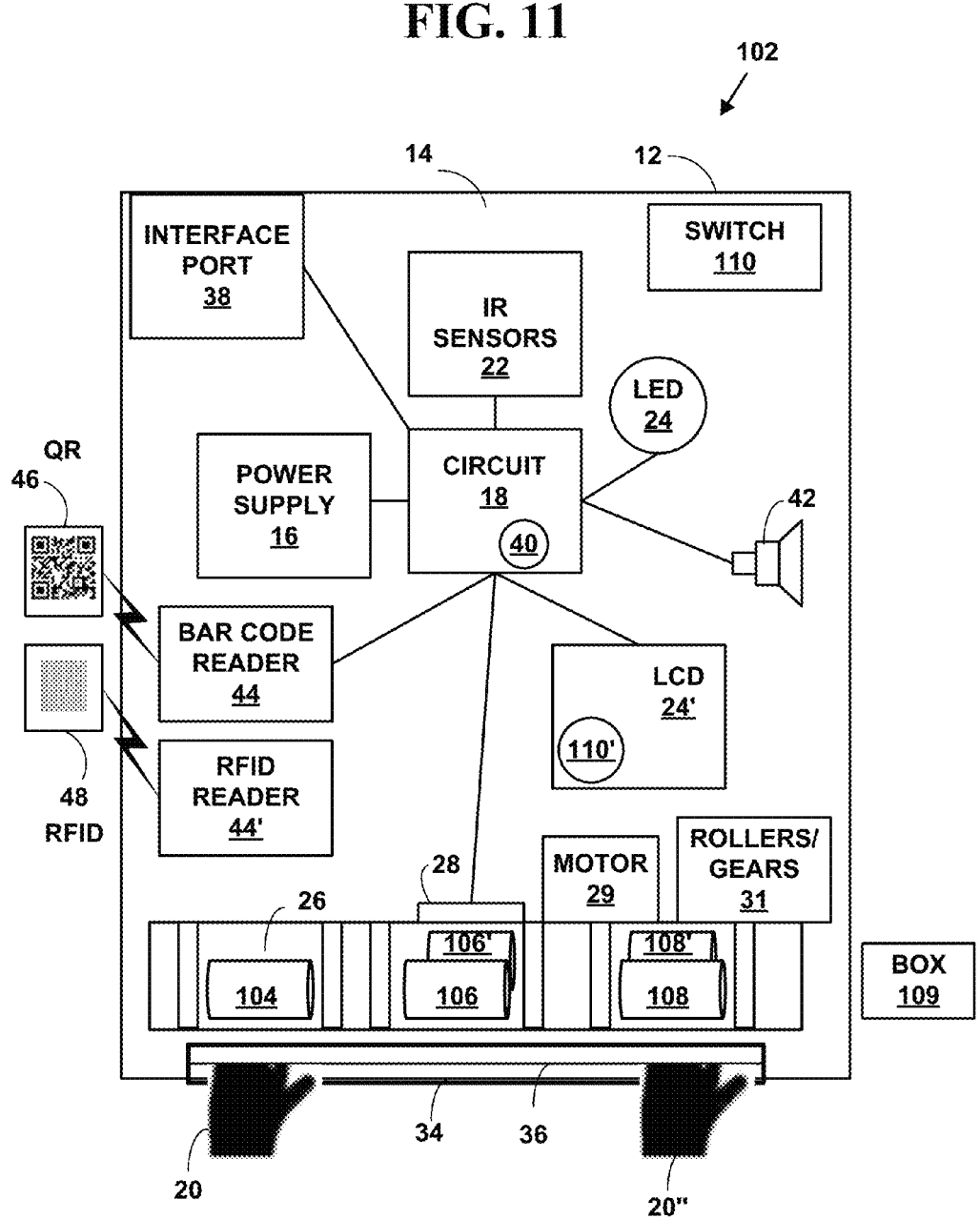
FIG. 11 is a block diagram illustrating another sanitary automatic glove dispensing apparatus with three rolls of protective gloves.

FIG. 11 is a block diagram 102 illustrating another sanitary automatic glove dispensing apparatus 12 with three rolls of protective gloves 104, 106, 108 in a side-by-side configuration.

In such an embodiment, the apparatus 12 includes a manual 110 or graphical 110' selection switch (FIGS. 10, 11) that allows the user 74 to select one of three glove sizes, medium 104, large 106 or extra-large 108. These three sizes, medium, large and extra-large are the most popular sizes of gloves used by users 74. The graphical selection switch 110 is displayed on the LCD 24' screen and/or other display screen on a front surface of the protective case 14. However, the present invention is not limited to this embodiment and other combinations of sizes can also be used. In addition, all the rolls of gloves 104, 106, 108 can include a same size of pairs of protective gloves 20, 20'.

In one embodiment, the selection switches 110, 110' are automatically selectable and/or changeable by a bar code 46 or RFID tag 48 without touching by the user 74. However, the present invention is not limited to this embodiment and other embodiments can be used to practice the invention.

EXAMPLE-5

In another embodiment, if the user 74 is using a bar code 46 or RFID tag 48 on an identification badge/card 84 to dispense the pair of protective gloves 20, 20', the card code reader 44 and/or RFID reader 44' sends the electronic circuit 18 an appropriate signal to cause the rack circuit 28 to automatically select and dispense a pair of correct size protective gloves 20, 20'. For example, the QR bar code 46 and/or RFID tag 48 may include the information "Ilya Ray, nurse practitioner, size medium, employee number 12-3456-78" so the apparatus 12 will automatically activate the glove roll 104 with size medium gloves and dispense a pair 20, 20' of size medium protective gloves.

FIG. 11 is illustrated with three rolls of protective gloves 104, 106, 108. However, the present invention is not limited to this embodiment and more (e.g., four to six rolls, with small, medium, large and extra-large gloves, etc.) or fewer (e.g., large and extra large, etc.) rolls of protective gloves can be used to practice the invention.

In addition, FIG. 11 illustrates three rolls of protective gloves that are inserted into the glove roll rack 26 in a side-by-side configuration. However, the present invention is not limited to this embodiment. For examples, in another embodiment, the three or more rolls of protective gloves are placed behind (e.g., FIG. 11, 106', 108' etc.) each other starting with a first roll of protective gloves nearest a front surface (e.g., 106, 108, etc.) of the protective case 14 of the apparatus 12. In such an embodiment, the protective case 14 may include three or more dispensing slots 34 and/or include additional gears/rollers 31 that move a desired roll of protective gloves 30 to a desired position over the dispensing slot 34 to dispense a pair of protective gloves 20, 20' by the cuff ends 88, 88'. The present invention is not limited to the embodiments described and various other placements and configurations of the rolls of the protective gloves can be used to practice the invention.

The apparatus 12 may also include plural rolls of pairs of protective gloves 20, 20' of different materials and different thicknesses instead of different sizes. For example, a user 74 may be allergic to latex gloves and select a roll of nitrile gloves instead. Or a food service worker may use a one mil pair of gloves for preparing vegetables and then select a three mil pair of gloves for preparing chicken, etc. In another embodiment, the apparatus 12 also allows selection of sterile and non-sterile protective gloves and/or selection of medical and/or exam protective gloves. The different types of rolls of gloves can be selected with mechanical switch 110, graphical switch 110', and/or with an additional bar code 46 and/or RFID tag 48.

However, the present invention is not limited to the embodiments described and other embodiments with plural rolls of protective gloves can also be used to practice the invention.

In an embodiment illustrated in FIG. 11, the one or more rolls of protective gloves 104, 106, 108 include pairs of protective gloves that are folded one or more times over and around a vertical axis. After the fold, the pair of protective gloves are smaller in size when compared with a full size of an unfolded protective glove. The folding allows the pairs of protective gloves 20, 20' to be stored on rolls that are shorter in length and allows multiple rolls 104, 106, 108 of gloves 30 to be stored in and dispensed from apparatus 12. The folded pairs of protective gloves 20, 20' on such rolls 104, 106, 108 are still dispensed by the cuff ends 88, 88' and still easily grabbed, unfolded and applied to a user's 74 hands 76, 76'. In another embodiment, the glove roll rack 26 includes additional rollers/gears 31 to automatically unfold the pairs of protective gloves 20, 20' as they are being dispensed by the cuff ends 88, 88'.

In another embodiment, only thumb portions of the pair of protective gloves 20, 20' are folded inward around a vertical axis onto the finger portions 86, 86' of the pair of protective gloves. This also allows a roll of protective gloves 30 to be shorter in length. The folded thumbs have minimal effects on the dispensing and donning of the pairs of protective gloves 20, 20' as they are dispensed by the cuff ends from the apparatus 12.

However, the present invention is not limited to the folding described and more, fewer or other types of folds can be used to practice the invention.

EXAMPLE-6

In another embodiment, with the one or more IR sensors 22, 22' configured with forward facing 64 and downward facing 68 detection fields, the user 74 generates a first dispensing event with a torso 78 and/or bar code 46 or RFID signal 48 from an identification badge/card (FIGS. 5, 6). In such an embodiment, the electronic circuit 18 receives one or more electrical signals from the one or more IR sensors 22 (e.g., forward facing detection fields 64, etc.) and sends the rack circuit 28 a first electronic signal to advance the roll of protective gloves 30 in the glove roll rack 26 a first pre-determined distance to expose a first cuff end 88 of a first glove 20 in a pair of protective gloves 20, 20' from the dispensing slot 34 in the apparatus 12.

The user 74 desiring the protective gloves 20, 20', grabs the first cuff end 88 of the first glove 20 with a second hand 76' and generates a second dispensing event at the one or more IR sensors 22' (e.g., downward facing detection fields 68, etc.) with the first hand 76. The electronic circuit 18 sends a second electronic signal to the rack circuit 28 to advance the glove roll 30 a third pre-determined distance to advance the roll of gloves 30 to fully dispense the first glove 20 from the apparatus 12 which is being held by the user 74 with the second hand 76'.

The user 74 inserts the first hand 76 into the first cuff end 88 of the first glove 20 creating a first gloved hand 76. The user 74 generates a third dispensing event at the one or more IR sensors 22' with either the first hand 76 or second hand 76'. The electronic circuits 18 receives one or more electrical signals from the one or more IR sensors 22' and sends the rack circuit 28 a third electronic signal to advance the roll of protective gloves 30 in the glove roll rack 26 a fourth pre-determined distance to expose a second cuff end 88' of a second glove 20' from the dispensing slot 34 in the apparatus 12.

The user 74 desiring the protective gloves 20, 20', grabs the second cuff end 88' of the second glove 20 with the second ungloved hand 76' and generates a fourth dispensing event at the one or more IR sensors 22' with the first gloved hand 76. The electronic circuit 18 sends a fourth electronic signal to the rack circuit 28 to advance the glove roll 30 a fourth pre-determined distance to advance the roll of gloves 30 to fully dispense the second glove 20' from the apparatus 12 which is being held by the user 74 with the second ungloved hand 76'.

The user 74 grabs the cuff end 88' of the second glove 20' with the first gloved hand 76. The user 74 inserts the second hand 76' into the cuff end of the second glove 20' creating a second gloved hand 76'.

The second glove 20' is dispensed from the apparatus 12 leaving no portions of any additional pairs of protective gloves 20 exposed from the dispensing slot 34 of the apparatus 12. Another dispensing event must be received on the one or more IR sensors 22 before another pair of protective gloves 20, 20' are dispensed by cuff ends 88. This ensures that none of the remaining protective gloves 20 on the roll of gloves 30 are exposed to the environment and subject to contamination.

In alternative embodiments, the one or more rolls of protective gloves 30 including plural pairs of protective gloves 20, 20' do not include connector 32. In such embodiments, the pair of protective gloves 20, 20' are not physically connected with connector 32. Instead the electronic circuit 18 is able to successfully dispense pairs of protective gloves 20, 20' one at a time, using data about the physical size, shape, length, etc. of a single protective glove 20.

EXAMPLE-7

In another embodiment, the apparatus 12 includes an electro-mechanical glove dispenser that requires the user 74 execute one or more additional manual actions to dispense a pair of protective gloves 20, 20'. To dispense a pair of protective gloves 20, 20', for example, in one exemplary embodiment, the one or more IR sensors 22' are configured with a downward facing detection field 68 (and/or IR sensor 22 with a forward facing detection field 64, and/or via bar code reader 44 and/or RFID reader 44', etc.). The user 74 generates a first dispensing event with a first hand 76, and/or torso 78 and/or bar code 46 and/or RFID tag 48. The electronic circuit 18 receives one or more electrical signals from the one or more IR sensors 22' and sends the rack circuit 28 a first electronic signal to advance the roll of protective gloves 30 in the glove roll rack 26 a first pre-determined distance to expose a first cuff end 88 of a first glove 20 in a pair of protective gloves 20, 20' from the dispensing slot 34 in the apparatus 12. The cuff end 88 of the first glove 20 passes through the dispensing membrane 36.

The user 74 tugs with the first hand 76 (or both hands 76, 76', etc.) on the exposed first cuff end 88 of the first glove 20 with a small downward mechanical 122 force about five pounds of force or about 22.2 Newtons (N), etc. However, the present invention is not limited to such forces and other mechanical downward forces can be used to practice the invention.

In the United States, the small mechanical force 122 includes about five pounds or 22.2N force that is a maximum downward force an apparatus 12 can require for user actions and still be compliant for use under the Americans with Disabilities Act (ADA) (e.g., 42 U.S.C. ch. 126, § 12101 et seq.). However, the present invention is not limited to ADA compliant apparatus and other apparatus can be used to practice the invention.

When the user 74 tugs down on the cuff end 88 of the first protective glove 20 with the appropriate mechanical force 122, the roll of protective gloves 30 rotates a pre-determined distance 124 causing the notch arm 118 (FIG. 12) to slip off a current notch 126 on the notched gear 114, depress the spring 116 and move the notch arm 118 from the current notch 128 on the notched gear 114 to a next notch 128 on the notched gear 114 and be stopped on the next notch 128 due to the angle of the notch on the notched gear 114.

The small downward force 122 along with an opposing stopping force 130 generated by the notch arm 118 hitting a surface of the next notch 128 is enough to easily break the connector 32 between the pair of gloves 20, 20' and also expose the cuff end 88' of the second protective glove 20', but not enough to completely dislodge the second protective glove 20' from the apparatus 12.

The user 74 inserts the first hand 76 into the first cuff end 88 of the first protective glove 20 thereby creating a first gloved hand 76. The user 74 grabs the second cuff end 88' of the second glove 20' which is partially exposed from the dispensing slot 34 of the apparatus 12 with the second hand 76' (or both hands 76, 76') and pulls down with a second small mechanical force 122' (e.g., about five pounds, about 22.2N, etc.) completely dislodging the second glove 20' from the apparatus 12.

The user 74 inserts the second hand 76' into the second glove 20' via the second cuffed end 88' creating a second gloved hand 76', thereby creating a pair of gloved hands 76, 76' in dispensed protective gloves 20, 20'.

The second small downward force 122' along with an opposing stopping force 130' generated by the notch arm 118 hitting a surface of yet another next notch on the notched gear 114 is enough to completely dislodge the second protective glove 20' from the apparatus 12.

Since the protective gloves 20, 20' are connected with connector 32 dispensed in pairs, no additional pairs of protective gloves 20, 20' are exposed from the apparatus 12, thereby preventing contamination of the remaining pairs of protective gloves 20, 20' on the roll of gloves 30.

In embodiments where small mechanical forces 122 are required by the user 74, the small mechanical forces 122 generate one or more feedback electrical signals when the one or more rolls of protective gloves 30 are rotated that are captured by the rack circuit 28. The one or more feedback electrical signals are used by the rack circuit 28 and/or are sent to the electronic circuit 18 to properly adjust movements of the one or more rolls of protective gloves 30 electrically and position them to properly dispense one pair of protective gloves 20, 20'.

Another cuff end 88 of another pair of protective gloves 20, 20' is not exposed until a new dispensing event is detected by the one or more IR sensors 22, 22' and/or bar code reader 44 and/or RFID reader 44'.

The second glove 20' is dispensed from the apparatus 12 leaving no portions of any additional pairs of protective gloves 20 exposed to the environment from the dispensing slot 34 of the apparatus 12. Another dispensing event must be received on the one or more IR sensors 22 before another pair of protective gloves 20, 20' are dispensed by cuff ends 88. This ensures that none of the remaining protective gloves 20 on the roll of gloves 30 are exposed to the environment and subject to contamination.

There are other combinations of IR sensors 22, 22' and/or bar code readers 44 and/or RFID readers 44' and/or small mechanical forces with mechanical ratchet mechanisms 31" and/or other mechanical mechanisms that can be used to practice the invention and the invention is not limited to the specific combinations and/or embodiments described herein.

EXAMPLE-8

In another embodiment, a combination of automatic and manual movements of the one or more rolls of protective gloves 30 is used. In such an embodiment, a first dispensing event is detected on the one or more IR sensors 22 and the electronic circuit 18 sends one or more first electrical signals to the rack circuit 28, which generates and sends electrical signals to the electronic motor 29 to move a roll of protective gloves 30 in the glove roll rack 26 expose a first cuff end of a first protective glove 20. The user 74 then exerts the small downward mechanical force to break the connector 32 and completely dispense the first protective glove 20. The mechanical movement generates one more electrical signals in the glove roll rack that are sent the rack circuit 28. The rack circuit 28 then sends additional electronic signals to the electric motor 29 to expose a second cuff end 88' of a second protective glove 20' from the apparatus 12. Or based on more pre-determined timings (e.g., five to ten seconds, etc.) the electronic circuit 18 automatically sends additional electrical signals to the rack circuit 28 which then sends additional electronic signals to the electric motor 29 to expose a second cuff end 88' of a second protective glove 20' from the apparatus 12. The user 74 then exerts a second small downward mechanical force to completely dispense the second protective glove 20' by the second cuff end 88'. After manually dispensing the second protective glove 20, no additional protective gloves 20, 20' are exposed from the apparatus 12.

There are other combinations of protective gloves dispensing events, electrical signals, and/or small mechanical forces with and/or without mechanical ratchet mechanisms and/or other mechanical mechanisms that can be used to practice the invention and the invention is not limited to the specific combinations and/or embodiments described herein.

Figure 13:
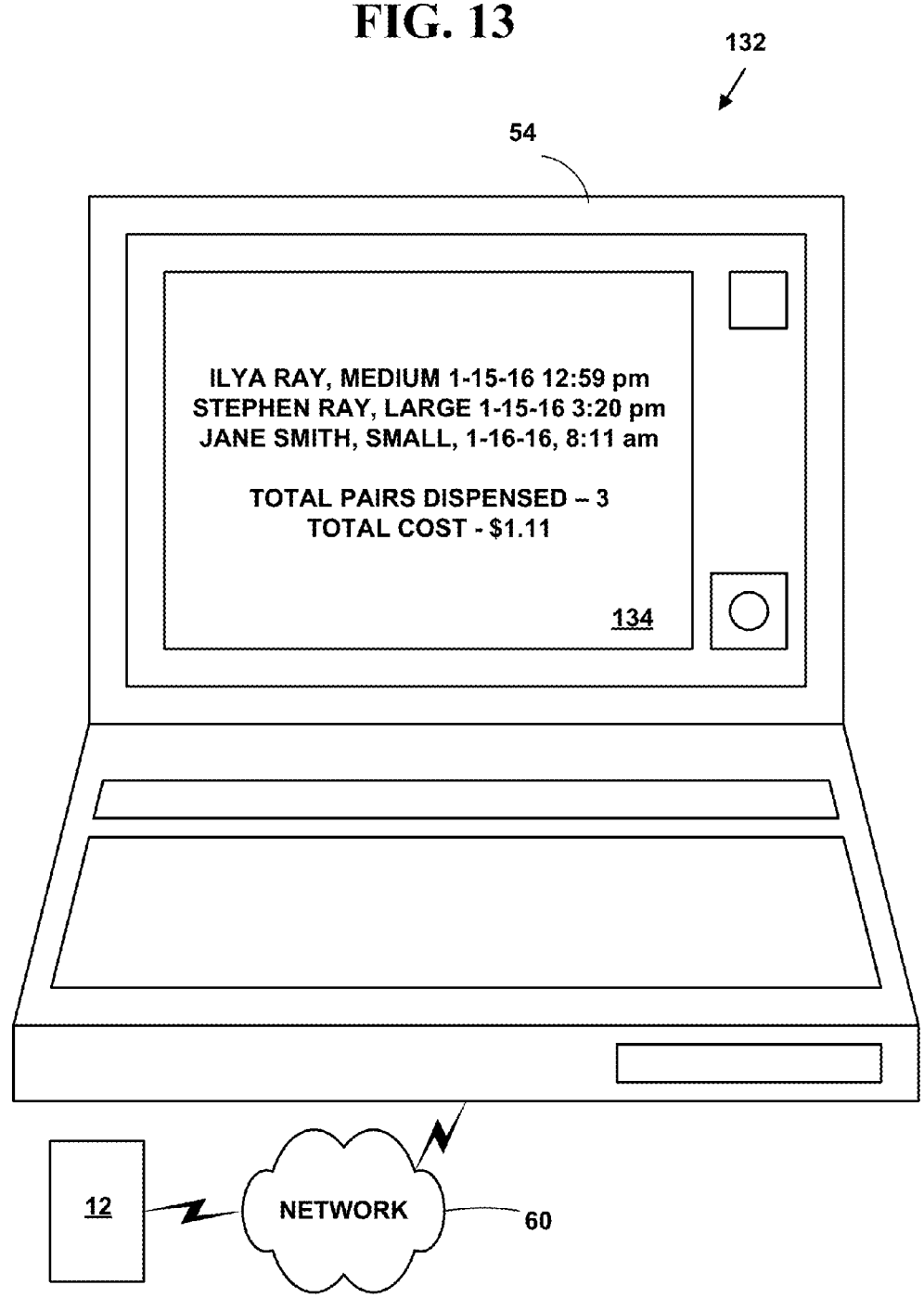
FIG. 13 is a block diagram illustrating an exemplary display of dispensing information collected from the sanitary automatic glove dispensing apparatus of FIG. 1.

FIG. 13 is a block diagram 132 illustrating an exemplary display of dispensing information 134 collected from the sanitary automatic glove dispensing apparatus 12 of FIG. 1.

The dispensing information 134 is collected and stored by application 40. The dispensing information 134 is available to network devices 52, 54, 56, 58 via network 60 and interface port 38 on apparatus 12. The dispensing information 134, includes but is not limited to, dispensing information such as user 74 name, size of gloves dispensed, time and date of gloves dispensed, etc. The dispensing information 134 is used to track activities of users 74 of protective gloves and is also used to track supply chain information such as number of gloves used, what size, how often, etc.

The dispensing information 134 can also be uploaded into other tracking systems such as a medical or other accounting system, patient or animal (e.g., veterinarian) tracking or cost tracking systems, employee management systems, product ordering systems, etc. However, the present invention is not limited to such dispensing information 134 and, more, fewer or other types of dispensing information can be used to practice the invention.

The dispensing information 134 is used to track and alter employee behavior (e.g., with identification badge 84, etc.). For example, if Jane Smith works as a food service worker, and she is required to change her gloves once every hour, and she is changing them once every three hours, the dispensing information 134 can be used by her manager to investigate why Jane is not changing her gloves every hour.

The dispensing information 134 is used to track compliance with glove changing rules in the medical and food industries. If an infection occurs in a patient, or an outbreak of a norovirus occurs in a hospital or restaurant, the dispensing information can be used to collect data and prove and/or disprove compliance procedures were followed. The dispensing information 134 may be used in a court of law in such instances to prove or disprove compliance with glove changing procedures. In the case of an infection occurring in an individual patient, the dispensing information 134 is used to track compliance of protective glove procedures by health care workers such as doctors, nurses, medical assistants, etc.

Automatic Protective Glove Dispensing Apparatus Methods of Use

FIGS. 14A and 14B are a flow diagram illustrating a Method 136 for automatically dispensing a pair of protective gloves 20, 20' by cuff ends 88, 88' with apparatus 12.

In FIG. 14A at Step 138, a first input signal is received on an electronic circuit in a sanitary automatic dispensing apparatus configured for automatically dispensing a pair of protective gloves by cuff ends, from one or more infrared (IR) sensors connected to the electronic circuit, the one or more infrared IR sensors including one more detection fields of one or more sizes and one or more detection orientations, the first input signal indicating detection of a first protective glove dispensing event. At Step 140, plural electrical signals are sent from the electronic circuit to a rack circuit on a glove roll rack to move a roll of protective gloves in the glove roll rack with an electric motor a plural number of times for: (1) automatically advancing the roll of protective gloves a first distance to expose a first protective glove by a first cuff end to a user; (2) automatically advancing the roll of protective gloves a second distance to fully dispense the first protective glove by the first cuff end to the user; (3) automatically advancing the roll of protective gloves a third distance to expose a second protective glove by a second cuff end to the user; (4) automatically advancing the roll of protective gloves a fourth distance to fully dispense the second protective glove by the second cuff end to the user, wherein the fourth distance fully dispenses the second protective glove without exposing another cuff end of another pair of protective gloves stored on the roll of protective gloves outside the apparatus thereby protecting the remaining pairs of protective gloves on the roll of protective gloves from contamination by a surrounding environment or by other users of the apparatus, wherein the roll of protective gloves includes plural individual protective gloves stored as pairs of protective gloves, wherein each of the individual gloves in the pair of protective gloves is rolled on the one or more rolls of protective gloves in a predetermined overlap pattern, wherein a pair of protective gloves from the plural protective gloves is dispensed from the one or more rolls of protective gloves by the cuff ends avoiding contaminating the finger surfaces by the user of the protective gloves during dispensing.

Method 136 is illustrated with an exemplary embodiment. However, the present invention is not limited to this exemplary embodiment and other embodiments can also be used to practice the invention.

In such an exemplary embodiment, in FIG. 14A at Step 138, a first input signal is received on an electronic circuit 18 in a sanitary automatic dispensing apparatus 12 configured for automatically dispensing a pair of protective gloves 20, 20' by cuff ends 88, 88', from one or more infrared (IR) 22 sensors connected to the electronic circuit 18, the one or more infrared IR sensors 28 including one more detection fields of one or more sizes 66, 70 and one or more detection orientations 64, 68, the first input signal indicating detection of a first protective glove dispensing event.

In FIG. 14B at Step 140, plural electrical signals are sent from the electronic circuit 18 to a rack circuit 28 on a glove roll rack 26 to move a roll of protective gloves 30 in the glove roll rack 30 with an electric motor 29 a plural number of times for: (1) automatically advancing the roll of protective gloves 30 a first distance to expose a first protective glove 20 by a first cuff end 88 to a user 74; (2) automatically advancing the roll of protective gloves 30 a second distance to fully dispense the first protective glove 20 by the first cuff end 88 to the user 74; (3) automatically advancing the roll of protective gloves 30 a third distance to expose a second protective glove 20' by a second cuff 88' end to the user 74; (4) automatically advancing the roll of protective gloves 30 a fourth distance to fully dispense the second protective glove 20' by the second cuff end 88' to the user 74, wherein the fourth distance fully dispenses the second protective glove 20' without exposing another cuff end of another pair 20, 20' of protective gloves stored on the roll of protective gloves 30 outside the apparatus 12 thereby protecting the remaining pairs of protective gloves 20, 20' on the roll of protective gloves 30 from contamination by a surrounding environment or by other users 74' of the apparatus, wherein the roll of protective gloves 30 includes plural individual protective gloves 20, 20' stored as pairs of protective gloves, wherein each of the individual gloves in the pair of protective gloves 30 is rolled on the one or more rolls of protective gloves 20, 20' in a pre-determined overlap pattern 90, 94, wherein a pair of protective gloves 20, 20' from the plural protective gloves 20, 20' is dispensed from the one or more rolls of protective gloves 30 by the cuff ends 88, 88' avoiding contaminating the finger 86, 86' surfaces by the user 74 of the protective gloves 20, 20' during dispensing.

In Method 136, after a first glove dispensing event is received, a pair of protective gloves 20, 20' is dispensed automatically based on plural electrical signals generated automatically from one or more pre-determined timings on the electronic circuit 18 without receiving any additional protective glove dispensing events generated by the user 74, either electronically or mechanically.

FIGS. 15A and 15B are a flow diagram illustrating a Method 142 for automatically dispensing a pair of protective gloves with apparatus 12.

In FIG. 15A at Step 144, a first input signal is received on an electronic circuit in a sanitary automatic dispensing apparatus configured for automatically dispensing a pair of protective gloves by cuff ends, from one or more infrared (IR) sensors connected to the electronic circuit, the one or more infrared IR sensors including one more detection fields of one or more sizes and one or more detection orientations, the first input signal indicating detection of a first protective glove dispensing event. At Step 146, one or more electrical signals are sent from the electronic circuit to a rack circuit on a glove roll rack with additional components comprising a mechanical ratchet mechanism, to move a roll of protective gloves in the glove roll rack with an electric motor to automatically advance the roll of protective gloves a first distance to expose a first protective glove by a first cuff end to a user, wherein the roll of protective gloves include plural individual protective gloves stored as pairs of protective gloves, the pairs of protective gloves connected with a pre-determined connector, wherein each of the individual gloves in the pair of protective gloves is rolled on the one or more rolls of protective gloves in a pre-determined overlap pattern, wherein a pair of protective gloves from the plural protective gloves is dispensed from the one or more rolls of protective gloves by the cuff ends avoiding contaminating the finger surfaces by a user of the protective gloves during dispensing. In FIG. 15B at Step 148, a first mechanical force generated by the user is received on the glove roll rack to mechanically advance the roll of protective gloves a second distance to fully dispense the first protective glove by the first cuff end to the user. At Step 150, a second mechanical force generated by the user is received on the glove roll rack to advance the roll of protective gloves a third distance to expose a second protective glove by a second cuff end to the user. At Step 152, a third mechanical force generated by the user is received to advance the roll of protective gloves a fourth distance to fully dispense the second protective glove by the second cuff end to the user, wherein the fourth distance fully dispenses the second protective glove without exposing another cuff end of another pair of protective gloves stored on the roll of protective gloves outside the apparatus thereby protecting the remaining pairs of protective gloves on the roll of protective gloves from contamination by a surrounding environment or by other users of the apparatus.

Method 142 is illustrated with an exemplary embodiment. However, the present invention is not limited to this exemplary embodiment and other embodiments can also be used to practice the invention.

In such an exemplary embodiment, in FIG. 15A at Step 144, a first input signal is received on an electronic circuit 18 in a sanitary automatic dispensing apparatus 12 configured for automatically dispensing a pair of protective gloves 20, 20' by cuff ends 88,88', from one or more infrared (IR) sensors 22 connected to the electronic circuit 18, the one or more infrared IR sensors 22 including one more detection fields of one or more sizes 66, 70 and one or more detection orientations 64, 68, the first input signal indicating detection of a first protective glove dispensing event.

At Step 146, one or more electrical signals are sent from the electronic circuit 18 to a rack circuit 28 on a glove roll rack 26 with additional roller/gear components 31' comprising a mechanical ratchet mechanism 31", to move a roll of protective gloves 30 in the glove roll rack 26 with an electric motor 29 to automatically advance the roll of protective gloves 30 a first distance to expose a first protective glove 20 by a first cuff end 88 to a user, wherein the roll of protective gloves include a plural individual protective gloves stored as pairs 20, 20' of protective gloves, the pairs of protective gloves 20, 20' connected with a pre-determined connector 20, wherein each of the individual gloves 20, 20' in the pair of protective gloves is rolled on the one or more rolls of protective gloves 30 in a pre-determined overlap pattern 90, 94, wherein a pair of protective gloves 20, 20' from the plural protective gloves is dispensed from the one or more rolls of protective gloves 30 by the cuff ends 88,88' avoiding contaminating the finger surfaces 86, 86' by a user 74 of the protective gloves 20, 20' during dispensing.

In FIG. 15B at Step 148, a first mechanical force 122 generated by the user is received on the glove roll rack 26 to mechanically advance the roll of protective gloves 30 a second distance to fully dispense the first protective glove 20 by the first cuff end 88 to the user 74.

At Step 150, a second mechanical force 122' generated by the user 74 is received on the glove roll rack 26 to advance the roll of protective gloves 30 a third distance to expose a second protective glove by a second cuff end to the user.

At Step 152, a third mechanical force 122" generated by the user 74 is received to advance the roll of protective gloves 30 a fourth distance to fully dispense the second protective glove 20' by the second cuff end 88' to the user 74, wherein the fourth distance fully dispenses the second protective glove 20' without exposing another cuff end 88 of another pair of protective gloves 20 stored on the roll of protective gloves outside the apparatus thereby protecting the remaining pairs of protective gloves 20, 20' on the roll of protective gloves 30 from contamination by a surrounding environment or by other users of the apparatus.

FIG. 16 is a flow diagram illustrating a Method 156 for automatically dispensing a pair of protective gloves 20, 20' with the sanitary automatic glove dispensing apparatus 12 of FIG. 1.

At Step 158, one or more dispensing event signals are received on an electronic circuit from the one or more IR sensors requesting dispensing of a pair of protective gloves. At Step 160, in response to the dispensing event signal, the electronic circuit sends one or more first electronic signals to a rack circuit in a glove roll rack to signal an electronic motor to move a selected roll of protective gloves in the glove roll rack a first pre-determined distance to automatically expose a cuff end of a first protective glove stored on the selected roll of protective gloves as a pair of protective gloves. At Step 162, after a pre-determined amount of time has expired, the electronic circuit sends one or more second signals to the rack circuit in the glove roll rack to signal the electronic motor to move the selected roll of protective gloves in the glove roll rack a second pre-determined distance to automatically fully dispense the first protective glove by the cuff end. At Step 164, after the pre-determined amount of time has expired, the electronic circuit sends one or more third electronic signals to the rack circuit in the glove roll rack to signal the electronic motor to move the selected roll of protective gloves in the glove roll rack a third pre-determined distance to automatically expose a cuff end of a second protective glove stored on the selected roll of protective gloves as a pair of protective gloves. At Step 166, after the pre-determined amount of time has expired, the electronic circuit sends one or more fourth signals to the rack circuit in the glove roll rack to signal the electronic motor to move the selected roll of protective gloves in the glove roll rack a second pre-determined distance to automatically fully dispense the second protective glove by the cuff end.

After Step 166, no additional protective gloves are exposed to the external environment from apparatus.

Method 156 is illustrated with an exemplary embodiment. However, the present invention is not limited to this exemplary embodiment and other embodiments can also be used to practice the invention.

In such an exemplary embodiment, at Step 158, one or more dispensing event signals are received on an electronic circuit 18 from the one or more IR sensors 22 requesting dispensing of a pair of protective gloves 20, 20'.

At Step 160, in response to the dispensing event signal, the electronic circuit 18 sends one or more first electronic signals to a rack circuit 28 in a glove roll rack 26 to signal an electronic motor 29 to move a selected roll of protective gloves 30 in the glove roll rack 30 a first pre-determined distance to expose a cuff end 88 of a first protective glove 20 stored on the selected roll of protective gloves 20 as a pair of protective gloves 20, 20'.

At Step 162, after a pre-determined amount of time has expired, the electronic circuit sends 18 one or more second signals to the rack circuit 28 in the glove roll rack 26 to signal the electronic motor 29 to move the selected roll of protective gloves 30 in the glove roll rack 26 a second pre-determined distance to fully dispense the first protective glove 20 by the cuff end 88.

At Step 164, after the pre-determined amount of time has expired, the electronic circuit 18 sends one or more third electronic signals to the rack circuit 28 in the glove roll rack 26 to signal the electronic motor 29 to move the selected roll of protective gloves 30 in the glove roll rack 26 a third pre-determined distance to expose a cuff end 88' of a second protective glove 20' stored on the selected roll of protective gloves 30 as a pair of protective gloves 20, 20'.

At Step 166, after the pre-determined amount of time has expired, the electronic circuit 18 sends one or more fourth signals to the rack circuit 28 in the glove roll rack 26 to signal the electronic motor 29 to move the selected roll of protective gloves 30 in the glove roll rack 26 a fourth pre-determined distance to fully dispense the second protective glove 20' by the cuff end 88'. After Step 166, no additional protective gloves 20", 20''' are exposed to the external environment from apparatus 12.

In one embodiment, Step 166 further includes moving the selected roll of protective gloves 30 the predetermined space 97 (FIG. 9B) between the pairs of protective gloves 20, 20' and the next pair of protective gloves 20", 20''' on the roll of protective gloves 30 to prepare the apparatus 12 for a next glove dispensing event.

In another embodiment, the predetermined space 97 (FIG. 9B) between the pairs of protective gloves 20, 20' and the next pair of protective gloves 20", 20''' on the roll of protective gloves 30 is moved when a next dispensing event signal is received on the electronic circuit.

In one embodiment, all of the pre-determined timings include the same amount of time (e.g., five to ten seconds). In another embodiment, the pre-determined timings may include different amounts of time. Various combinations of pre-determined times can be used to practice the invention.

In such an embodiment using Method 154, the one or more pre-determined timings are adjusted through the interface port 38 on apparatus 12.

With Method 156, a user 74 only has to activate the apparatus 12 once with a hand 76, 76', and/or torso 78 and/or bar code 46 and/or RFID tag on an identification card 84 or other card 84 to fully dispense a pair of protective gloves 20, 20'.

In another embodiment, the expiration of the pre-determined about of time on the electronic circuit 18 at steps 162, 164, 166 is replaced with receiving one or more second, third and fourth signals from the one or more IR sensors 22 on the electronic circuit 18 generated by the user 74. In such an embodiment, the user 74 activates the one or more IR sensors 22, 22', 22''' four times to dispense one pair of protective gloves 20, 20'.

FIG. 17 is a flow diagram illustrating a Method 168 for automatically dispensing a pair of protective gloves with the sanitary automatic glove dispensing apparatus of FIG. 1.

At Step 170 a first dispensing event signal is received on an electronic circuit from one or more IR sensors requesting dispensing of a pair of protective gloves and the electronic circuit sends one or more first electronic signals to a rack circuit in a glove roll rack in a gloved dispensing apparatus to signal an electric motor to move a selected roll of protective gloves in the glove roll rack a first pre-determined distance to expose a cuff end of a first protective glove stored on the selected roll of protective gloves as a pair of protective gloves. At Step 172, a second dispensing event is received on the electronic circuit from the one or more IR sensors and the electronic circuit sends one or more second signals from the rack circuit in the glove roll rack to signal the electric motor to move the selected roll of protective gloves in the glove roll rack a second pre-determined distance to fully dispense the first protective glove by the cuff end. At Step 174, a third first dispensing event signal is received on the electronic circuit from the one or more IR sensors and the electronic circuit sends one or more third electronic signals to the rack circuit in the glove roll rack to signal the electric motor to move a selected roll of protective gloves in the glove roll rack a third pre-determined distance to expose a cuff end of a second protective glove stored on the selected roll of protective gloves as a pair of protective gloves. At Step 176, a fourth dispensing event is received on the electronic circuit from the one or more IR sensors and the electronic circuit sends one or more fourth signals to the rack circuit in the glove roll rack to signal the electric motor to move the selected roll of protective gloves in the glove roll rack a fourth pre-determined distance to fully dispense the second protective glove by the cuff end.

Method 168 is illustrated with an exemplary embodiment. However, the present invention is not limited to this exemplary embodiment and other embodiments can also be used to practice the invention.

In such an exemplary embodiment, at Step 170 a first dispensing event signal is received on an electronic circuit 18 from one or more IR sensors 22 requesting dispensing of a pair of protective gloves 20, 20' and the electronic circuit 18 sends one or more first electronic signals to a rack circuit 28 in a glove roll rack 26 in the apparatus 12 to signal an electric motor 29 to move a selected roll of protective gloves 30 in the glove roll rack 26 a first pre-determined distance to expose a cuff end 88 of a first protective glove 20 stored on the selected roll of protective gloves 30 as a pair of protective gloves 20, 20'.

At Step 172, a second dispensing event is received on the electronic circuit 18 from the one or more IR sensors 22 and the electronic circuit 18 sends one or more second signals from the rack circuit 28 in the glove roll rack 26 to signal the electric motor 29 to move the selected roll of protective gloves 30 in the glove roll rack a second pre-determined distance to fully dispense the first protective glove 20 by the cuff end 88'.

At Step 174, a third first dispensing event signal is received on the electronic circuit 18 from the one or more IR sensors 22 and the electronic circuit 18 sends one or more third electronic signals to the rack circuit 28 in the glove roll rack 26 to signal the electric motor 29 to move a selected roll of protective gloves 30 in the glove roll rack 26 a third pre-determined distance to expose a cuff end 88' of a second protective glove 20' stored on the selected roll of protective gloves 30 as a pair of protective gloves 20, 20'.

At Step 176, a fourth dispensing event is received on the electronic circuit 18 from the one or more IR sensors 22 and the electronic circuit 18 sends one or more fourth signals to the rack circuit 18 in the glove roll rack 26 to signal the electric motor 29 to move the selected roll of protective gloves 30 in the glove roll rack 26 a fourth pre-determined distance to fully dispense the second protective glove 20' by the cuff end 18'.

In another embodiment, the expiration of the pre-determined about of time on the electronic circuit 18 at steps 162, 164, 166 is replaced with receiving one or more second, third and fourth signals from the one or more IR sensors 22 on the electronic circuit 18 generated by the user 74. In such an embodiment, the user 74 activates various combinations of the one or more IR sensors 22, 22', 22''' and/or bar code reader 44 and/or RFID tag reader 44' four times to dispense one pair of protective gloves 20, 20'.

In another embodiment, the expiration of the pre-determined about of time on the electronic circuit 18 at steps 162, 164, 166 is replaced with receiving one or more second, third and fourth signals from bar code reader 44 and/or the RFID reader 44' on the electronic circuit 18 generated by the user 74. In such an embodiment, the user 74 activates the bar code reader 44 and/or RFID tag reader 44' four times to dispense one pair of protective gloves 20, 20'.

In another embodiment, other combinations of user 74 activations and pre-determined timings steps are used to dispense one pair of protective gloves 20, 20'. For example, a user 74 may use a hand 76, 76' (and/or bar code 46 and/or RFID tag 48) to start the dispensing process which automatically dispenses a first glove 20 from the pair of protective gloves 20, 20'. The user may then use the hand 76, 76' (and/or bar code 46 and/or RFID tag 48) again to automatically full dispense the second glove 20' from the pair of protective gloves 20, 20'.

However, the present inventions is not limited to the embodiments described and other embodiments with other combinations of activation events and pre-determined timings can be used to practice the invention.

Figure 18:
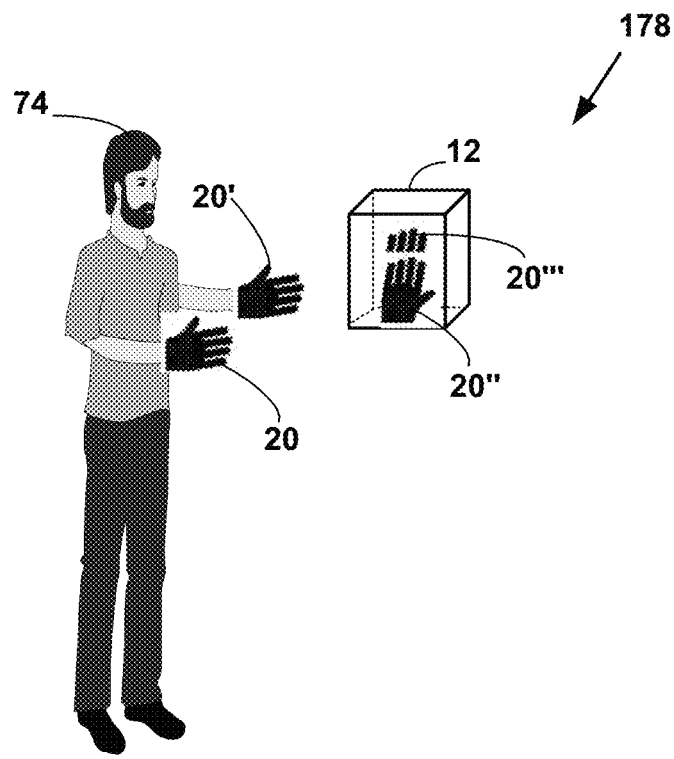
FIG. 18 is a block diagram illustrating the sanitary automatic glove dispensing apparatus of FIG. 1 after fully dispensing a pair of protective gloves to a user.

FIG. 18 is a block diagram 178 illustrating the sanitary automatic glove dispensing apparatus 12 of FIG. 1 after fully dispensing a pair of protective gloves 20, 20' to a user 74. As is illustrated in FIG. 18, no portion of the next pair of protective gloves 20" and 20''' is extended outside the apparatus 12 after dispensing the first pair of protective gloves 20, 20'.

Figure 19:
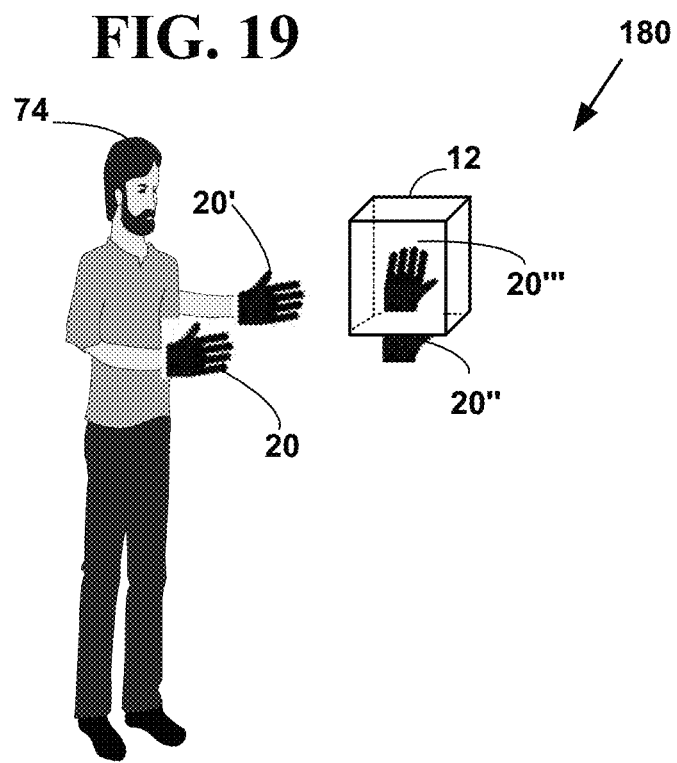
FIG. 19 is a block diagram illustrating the sanitary automatic glove dispensing apparatus of FIG. 1 after fully dispensing a pair of protective gloves to a user.

FIG. 19 is a block diagram 180 illustrating the sanitary automatic glove dispensing apparatus 12 of FIG. 1 after fully dispensing a pair of protective gloves 20, 20' to a user 74. As is illustrated in FIG. 19, a small portion of the next pair of protective gloves 20" and 20''' is extended outside the apparatus 12 after dispensing the first pair of protective gloves 20, 20' in this alternative configuration.

In another embodiment, the pre-determined distance 97 is removed from between each pair of protective gloves 20, 20' on the one or more rolls of protective gloves and each pair of protective gloves 20, 20' on the roll not connected. In such an embodiment, a small portion of the cuff end 88 of a protective glove 20 is extended from dispensing slot 34 of the apparatus 12 and is exposed to the external environment.

In another embodiment, the pre-determined distance 97 is not removed from between each pair of protective gloves 20, 20' on the one or more rolls of protective gloves and each pair of protective gloves 20, 20' on the roll not connected. A small portion of the cuff end 88 of a next pair of protective glove 20", 20''' is extended from dispensing slot 34 of the apparatus 12 and is exposed to the external environment without any protection after each pair of protective gloves 20, 20' is dispensed.

In another embodiment, a small portion of a cuff end 88 of a protective glove 20 is extended from dispensing slot 34 of the apparatus 12. The dispensing slot 34 further includes an extended dispensing membrane 36' (FIG. 10) that covers a majority of the exposed cuff end 88 of the protective gloves. In one embodiment with an extended dispensing membrane 36', the extended dispensing membrane 36' is selectively removable and attachable from dispensing slot 34 and is changed when the one or more rolls of protective gloves 30 are changed after being fully dispensed.

However, the present inventions is not limited to these embodiments and other embodiments with other combinations of elements can be used to practice the invention.

The drawings included herein illustrate protective gloves 20, 20' extending out of the glove dispensing apparatus 12 with a thumb of a finger portion 86 exposed to further illustrate features of the invention. However, in an actual embodiment, only a small portion of the cuff portion 88, 88' of a protective glove 20, 20' is exposed to the surrounding environment.

The embodiments described herein dispense a pair of protective gloves 20, 20' by the cuff ends 88, 88' and prevent contamination of the finger surface 86, 86' of the protective gloves. The present invention helps to dramatically decrease hand and to person transfer of pathogenic organisms by health care and food service workers.

A sanitary automatic glove dispensing apparatus and methods of use is described herein. The automatic sanitary glove dispensing apparatus, based on one or more received dispensing events, dispenses pairs of connected protective gloves stored on a roll of protective gloves as the pair of protective gloves and overlapped in a pre-determined pattern, by both cuff ends so finger ends of the protective gloves are not contaminated during dispensing. After a pair of protective gloves are dispensed by both cuff ends, no additional protective gloves are exposed from the apparatus until another protective glove dispensing event is received, thereby protecting remaining protective gloves in the apparatus from the surrounding environment and from the other users of the apparatus.

It should be understood that the architecture, programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

While various elements of the preferred embodiments have been described as being implemented in software, in other embodiments hardware or firmware implementations may alternatively be used, and vice-versa.

The claims should not be read as limited to the described order or elements unless stated to that effect. In addition, use of the term "means" in any claim is intended to invoke 35 U.S.C. § 112, paragraph 6, and any claim without the word "means" is not so intended. Therefore, all embodiments that come within the scope and spirit of the following claims and equivalents thereto are claimed as the invention.

I claim:

1. A sanitary automatic glove dispensing apparatus comprising:
   a protective case;
   an integrated electronic circuit including an interface port and one or more processors connected to at least one power supply and configured for automatically dispensing protective gloves by cuff ends;
   one or more infrared (IR) sensors connected to the electronic circuit;
   one or more light emitting diodes (LEDs) connected to the electronic circuit and activated by the one or more infrared IR sensors for visually indicating one or more operational states of the apparatus;
   one or more rolls of protective gloves including a plurality of individual protective gloves connected with a connector and rolled in a glove roll rack in an overlap pattern such that each of protective gloves is dispensed by the cuff ends avoiding contaminating the finger surfaces, the glove roll rack including a rack circuit connected to the integrated electronic circuit and an electronic motor connected to the at least one power supply for moving the roll to dispense the protective gloves completely by the cuff ends without exposing another protective glove; and
   one or more application programs comprising a plurality of instructions in the non-transitory computer readable medium for causing the one or more processors to configure via the interface port a detection field size and a detection field orientation for the one or more infrared (IR) sensors, one or more timings for automatically dispensing protective gloves after first dispensing event is detected and to collect and transmit dispensing information.

2. The sanitary automatic glove dispensing apparatus of claim 1 wherein the power source includes an alternating current (AC) power source or a direct current (DC) power source, or both an AC and a DC power source.

3. The sanitary automatic glove dispensing apparatus of claim 1 further including:
   a dispensing slot in a surface of the protective case for dispensing the protective gloves by the cuff ends; and
   a dispensing membrane integral to the dispensing slot for protecting the gloves during dispensing and for protecting the plurality of protective gloves remaining on the one or more rolls of protective gloves from contamination from an external environment.

4. The sanitary automatic glove dispensing apparatus of claim 1 wherein the one or more application programs are configurable via the interface port from a network device with one or more processors with a wired or wireless connection over a communications network.

5. The sanitary automatic glove dispensing apparatus of claim 4 wherein the network device includes a smart phone, electronic tablet, laptop computer or desktop computer.

6. The sanitary automatic glove dispensing apparatus of claim 1 wherein the one or more infrared (IR) sensors include a passive infrared sensor, an active infrared sensor, a color detecting infrared sensor or a bar code reading infrared sensor.

7. The sanitary automatic glove dispensing apparatus of claim 1 further comprising an audio speaker connected to the electronic circuit for indicating with an audio sound or tone the one or more IR sensors have detected the user and for providing pre-recorded audio instructions to dispense a pair of protective gloves by cuff ends for a user.

8. The sanitary automatic glove dispensing apparatus of claim 1 wherein the detection field includes four to six inch detection field size and the detection orientation includes a forward, downward, upward or side-ways facing orientation.

9. The sanitary automatic glove dispensing apparatus of claim 1 further comprising a Radio Frequency Identifier (RFID) reader for reading RFID signals from and RFID tag.

10. The sanitary automatic glove dispensing apparatus of claim 1 further including a Liquid Crystal Display (LCD) display for displaying status, error status, size, remaining quantity, dispensing instructions, dispensing information and other information to a user of apparatus.

11. The sanitary automatic glove dispensing apparatus of claim 1 wherein the protective gloves include medical gloves, food service gloves and other types of protective gloves.

12. The sanitary automatic glove dispensing apparatus of claim 1 wherein the protective gloves include protective gloves comprising latex, nitrile rubber, vinyl, neoprene or polyethylene materials and further include sterile or non-sterile protective gloves.

13. The sanitary automatic glove dispensing apparatus of claim 1 wherein the overlap pattern of a pair of protective gloves includes overlapping a second finger portion and second palm portion of a second protective glove with a first finger portion and a first palm portion of a first protective glove such that only a first cuff portion of the first protective glove from the pair of protective gloves is exposed after a first dispensing event is detected.

14. The sanitary automatic glove dispensing apparatus of claim 1 further comprising one or more rolls of protective gloves including a plurality of individual protective gloves stored as pairs of protective gloves without the pre-determined connector connecting pairs of protective gloves, wherein the plurality of pairs of protective gloves are stored in the pre-determined overlap pattern with a pre-determined distance between the pairs of protective gloves so the plurality of pairs of protective gloves are also dispensed by the cuff ends.

15. The sanitary automatic glove dispensing apparatus of claim 1 wherein the one or more rolls of protective gloves are stored around a vertical axis.

16. The sanitary automatic glove dispensing apparatus of claim 1 further comprising one or more gears, arms and springs comprising a ratchet mechanism for accepting a plurality of manual forces from a user for breaking the connection between a pair of adjacent protective gloves and manually dispensing the protective gloves after a first glove dispensing event is detected by the one or more IR sensors.

17. The sanitary automatic glove dispensing apparatus of claim 3 wherein the dispensing membrane is coated with an antimicrobial compound to prevent contamination of the pairs of protective gloves on the one or more rolls of protective gloves stored in the apparatus from the surrounding environment.

18. The sanitary automatic glove dispensing apparatus of claim 1 wherein the connector includes a mechanical connector, or a connector created by a chemical, heat or mechanical compression bond.

19. A method for sanitary automatic protective glove dispensing comprising:
providing a sanitary automatic dispensing apparatus configured for automatically dispensing protective gloves rolled into one or more rolls in an overlap pattern such that the protective gloves are dispensed by the cuff ends avoiding contaminating the finger surfaces;
receiving a first input signal from one or more infrared (IR) sensors connected to an electronic circuit in the sanitary automatic dispensing apparatus, the one or more infrared IR sensors including one more detection fields of one or more sizes and one or more detection orientations, the first input signal indicating detection of a first protective-glove dispensing event;
sending a plurality of electrical signals from the electronic circuit to a rack circuit on a glove roll rack to move the glove roll with an electric motor a plurality of times for:
automatically advancing a roll of protective gloves a first distance to expose a first protective glove by a first cuff end to a user;
automatically advancing the roll of protective gloves a second distance to fully dispense the first protective glove by the first cuff end to the user without exposing a second cuff end of a second protective glove stored in the roll adjacent the first glove, thereby protecting the remaining protective gloves on the roll from contamination,
wherein the plurality of electrical signals are generated automatically based on one or more timings without receiving any additional protective-glove dispensing events or generated based on receiving one or more additional protective-glove dispensing events detected by the one or more IR sensors.

20. The method of claim 19 wherein the step of sending a plurality of electrical signals further comprising:
automatically advancing the roll of protective gloves a third distance to expose a second protective glove by a second cuff end to the user; and
automatically advancing the roll of protective gloves a fourth distance to fully dispense the second protective glove by the second cuff end to the user, wherein the fourth distance fully dispenses the second protective glove without exposing another cuff end of another pair of protective gloves stored on the roll of protective gloves outside the apparatus thereby protecting the remaining pairs of protective gloves in the roll from contamination.

21. A method for sanitary automatic protective glove dispensing, comprising:
providing a sanitary automatic dispensing apparatus configured for automatically dispensing protective gloves rolled into one or more rolls in an overlap pattern such that the protective gloves are dispensed by the cuff ends avoiding contaminating the finger surfaces;
receiving a first input signal from one or more infrared (IR) sensors connected to an electronic circuit in the sanitary automatic dispensing apparatus, the one or more infrared IR sensors including one more detection fields of one or more sizes and one or more detection orientations, the first input signal indicating detection of a first protective glove dispensing event;
sending one or more electrical signals from the electronic circuit to a rack circuit on a glove roll rack with additional components comprising a mechanical ratchet mechanism, to move a roll of protective gloves in the glove roll rack with an electric motor to automatically advance the roll of protective gloves a first distance to expose a first protective glove by a first cuff end to a user, the electrical signals being generated automatically based on one or more timings without receiving any additional protective-glove dispensing events or generated based on receiving one or more additional protective-glove dispensing events detected by the one or more IR sensors,
receiving a first mechanical force generated by the user on the glove roll rack to mechanically advance the roll of protective gloves a second distance to fully dispense the first protective glove by the first cuff end to the user;
receiving a second mechanical force generated by the user on the glove roll rack to advance the roll of protective gloves a third distance to expose a second protective glove by a second cuff end to the user;
receiving a third mechanical force generated by the user to advance the roll of protective gloves a fourth distance to fully dispense the second protective glove by the second cuff end to the user, wherein the fourth distance fully dispenses the second protective glove without exposing another cuff end of another pair of protective gloves stored on the roll of protective gloves outside the apparatus thereby protecting the remaining pairs of protective gloves on the roll of protective of protective gloves from contamination.

* * * * *